(12) United States Patent
Sum et al.

(10) Patent No.: US 6,444,685 B1
(45) Date of Patent: Sep. 3, 2002

(54) N-(4-SULFONYLARYL)CYCLYLAMINE 2-HYDROXYETHYLAMINES AS BETA-3 ADRENERGIC RECEPTOR AGONISTS

(75) Inventors: Fuk-Wah Sum, Pomona, NY (US); Michael Sotirios Malamas, Jamison, PA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 09/904,114

(22) Filed: Jul. 12, 2001

Related U.S. Application Data

(60) Provisional application No. 60/218,589, filed on Jul. 17, 2000.

(51) Int. Cl.[7] ............. C07D 401/12; C07D 211/58; C07D 417/14; A61K 31/4545; A61P 3/10
(52) U.S. Cl. ............. 514/317; 514/319; 514/320; 514/321; 514/322; 514/323; 514/324; 514/326; 546/192; 546/196; 546/197; 546/198; 546/199; 546/200; 546/202
(58) Field of Search .................. 546/199, 208, 546/223, 192, 195, 196, 197, 198, 200, 202; 544/360; 514/322, 329, 326, 253.01, 317, 319, 320, 321, 323, 324

(56) References Cited

U.S. PATENT DOCUMENTS

| | | | |
|---|---|---|---|
| 5,561,142 A | 10/1996 | Fisher et al. | 514/352 |
| 5,578,620 A | 11/1996 | Fujita et al. | 514/370 |
| 5,614,523 A | 3/1997 | Audia et al. | 514/252 |
| 5,741,789 A | 4/1998 | Hibschman | 514/210 |
| 5,786,356 A | 7/1998 | Bell et al. | 514/248 |
| 5,789,402 A | 8/1998 | Audia et al. | 514/213 |
| 6,069,176 A | 5/2000 | Tsuchiya et al. | 514/646 |

FOREIGN PATENT DOCUMENTS

| | | |
|---|---|---|
| EP | 0 449 261 A1 | 10/1991 |
| EP | 0 659 737 A2 | 6/1995 |
| EP | 0 714 883 A1 | 6/1996 |
| EP | 0 764 640 A1 | 3/1997 |
| WO | WO 99/25687 A1 * | 5/1999 |
| WO | WO99/65895 | 12/1999 |
| WO | WO01/17989 A2 | 3/2001 |
| WO | WO01/43744 A1 | 6/2001 |
| WO | WO01/44227 A1 | 6/2001 |

OTHER PUBLICATIONS

Marc S. Berridge et al., Nucl. Med. Biol., 1992, 563–569, 19(5).
Joan M Caroon et al., J. Pharm. Sci. Jan. 1987, 32–34, 76(1).
A. Guy et al., Synthesis, Sep. 1992, 821–22.
Manabu Hori et al., J. Org. Chem., 1998, 889–894, 63.
Yusheng Huang et al., J. Med. Chem., 1998, 2361–2370, 41.
Bernard Hulin et al., J. Med. Chem., 1992, 1853–1864, 35.
Carl Kaiser et al., J. Med. Chem., 1977, 687–692, 20(5).
Yutaka Kawashima et al., Chem. Pharm. Bull., 1995, 1132–1136, 43(7).
Kiyoto Koguro et al, Synthesis, 1998, 910–914.
Gerard Leclerc et al., J. Med. Chem., 1980, 738–744, 23(7).
D. Mauleon et al., II Farmaco, 1989, 1109–1117, 44(11).
Alexander McKillop et al., J. Am. Chem. Soc., Sep. 1971, 4919–4920, 93(19).
Ricardo Tapia et al, Synthetic Communications, 1986, 681–687, 16(6).
Edward C. Taylor et al., Synthesis, Aug. 1981, 606–608.
Michiaki Tominaga et al., Chem. Pham. Bull, 1987, 3699–3704, 35(9).
R.H. Uloth et al., J. Med. Chem., 1966, 88–97, 9.
Paul C. Unangst et al., J. Med. Chem, 1994, 322–328, 37.
Sophie Vanwetswinkel et al., J. Antibiotics, Sep. 1994, 1041–1051, 47(9).
S. Tamada et al., JP 01061468 A2 (English abstract), 1989.
Baihua HU et al., J. Med. Chem., 2001, 1456–1466, 44.

* cited by examiner

*Primary Examiner*—Bruck Kifle
(74) *Attorney, Agent, or Firm*—Arnold S. Milowsky

(57) ABSTRACT

This invention provides compounds of Formula I having the structure

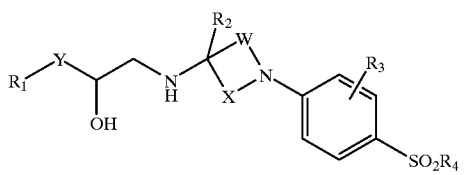

wherein $R_1$, $R_2$, $R_3$, $R_4$, W, X, and Y are as defined hereinbefore or a pharmaceutically acceptable salt thereof, which are useful in treating metabolic disorders related to insulin resistance or hyperglycemia.

10 Claims, No Drawings

N-(4-SULFONYLARYL)CYCLYLAMINE 2-HYDROXYETHYLAMINES AS BETA-3 ADRENERGIC RECEPTOR AGONISTS

This application claims the benefit of U.S. Provisional Application No. 60/218,589, filed Jul. 17, 2000.

BACKGROUND OF THE INVENTION

This invention relates to N-(4-sulfonylaryl)cyclylamine 2-hydroxyethylamine derivatives which are $\beta_3$ adrenergic receptor agonists useful for the treatment of metabolic disorders related to insulin resistance or hyperglycemia (typically associated with obesity or glucose intolerance), atherosclerosis, gastrointestinal disorders, neurogenetic inflammation, glaucoma, ocular hypertension, and and frequent urination, and are particularly useful in the treatment or inhibition of type II diabetes.

The subdivision of $\beta$ adrenergic receptors ($\beta$-AR) into $\beta_1$- and $\beta_2$-AR has led to the development of $\beta_1$- and $\beta_2$-antagonists and/or agonists which have been useful for the treatment of cardiovascular disease and asthma. The recent discovery of "atypical" receptors, later called $\beta_3$-AR, has led to the development of $\beta_3$-AR agnoists which may be potentially useful as antiobesity and antidiabetic agents. For recent reviews on $\beta_3$-AR agnoists , see: 1. A. D. Strosberg, Annu. Rev. *Pharmacol. Toxicol.* 1997, 37, 421;2. A. E. Weber, *Ann. Rep. Med. Chem.* 1998, 33, 193; 3. C. P. Kordik and A. B. Reitz, *J. Med. Chem.* 1999, 42, 181; 4. C. Weyer, J. F. Gautier and E. Danforth, *Diabetes and Metabolism*, 1999, 25, 11.

Compounds that are potent and selective $\beta_3$ agonists, may be potentially useful antiobesity agents. Low levels or lack of $\beta_1$ and $\beta_2$-agonistic properties will minimize or eliminate the adverse side effects that are associated with $\beta_1$ and $\beta_2$ agonistic activities, i.e. increased heart rate, and muscle tremor, respectively.

Early developments in the $\beta_3$-agonist field are described in European patent 427480, U.S. Pat. Nos. 4,396,627, 4,478, 849, 4,999,377, 5,153,210. Although the early developments purport to claim compounds with greater $\beta_3$-AR selectivity over the $\beta_1$- and $\beta_2$-AR. However, clinical trials in humans with those early developed $\beta_3$-agonists have, so far, not been successful.

More recently, potent and selective human $\beta_3$ agonists have been described in several patents and published applications: WO 98/32753, WO 97/46556, WO 97/37646, WO 97/15549, WO 97/25311, WO 96/16938, WO 95/29159, European Patents 659737, 801060, 714883, 764640, 827746, and U.S. Pat. Nos. 5,561,142, 5,705,515, 5,436, 257, and 5,578,620. These compounds were evaluated in Chinese hamster ovary (CHO) cells test procedures, expressing cloned human $\beta_3$ receptors, which predict the effects that can be expected in humans (Granneman et al., *Mol Pharmacol.*, 1992, 42, 964; Emorine et al., *Science*, 1989, 245, 1118; Liggett *Mol. Pharmacol.*, 1992, 42, 634).

$\beta_3$-Adrenergic agonists also are useful in controlling the frequent urge of urination. It has been known that relaxation of the bladder detrusor is under beta adrenergic control (Li J H, Yasay G D and Kau S T *Pharmacology* 1992; 44: 13–18). Beta-adrenoceptor subtypes are in the detrusor of guinea-pig urinary bladder. Recently, a number of laboratories have provided experimental evidence of $\beta_3$ adrenergic receptors in a number of animal species including human (Yamazaki Y, Takeda H, Akahane M, Igawa Y, et al. *Br. J. Pharmacol.* 1998; 124: 593–599), and that activation of the $\beta_3$ receptor subtype by norepinephrine is responsible for relaxation of the urinary bladder.

Urge urinary incontinence is characterized by abnormal spontaneous bladder contractions that can be unrelated to bladder urine volume. Urge urinary incontinence is often referred to hyperactive or unstable bladder. Several etiologies exist and fall into two major categories, myogenic and neurogenic. The myogenic bladder is usually associated with detrusor hypertrophy secondary to bladder outlet obstruction, or with chronic urinary tract infection. Neurogenic bladders are associated with an uninhibited micturition reflex. An upper motor neuron disease is usually the underlying cause. In either case, the disease is characterized my abnormal spontaneous contractions that result in an abnormal sense of urinary urgency and involuntary urine loss. At present, the most common therapy for hyperactive bladder includes the use of antimuscarinic agents to block the action of the excitatory neurotransmitter acetylcholine. While effective in neurogenic bladders, their utility in myogenic bladders is questionable. In addition, due to severe dry mouth side-effects associated with antimuscarinic therapy, the patient compliance with these agents is only approximately 30%.

In the bladder, $\beta_3$ adrenergic receptor agonists activate adenylyl cyclase and generate cAMP through the G-protein coupled $\beta_3$ receptor. The resulting phosphorylation of phospholamban/calcium ATPase enhances uptake of calcium into the sarcoplasmic reticulum. The decrease in intracellular calcium inhibits bladder smooth muscle contractility.

It is suggested therefore, that activation of the $\beta_3$ adrenergic receptor in the urinary bladder will inhibit abnormal spontaneous bladder contractions and be useful for the treatment of bladder hyperactivity. Note, that unlike the antimuscarinics, $\beta_3$ adrenergic receptor agonists would be expected to be active against both neurogenic and myogenic etiologies.

Despite all these recent developments there is still no single therapy available for the treatment of type II diabetes (NIDDM), obesity, atherosclerosis, gastrointestinal disorders, neurogenetic inflammation, frequent urination and related diseases. A potent and selective $\beta_3$ adrenergic receptor agonist is therefore highly desirable for the potential treatment of such disease states.

DESCRIPTION OF THE INVENTION

This invention provides compounds of Formula I having the structure

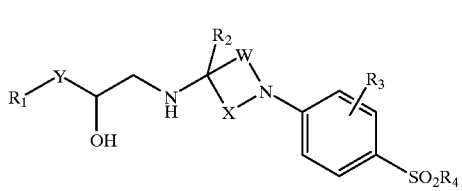

wherein:
W is $(CH_2)_m$;
X is $(CH_2)_n$;
Y is $OCH_2$, $SCH_2$, or a bond;
$R_1$ is phenyl substituted with $R_5$ and $R_6$, or Het substituted with $R_5$ and $R_6$;
$R_2$ is hydrogen, trifluoromethyl, alkyl of 1–6 carbon atoms, alkenyl of 2–7 carbon atoms, or alkynyl of 2–7 carbon atoms;

$R_4$ is alkyl of 1–6 carbon atoms, alkenyl of 2–7 carbon atoms, alkynyl of 2–7 carbon atoms, cycloalkyl of 3–8 carbon atoms, hydroxy, aryl substituted with $R_5$ and $R_6$, Het substituted with $R_5$ and $R_6$, aryloxy, —NHCOR$_7$, —NR$_8$R$_8$, —CR$_3$R$_5$R$_6$, arylamino, Het-amino, arylalkylamino having 1–6 carbon atoms in the alkyl chain, Het-alkylamino having 1–6 carbon atoms in the alkyl chain, alkoxycarbonylalkyl of 3–13 carbon atoms, carboxyalkyl of 2–7 carbon atoms, alkylcarbonylalkyl of 3–13 carbon atoms, arylcarbonylalkyl having 1–6 carbon atoms in the alkyl chain, Het-carbonylalkyl having 1–6 carbon atoms in the alkyl chain, aminocarbonylalkyl of 2–7 carbon atoms, alkylaminocarbonylalkyl of 3–13 carbon atoms, arylaminocarbonylalkyl having 1–6 carbon atoms in the alkyl chain, Het-aminocarbonylalkyl having 1–6 carbon atoms in the alkyl chain, aminosulfonylalkyl of 1–6 carbon atoms, alkylsulfonylalkyl of 2–12 carbon atoms, arylsulfonylalkyl having 1–6 carbon atoms in the alkyl chain, alkylaminosulfonylalkyl of 2–12 carbon atoms, arylaminosulfonylalkyl having 1–6 carbon atoms in the alkyl chain, Het-aminosulfonylalkyl having 1–6 carbon atoms in the alkyl chain, phosphonylalkyl of 1–6 carbon atoms, or phosphorylalkyl of 1–6 carbon atoms;

$R_3$, $R_5$, and $R_6$, are each, independently, hydrogen, trifluoromethyl, alkyl of 1–6 carbon atoms, alkenyl of 2–7 carbon atoms, alkynyl of 2–7 carbon atoms, cycloalkyl of 3–8 carbon atoms, aryl, Het, arylalkyl having 1–6 carbon atoms in the alkyl chain, Het-alkyl having 1–6 carbon atoms in the alkyl chain, halogen, cyano, nitro, hydroxy, alkoxy of 1–6 carbon atoms, aryloxy, arylalkyloxy having 1–6 carbon atoms in the alkyl chain, alkylthio 1–6 carbon atoms, arylthio, arylamino, Het-amino, arylalkylamino of 1–6 carbons in the alkyl chain, Het-alkylamino having 1–6 carbon atoms in the alkyl chain, hydroxyamino, —NHCOR$_7$, —NHSO$_2$R$_7$, —NHP(O)(R$_7$)$_2$, —COR$_8$, —SO$_2$R$_8$, —NR$_8$R$_8$, carboxy, alkylcarbonyl of 2–7 carbon atoms, formylalkyl of 2–7 carbon atoms, phosphoryl, alkoxycarbonylalkyl of 3–13 carbon atoms, carboxyalkyl of 2–7 carbon atoms, alkylcarbonylalkyl of 2–13 carbon atoms, arylcarbonylalkyl having 1–6 carbon atoms in the alkyl chain, Het-carbonylalkyl having 1–6 carbon atoms in the alkyl chain, aminocarbonylalkyl of 2–7 carbon atoms, alkylaminocarbonylalkyl of 3–13 carbon atoms, arylaminocarbonylalkyl having 1–6 carbon atoms in the alkyl chain, Het-aminocarbonylalkyl having 1–6 carbon atoms in the alkyl chain, aminosulfonylalkyl of 1–6 carbon atoms, alkylsulfonylalkyl of 2–12 carbon atoms, arylsulfonylalkyl having 1–6 carbon atoms in the alkyl chain, alkylaminosulfonylalkyl of 2–12 carbon atoms, arylaminosulfonylalkyl of 1–6 carbon atoms, Het-aminosulfonylalkyl of 1–6 carbon atoms, phosphonylalkyl of 1–6 carbon atoms, or phosphorylalkyl of 1–6 carbon atoms; or $R_5$ and $R_6$ may be alkylene groups that are taken together to form a 3–8 membered cycloalkyl ring when $R_5$ and $R_6$ are attached to a common carbon atom;

$R_7$ is hydrogen, trifluoromethyl, alkyl of 1–6 carbon atoms, cycloalkyl of 3–8 carbon atoms, alkenyl of 2–7 carbon atoms, alkynyl of 2–7 carbon atoms, aryl, alkoxy of 1–6 carbon atoms, —NR$_8$R$_9$, or —NH$_9$(CH$_2$)$_p$—R$_8$ $R_8$ is hydrogen, alkoxy of 1–6 carbon atoms, alkyl of 1–6 carbon atoms, hydroxy, aryl substituted with $R_5$ and $R_6$, arylalkoxy having 1–6 carbon atoms in the alkyl chain, —CR$_3$R$_5$R$_6$, —(CH$_2$)$_p$—COR$_9$, or —(CH$_2$)$_p$—R$_9$;

$R_9$ is hydrogen, hydroxy, alkyl of 1–6 carbon atoms, cycloalkyl of 3–8 carbon atoms, alkoxy of 1–6 carbon atoms, aryl substituted with $R_5$ and $R_6$, Het substituted with $R_5$ and $R_6$, arylalkoxy having 1–6 carbon atoms in the alkyl chain, or —NR$_{10}$R$_{10}$;

$R_{10}$ is hydrogen, alkyl of 1–6 carbon atoms, alkoxycarbonyl of 2–7 carbon atoms, hydroxy, aryl substituted with $R_5$ and $R_6$, or Het substituted with $R_5$ and $R_6$;

Het is a monocyclic or bicyclic heterocycle of 5–10 ring atoms, having 1–4 heteroatoms selected from oxygen, nitrogen, and sulfur; wherein the heterocycle may be saturated, unsaturated, or partially unsaturated; and may be optionally fused to a phenyl ring;

m is 1–3;

n is 1–3;

p is 0–6;

or a pharmaceutically acceptable salt thereof, which are selective agonists at human $\beta_3$ adrenergic receptors and are useful as antidiabetic, antihyperglycemic, and antiobesity agents.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids when a compound of this invention contains a basic moiety. Salts may also be formed from organic and inorganic bases, such as alkali metal salts (for example, sodium, lithium, or potassium) alkaline earth metal salts, ammonium salts, alkylammonium salts containing 1–6 carbon atoms or dialkylammonium salts containing 1–6 carbon atoms in each alkyl group, and trialkylammonium salts containing 1–6 carbon atoms in each alkyl group, when a compound of this invention contains an acidic moiety.

Alkyl includes both straight chain as well as branched moieties. By definition alkyl also includes alkyl moieties which are optionally mono- or poly substituted with groups such as halogen, hydroxy, cyano, alkoxy, aryloxy, arylalkyl, alkylthio, arylthio, amino, alkylamino, and dialkylamino. Halogen means bromine, chlorine, fluorine, and iodine. Where a substituent contains one or more moieties which have the same designation (i.e., —NR$_8$R$_8$), each of the moieties can be the same or different.

Preferred aryl moieties include phenyl or naphthyl. Preferred Het moieties include: (a) 6-membered saturated, partially unsaturated, or unsaturated heterocycles containing 1–2 nitrogens, optionally fused to a phenyl ring; (b) 5-membered saturated, partially saturated, or unsaturated heterocycles containing 1–3 nitrogen, oxygen, or sulfur atoms, optionally fused to a phenyl ring; (c) saturated, partially unsaturated, or unsaturated bicyclic heterocycles containing 1–4 nitrogen, oxygen, or sulfur atoms; (d) carbazole, dibenzofuran, and dibenzothiophene. In the Het of categories (a), (b), and (c), ring carbon atoms may be carbonyl moieties, where the ring does not contain a double bond in that position (for example, thiazolidine-2,4-dione).

More preferred Het rings include pyridine, pyrimidine, furan, imidazolyl, thiazole, oxazole, isoxazole, pyrazole, triazole, tetrazole, carbazole, pyrrole, thiophene, imidazole, imidazol-2-one, imidazole-2-thione, imidazolidine-2,4-dione, pyrazoline, triazole, tetrazole, oxazolone, oxadiazole, imidazolone, thiazole, thiazolone, thiadiazole, thiadiazolone, thiazoladine-2,4-dione, pyridine, pyrimidine, piperazine, pyrazine, pyrrolidine, piperidine, morpholine, benzofuran, dibenzofuran, dibenzothiophene, isobenzofuran, indole, isoindole, benzothiophene, 1,3-dihydrobenzoimidazol-2-one, benzo[1,2,5]thiadoazole, 2-oxo-2,3-dihydro-1H-benzoimidazole, quinoline, and isoquinoline. Particularly preferred Het include pyrrolidine, piperazine, piperidine, thiazole, imidazolidine-2,4-dione, carbazole, and 2-oxo-2,3-dihydro-1H-benzoimidazole. It is understood that Het do not contain heteroatoms in arrangements which would make them inherently unstable. For example, the term Het does not include ring systems containing O—O bonds in the ring backbone.

The compounds of the present invention contain at least one asymmetric center. Additional asymmetric centers may exist on the molecule depending upon the structure of the substituents on the molecule. The compounds may be prepared as a racemic mixture and can be used as such, or may be resolved into the . In addition to covering the racemic compounds, this invention also covers all individual isomers, enantiomers, diasteromers or mixtures thereof, regardless of whether the structural representations of the compounds indicate such stereochemistry.

Preferred compounds of Formula I are those in which $R_2$ is hydrogen;

$R_4$ is alkyl of 1–6 carbon atoms, alkenyl of 2–7 carbon atoms, alkynyl of 2–7 carbon atoms, cycloalkyl of 3–8 carbon atoms, aryl substituted with $R_4$ and $R_5$, Het substituted with $R_5$ and $R_6$, —$NR_8R_8$, or —$CR_3R_5R_6$;

$R_3$, $R_5$, and $R_6$ are each, independently, hydrogen, alkyl of 1–6 carbon atoms, alkenyl of 2–7 carbon atoms, alkynyl of 2–7 carbon atoms, halogen, hydroxy, alkoxy of 1–6 carbon atoms, arylalkoxy having 1–6 carbon atoms in the alkyl chain, hydroxy, arylalkyl having 1–6 carbon atoms in the alkyl chain, Het-alkyl having 1–6 carbon atoms in the alkyl chain, —$NHCOR_7$, —$NHSO_2R_7$, —$NR_8R_8$, —$COR_8$, formylalkyl of 2–7 carbon atoms, or alkoxycarbonylalkyl of 3–13 carbon atoms, or $R_5$ and $R_6$ may be alkylene groups that are taken together to form a 3–8 membered cycloalkyl ring when $R_5$ and $R_6$ are attached to a common carbon atom;

Het is (a) a 6-membered saturated, partially unsaturated, or unsaturated heterocycle containing 1–2 nitrogens, optionally fused to a phenyl ring; (b) a 5-membered saturated, partially saturated, or unsaturated heterocycle containing 1–3 nitrogen, oxygen, or sulfur atoms, optionally fused to a phenyl ring; (c) a saturated, partially unsaturated, or unsaturated bicyclic heterocycle containing 1–4 nitrogen, oxygen, or sulfur atoms; (d) carbazole, dibenzofuran, and dibenzothiophene; wherein one or more of the ring carbon atoms of Het as described in (a), (b), or (c) may be a carbonyl moiety, where the ring does not contain a double bond in the position corresponding to that carbon atom;

or a pharmaceutically acceptable salt thereof.

More preferred compounds of Formula I are those in which

Y is $OCH_2$ or a bond;

$R_2$ is hydrogen;

$R_4$ is aryl substituted with $R_4$ and $R_5$, Het substituted with $R_5$ and $R_6$, —$NR_8R_8$, or —$CR_3R_5R_6$;

$R_3$, $R_5$, and $R_6$ are each, independently, hydrogen, alkyl of 1–6 carbon atoms, alkenyl of 2–7 carbon atoms, alkynyl of 2–7 carbon atoms, halogen, hydroxy, alkoxy of 1–6 carbon atoms, arylalkoxy having 1–6 carbon atoms in the alkyl chain, hydroxy, —$NHSO_2R_7$, —$NR_8R_8$, —$COR_8$, formylalkyl of 2–7 carbon atoms, or alkoxycarbonylalkyl of 3–13 carbon atoms, or $R_5$ and $R_6$ may be alkylene groups that are taken together to form a 3–8 membered cycloalkyl ring when $R_5$ and $R_6$ are attached to a common carbon atom;

Het is pyridine, pyrimidine, furan, imidazolyl, thiazole, oxazole, isoxazole, pyrazole, triazole, tetrazole, carbazole, pyrrole, thiophene, imidazole, imidazol-2-one, imidazole-2-thione, imidazolidine-2,4-dione, pyrazoline, triazole, tetrazole, oxazolone, oxadiazole, imidazolone, thiazole, thiazolone, thiadiazole, thiadiazolone, thiazoladine-2,4-dione, pyridine, pyrimidine, piperazine, pyrazine, pyrrolidine, piperidine, morpholine, benzofuran, dibenzofuran, dibenzothiophene, isobenzofuran, indole, isoindole, benzothiophene, 1,3,-dihydrobenzoimidazol-2-one, benzo[1,2,5]thiadoazole, 2-oxo-2,3-dihydro-1H-benzoimidazole, quinoline, or isoquinoline;

or a pharmaceutically acceptable salt thereof.

Specifically preferred compounds of this invention are:

a) N-Benzyl-N-(3,4-dimethoxy-phenyl)-4-{4-[2-hydroxy-3-(2-oxo-2,3-dihydro-1H-benzoimidazol-4-yloxy)-propylamino]-piperidin-1-yl}-benzenesulfonamide;

b) N-Benzyl-N-butyl-4-{4-[(2S)-2-hydroxy-3-(2-oxo-2,3-dihydro-1H-benzoimidazol-4-yloxy)-propylamino]-piperidin-1-yl}-benzenesulfonamide;

c) N-Benzyl-N-butyl-4-{4-[2-hydroxy-2-(4-hydroxy-3-methanesulfonylamino-phenyl)-ethylamino]-piperidin-1-yl}-benzenesulfonamide;

d) N-Benzyl-4-{4-[2-hydroxy-3-(2-oxo-2,3-dihydro-1H-benzoimidazol-4-yloxy)-propylamino]-piperidin-1-yl}-benzenesulfonamide;

e) N-Benzyl-4-{4-[2-hydroxy-2-(4-hydroxy-3-methanesulfonylamino-phenyl)-ethylamino]-piperidin-1-yl}-benzenesulfonamide;

f) N-Benzyl-4-{4-[(2S)-2-hydroxy-3-(4-hydroxy-phenoxy)-propylamino]-piperidin-1-yl}-benzenesulfonamide;

g) N-(3,4-Dimethoxy-phenyl)-4-{4-[(2S)-2-hydroxy-3-(2-oxo-2,3-dihydro-1H-benzoimidazol-4-yloxy)-propylamino]-piperidin-1-yl}-benzenesulfonamide;

h) N-(3,4-Dimethoxy-phenyl)-4-{4-[2-hydroxy-2-(4-hydroxy-3-methanesulfonylamino-phenyl)-ethylamino]-piperidin-1-yl}-benzenesulfonamide;

i) 4-{4-[(2S)-3-(4-Benzyloxy-phenoxy)-2-hydroxy-propylamino]-piperidin-1-;

j) yl}-N-(3,4-dimethoxy-phenyl)-benzenesulfonamide;

k) 4-{4-[(2S)-3-(9H-Carbazol-4-yloxy)-2-hydroxy-propylamino]-piperidin-1-yl}-N-(3,4-dimethoxy-phenyl)-benzenesulfonamide;

l) N-(3,4-Dimethoxy-phenyl)-4-{4-[(2S)-2-hydroxy-3-(4-hydroxy-phenoxy)-propylamino]-piperidin-1-yl}-benzenesulfonamide;

m) N-Butyl-4-{4-[(2S)-2-hydroxy-3-(2-oxo-2,3-dihydro-1H-benzoimidazol-4-yloxy)-propylamino]-piperidin-1-yl}-benzenesulfonamide;

n) N-Butyl-4-{4-[(2S)-3-(9H-carbazol-4-yloxy)-2-hydroxy-propylamino]piperidin-1-yl}-benzenesulfonamide;

o) N-Butyl-4-{4-[(2R)-2-hydroxy-2-(4-hydroxy-3-methanesulfonylamino-phenyl)-ethylamino]-piperidin-1-yl}-benzenesulfonamide;

p) 1-(4-{4-[2-Hydroxy-2-(4-hydroxy-3-methanesulfonylamino-phenyl)ethylamino]-piperidin-1-yl}-benzenesulfonyl)-pyrrolidine-2-carboxylic acid isopropyl ester;

q) 1-(4-{4-[2-Hydroxy-3-(2-oxo-2,3-dihydro-1H-benzoimidazol-4-yloxy)propylamino]-piperidin-1-yl}-benzenesulfonyl)-pyrrolidine-2-carboxylic acid isopropyl ester;

r) 1-(4-{4-[(2S)-2-Hydroxy-3-(2-oxo-2,3-dihydro-1H-benzoimidazol-4-yloxy)propylamino]-piperidin-1-yl}-benzenesulfonyl)-pyrrolidine-2-carboxylic acid methylamide;

s) 1-(4-{4-[2-Hydroxy-2-(4-hydroxy-3-methanesulfonylamino-phenyl)ethylamino]-piperidin-1-yl}-benzenesulfonyl)-pyrrolidine-2-carboxylic acid;

t) [Butyl-(4-{4-[(2R)-2-hydroxy-2-(4-hydroxy-3-methanesulfonylaminophenyl)-ethylamino]piperidin-1-yl}-benzenesulfonyl)-amino]-acetic acid benzyl ester;

u) [Butyl-(4-{4-[(2R)-2-hydroxy-2-(4-hydroxy-3-methanesulfonylaminophenyl)-ethylamino]-piperidin-1-yl}-benzenesulfonyl)-amino]-acetic acid;

v) (2R)-1-(4-{4-[(2R)-2-Hydroxy-2-(4-hydroxy-3-methanesulfonylamino-phenyl)ethylamino]-piperidin-1-yl}-benzenesulfonyl)-pyrrolidine-2-carboxylic acid benzyl ester;

w) (2S)-1-(4-{4-[(2R)-2-Hydroxy-2-(4-hydroxy-3-methanesulfonylamino-phenyl)ethylamino]-piperidin-1-yl}-benzenesulfonyl)-pyrrolidine-2-carboxylic acid benzyl ester;

x) [Butyl-(4-{4-[(2R)-2-hydroxy-2-(4-hydroxy-3-methanesulfonylamino-phenyl)-ethylamino]-piperidin-1-yl}-benzenesulfonyl)-amino]-acetic acid ethyl ester-1-yl}-phenyl)-amino]-acetic acid;

y) N-(2-Hydroxyethyl)-4-{4-[(2R)-2-hydroxy-2-(4-hydroxy-3-methanesulfonylamino-phenyl)-ethylamino]-piperidin-1-yl}-benzenesulfonamide;

z) [(4-{4-[(2R)-2-Hydroxy-2-(4-hydroxy-3-methanesulfonylamino-phenyl)-ethylamino]-piperidin-1-yl}-benzenesulfonyl)-methyl-amino]-acetic acid ethyl ester;

aa) N-Cyclopropylmethyl-4-{4-[(2R)-2-hydroxy-2-(4-hydroxy-3-methanesulfonylamino-phenyl)-ethylamino]-piperidin-1-yl}-benzenesulfonamide;

bb) 4-{4-[(2R)-2-Hydroxy-2-(4-hydroxy-3-methanesulfonylamino-phenyl)-ethylamino]-piperidin-1-yl}-N-isobutyl-benzenesulfonamide;

cc) [Cyclopropylmethyl-(4-{4-[(2R)-2-hydroxy-2-(4-hydroxy-3-methanesulfonylamino-phenyl)-ethylamino]-piperidin-1-yl}-benzenesulfonyl)-amino]-acetic acid ethyl ester;

dd) 4-{4-[(2R)-2-Hydroxy-2-(4-hydroxy-3-methanesulfonylamino-phenyl)-ethylamino]-piperidin-1-yl}-N-isopropyl-benzenesulfonamide;

ee) 1-(4-{4-[(2R)-2-Hydroxy-2-(4-hydroxy-3-methanesulfonylamino-phenyl)-ethylamino]-piperidin-1-yl}-benzenesulfonyl)-pyrrolidine-(2R)-2-carboxylic acid ethyl ester;

ff) [Cyclopropylmethyl-(4-{4-[(2R)-2-hydroxy-2-(4-hydroxy-3-methanesulfonylamino-phenyl)-ethylamino]-piperidin-1-yl}-benzenesulfonyl)-amino]-acetic acid;

gg) [(4-{4-[(2R)-2-Hydroxy-2-(4-hydroxy-3-methanesulfonylamino-phenyl)-ethylamino]-piperidin-1-yl}-benzenesulfonyl)-isobutyl-amino]-acetic acid ethyl ester;

hh) [(4-{4-[(2R)-2-Hydroxy-2-(4-hydroxy-3-methanesulfonylamino-phenyl)-ethylamino]-piperidin-1-yl}-benzenesulfonyl)-methyl-amino]-acetic acid;

ii) [(4-{4-[(2R)-2-Hydroxy-2-(4-hydroxy-3-methanesulfonylamino-phenyl)-ethylamino]-piperidin-1-yl}-benzenesulfonyl)-isobutyl-amino]-acetic acid;

jj) 1-(4-{4-[(2R)-2-Hydroxy-2-(4-hydroxy-3-methanesulfonylamino-phenyl)-ethylamino]-piperidin-1-yl}-benzenesulfonyl)-pyrrolidine-(2R)-2-carboxylic acid;

kk) ethyl(2S)-1-[(4-{4-[((2R)-2-hydroxy-2-{4-hydroxy-3-[(methylsulfonyl)amino]phenyl}ethyl)amino]-1-piperidinyl}phenyl)sulfonyl]-2-pyrrolidinecarboxylate;

ll) ethyl(2S)-2-{[(4-{4-[((2R)-2-hydroxy-2-{4-hydroxy-3-[(methylsulfonyl)amino]phenyl}ethyl)amino]-1-piperidinyl}phenyl)sulfonyl]amino}-4-methylpentanoate;

mm) ethyl(2S)-2-{[(4-{4-[((2R)-2-hydroxy-2-{4-hydroxy-3-[(methylsulfonyl)amino]phenyl}ethyl)amino]-1-piperidinyl}phenyl)sulfonyl]amino}-3-methylbutanoate;

nn) (2S)-1-[(4-{4-[((2R)-2-hydroxy-2-{4-hydroxy-3-[(methylsulfonyl)amino]phenyl}ethyl)amino]-1-piperidinyl}phenyl)sulfonyl]-2-pyrrolidinecarboxylic acid;

oo) ethyl 1-{[(4-{4-[((2R)-2-hydroxy-2-{4-hydroxy-3-nyl}phenyl)sulfonyl]amino}cyclopentanecarboxylate;

pp) N-{2-hydroxy-5-[(1R)-1-hydroxy-2-({1-[4-(1-pyrrolidinylsulfonyl)phenyl]-4-idinylsulfonyl)phenyl]-4-piperidinyl}amino)ethyl]phenyl}methanesulfonamide;

qq) N-{2-hydroxy-5-[(1R)-1-hydroxy-2-({1-[4-(1-piperidinylsulfonyl)phenyl]-4-idinylsulfonyl)phenyl]-4-piperidinyl}amino)ethyl]phenyl}methanesulfonamide;

rr) Ethyl 1-{[(4-{4-[((2R)-2-hydroxy-2-{4-hydroxy-3-inyl}phenyl)sulfonyl]amino}cyclohexanecarboxylate;

ss) Ethyl [[(4-{4-[((2R)-2-hydroxy-2-{4-hydroxy-3-idinyl}phenyl)sulfonyl](isopropyl)amino]acetate;

tt) N-[2-Hydroxy-5-(1-hydroxy-2-{1-[4-(toluene-4-sulfonyl)-phenyl]-piperidin-4-ylamino}-ethyl)-phenyl]-methanesulfonamide;

uu) 4-((2S)-2-Hydroxy-3-{1-[4-(toluene-4-sulfonyl)-phenyl]-piperidin-4-ylamino}-propoxy)-1,3-dihydro-benzoimidazol-2-one;

vv) 2-(2-butynyl)-2-[(4-{4-[((2R)-2-hydroxy-2-{4-hydroxy-3-[(methylsulfonyl)amino]-phenyl}ethyl)amino]-1-piperidinyl}phenyl)sulfonyl]-4-hexynoicacid tert-butyl ester;

ww) 2-(2-butynyl)-2-[(4-{4-[((2R)-2-hydroxy-2-{4-hydroxy-3-[(methylsulfonyl)amino]-phenyl}ethyl)amino]-1-piperidinyl}phenyl)sulfonyl]-4-hexynoic acid;

xx) 1-(4-{4-[(2S)-2-Hydroxy-3-(2-oxo-2,3-dihydro-1H-benzoimidazol-4-yloxy)propylamino]-piperidin-1-yl}-benzenesulfonyl)-imidazolidine-2,4-dione;

yy) N-[5-((1R)-2-{1-[4-(2,4-Dioxo-imidazolidine-1-sulfonyl)-phenyl]piperidin-4-ylamino}-1-hydroxy-ethyl)-2-hydroxy-phenyl]-methanesulfonamide;

zz) 1-(4-{[((2S)-2-Hydroxy-2-(2-trifluoromethyl-thiazol-4-yl)-ethylamino]-piperidin-1-yl}-benzenesulfonyl)-imidazolidine-2,4-dione;

aaa) tert-Butyl 2-{[(4-{4-[((2R)-2-hydroxy-2-{4-hydroxy-3-[(methylsulfonyl)amino]phenyl}ethyl)amino]-1-piperidinyl}phenyl)sulfonyl]amino}acetate;

bbb) 2-}[(4-{4-[((2R)-2-hydroxy-2-{4-hydroxy-3-[(methylsulfonyl)amino]phenyl}ethyl)amino]-1-piperidinyl}phenyl)sulfonyl]amino}acetic acid;

ccc) tert-Butyl 2-{[2-(tert-butoxy)-2-oxoethyl][(4-{4-[((2R)-2-hydroxy-2-{4-hydroxy-3-[(methylsulfonyl)amino]phenyl}ethyl)amino]-1-piperidinyl}phenyl)sulfonyl]amino}acetate;

ddd) 2-{(Carboxymethyl)[(4-{4-[((2R)-2-hydroxy-2-{4-hydroxy-3-[(methylsulfonyl)amino]phenyl}ethyl)amino]-1-piperidinyl}phenyl)sulfonyl]amino}acetic acid;

eee) Ethyl 2-{[(4-[4-[((2R)-2-hydroxy-2-{4-hydroxy-3-[(methylsulfonyl)amino]phenyl}ethyl)amino]-1-piperidinyl}phenyl)sulfonyl]amino}acetate;

fff) Methyl 2-{[(4-{4-[((2R)-2-hydroxy-2-{4-hydroxy-3-[(methylsulfonyl)amino]phenyl}ethyl)amino]-1-piperidinyl}phenyl)sulfonyl]amino}acetate;

ggg) Ethyl 2-{[(4-{4-[((2R)-2-hydroxy-2-{4-hydroxy-3-[(methylsulfonyl)amino]phenyl}ethyl)amino]piperidin-1-yl}phenyl)sulfonyl]amino}acetylcarbamate;

hhh) tert-Butyl [[(4-{4-[((2R)-2-hydroxy-3-[(methylsulfonyl)amino]phenyl}ethyl)amino]piperidin-1-yl}phenyl)sulfonyl](methoxycarbonyl)amino]acetate;

iii) [[(4-{4-[((2R)-2-Hydroxy-2-{4-hydroxy-3-[(methylsulfonyl)amino]phenyl}ethyl)amino]piperidin-1-yl}phenyl)sulfonyl](methoxycarbonyl)amino]acetic acid;

jjj) Ethyl {(2,5-difluorobenzyl)[(4-{4-[((2R)-2-hydroxy-2-{4-hydroxy-3-[(methylsulfonyl)amino]phenyl}ethyl)amino]piperidin-1-yl}phenyl)sulfonyl]amino}acetate;

kkk) 1-[4-({[(Butylamino)carbonyl]amino}sulfonyl)phenyl]-4-[((2 R)-2-hydroxy-2-{4-hydroxy-3-[(methylsulfonyl)amino]phenyl}ethyl)amino]piperidine;

lll) 2-{(2,5-Difluorobenzyl)[(4-{4-[((2R)-2-hydroxy-2-{4-hydroxy-3-[(methylsulfonyl)amino]phenyl}ethyl)amino]-1-piperidinyl}phenyl)sulfonyl]amino}acetic acid;

mmm) Ethyl {4-[(4-{4-[((2R)-2-hydroxy-2-{4-hydroxy-3-[(methylsulfonyl)amino]phenyl}ethyl)amino]piperidin-1-yl}phenyl)sulfonyl]piperazin-1-yl}acetate;

nnn) {4-[(4-{4-[((2R)-2-hydroxy-2-{4-hydroxy-3-[(methylsulfonyl)amino]-phenyl}ethyl)amino]piperidin-1-yl}phenyl)sulfonyl]piperazin-1-yl}acetic acid;

ooo) N-(2-Hydroxy-5-{(1R)-1-hydroxy-2-[(1-{4-[(4-methylpiperazin-1-yl)sulfonyl]phenyl}piperidin-4-yl)amino]ethyl}phenyl)methanesulfonamide;

ppp) tert-Butyl {(2,5-difluorobenzyl)[(4-{4-[((2R)-2-hydroxy-2-{4-hydroxy-3-[(methylsulfonyl)amino]phenyl}ethyl)amino]piperidin-1-yl}phenyl)sulfonyl]amino}acetate;

or a pharmaceutically acceptable salt thereof; and

{4-[(4-{4-[((2R)-2-hydroxy-2-{4-hydroxy-3-[(methylsulfonyl)amino]-phenyl}ethyl)amino]piperidin-1-yl}phenyl)sulfonyl]piperazin-1-yl}acetic acid, sodium salt.

The compounds of this invention were be prepared according to the following schemes from commercially available starting materials or starting materials which can be prepared using literature procedures. These schemes show the preparation of representative compounds of this invention.

Scheme 1

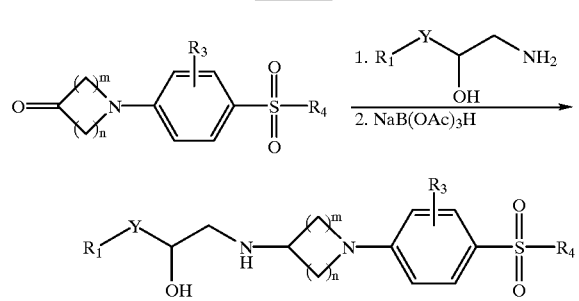

Scheme 2

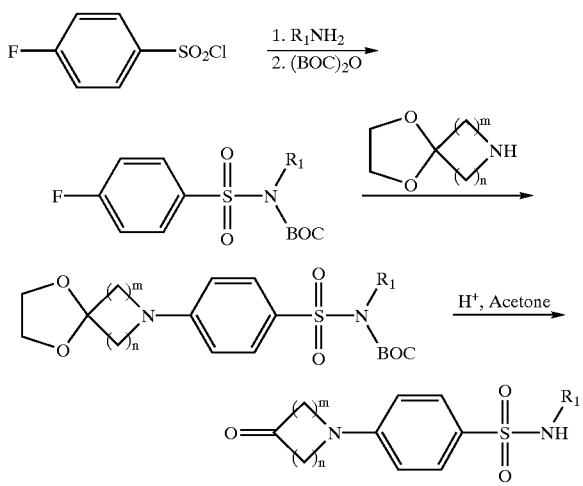

Scheme 3

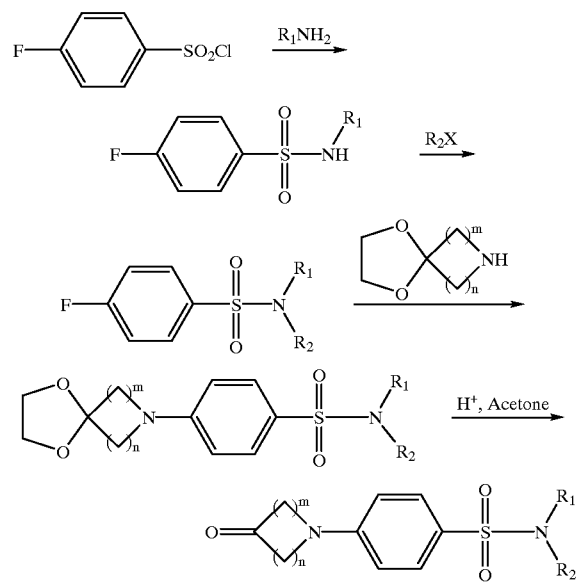

Scheme 4

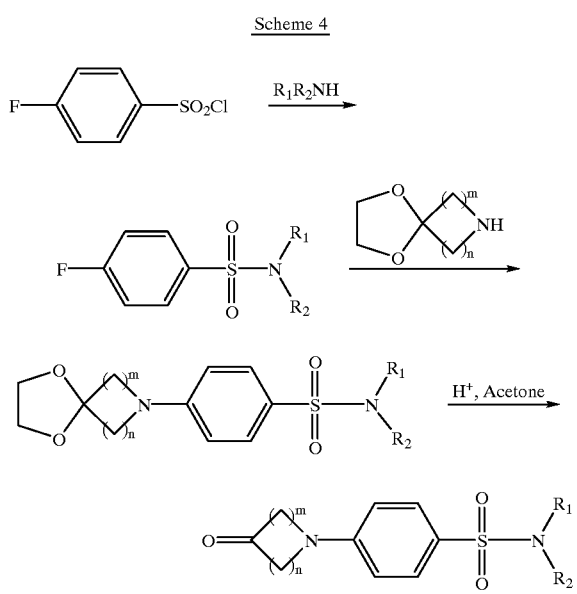

Scheme 5

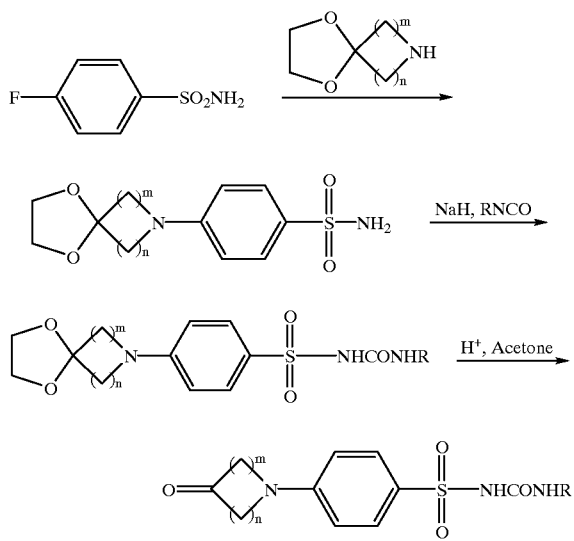

Scheme 6

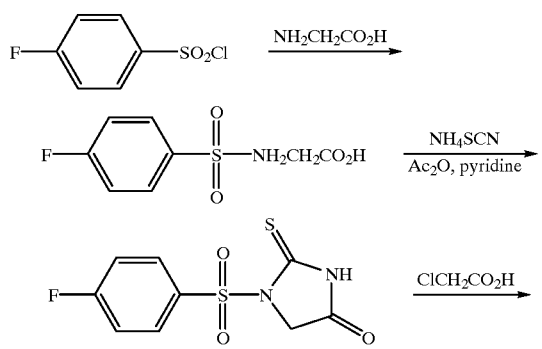

-continued

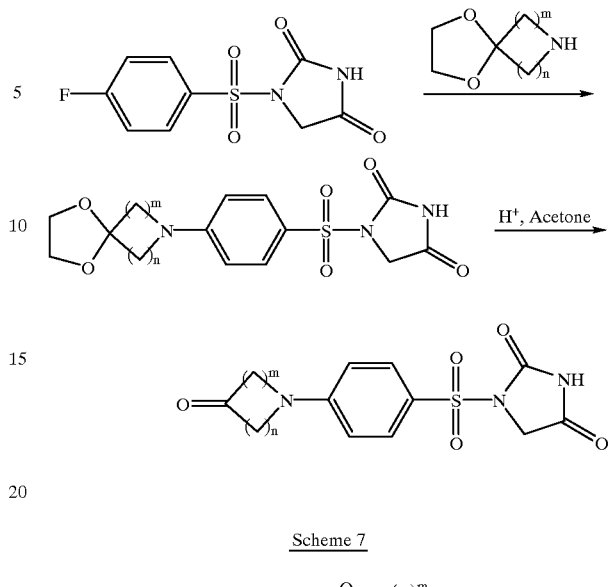

Scheme 7

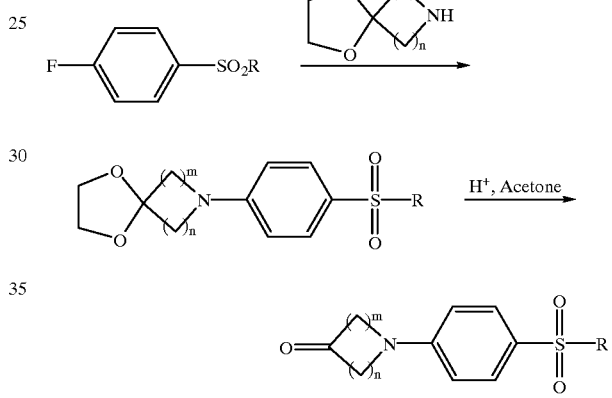

In general, as shown in Scheme 1, compounds of the present invention are prepared by reductive amination of N-(4-sulfonylaryl)-substituted oxo-cyclylamines with the appropriate aryl-substituted ethanolamines. Various oxo-cycylamine derivatives can be prepared according to one of the synthetic Schemes 2 to 7.

Many of the aryloxypropanolamines and arylethanolamines used in Scheme 1 are commerically available or readily prepared by known methods [e.g., 1. A. Guy, Synthesis, 1992, 821; 2. A. A. Asselin, J. Med. Chem., 1986, 1009; 3. M. S. Berridge et al., Nucl. Med. Biol., 19, 1992, 563; 4. C. D. Jesudason, et al., EP0764640; 5. EP0659737.]. In one method (Scheme 8), equimolar amounts of a substituted phenol and (2S) or (2R)-glycidyl 3-nitrobenzenesulfonate are dissolved in an organic solvent such as acetone or dimethylformamide and treated with a base such as sodium hydride or potassium carbonate for 0.5 to 24 hours at temperatures of 20 to 100° C. to provide the corresponding aryloxyoxiranes. The aryloxyoxiranes are converted to the ethanolamines by regioselective ring opening of the oxirane with lithium azide in a solvent such as hexamethylphosphoramide, followed by reduction with triphenylphosphine or hydrogenation with 10% Pd/C as catalyst. Alternatively, the aryloxyoxiranes can be converted to the ethanolamines by regioselective ring opening of the oxirane with dibenzylamine, followed by hydrogenation with 10% Pd/C as catalyst.

Scheme 8

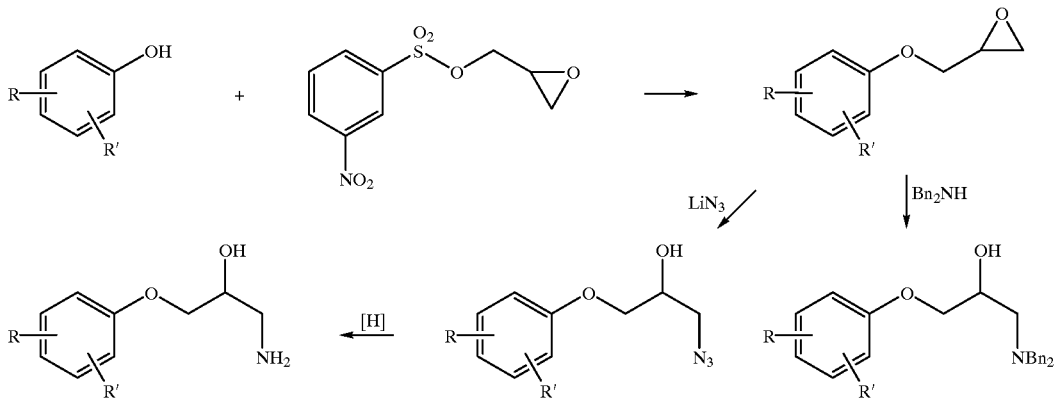

The arylethanolamines used in Scheme 1 can be prepared according to the methods shown in Scheme 9. Arylmethylketones are converted to the corresponding α-haloketones using known methods [J. March, Advanced Organic Chemistry, 3rd Ed., John Wiley and Sons, New York:1985, p529 and references cited therein]. The haloketones are reduced to the corresponding alcohol which can be protected as the triethylsilyl ether, or converted directly to the ethanolamine by treatment with ammonia or sodium azide followed by reduction. Treatment of the halo silyl ether with benzylamine followed by desilylation and hydrogenation also gives the corresponding arylethanolamine.

Scheme 9

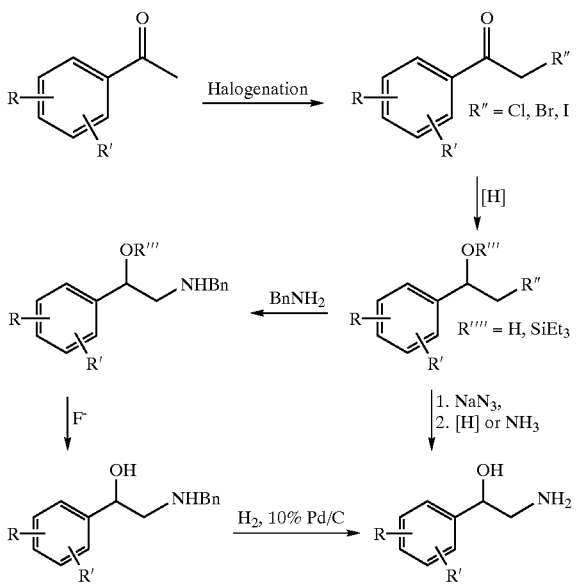

The compounds of this invention are useful in treating metabolic disorders related to insulin resistance or hyperglycemia, typically associated with obesity or glucose intolerance. The compounds of this invention are therefore, particularly useful in the treatment or inhibition of type II diabetes. The compounds of this invention are also useful in modulating glucose levels in disorders such as type I diabetes.

The ability of compounds of this invention to treat or inhibit disorders related to insulin resistance or hyperglycemia was established with representative compounds of this invention in the following standard pharmacological test procedures, which measured the binding selectivity to the $\beta_1$, $\beta_2$, and $\beta_3$ adrenergic receptors. Binding to the receptors was measured in Chinese Hamster ovary (CHO) cells that were transfected with adrenergic receptors. The following briefly summarizes the procedures used and results obtained.

Transfection of CHO cells with $\beta_1$ and $\beta_2$ adrenergic receptors: CHO cells were transfected with human $\beta_1$- or $\beta_2$-adrenergic receptors as described in Tate, K. M., Eur. J. Biochem., 196:357–361 (1991).

Cloning of Human $\beta_3$-AR Genomic DNA: cDNA was constructed by ligating four polymerase chain reaction (PCR) products using the following primers: an ATG-NarI fragment, sense primer 5'-CTTCCCTACCGCCCCACGCGCGATC3' and anti-sense primer 5'CTGGCGCCCAACGGCCAGTGGC-CAGTC3'; a NarI-AccI fragment, 5'TTGGCGCTGATGGC-CACTGGCCGTTTG3' as sense and 5'GCGCGTAGACGAAGAGCATCACGAG3' as anti-sense primer; an AccI-StyI fragment, sense primer 5'CTCGTGAT-GCTCTTCGTCTCACGCGC3' and anti-sense primer 5'GTGAAGGTGCCCATGATGAGACCCAAGG3' and a StyI-TAG fragment, with sense primer 5'CCCTGTGCAC-CTTGGGTCTCATCATGG3' and anti-sense primer 5'CCTCTGCCCCGGTTACCTACCC3'. The corresponding primer sequences are described in Mantzoros, C. S., et.al., Diabetes 45: 909–914 (1996). The four fragments are ligated into a pUC 18 plasmid (Gibco-BRL) and sequenced. Full length $\beta_3$ AR clones (402 amino acids) containing the last 6 amino acids of h$\beta_3$— AR are prepared with the $\beta_3$-βARpcDNA3from ATTC.

Binding Procedure: Clones expressing receptor levels of 70 to 110 fmoles/mg protein were used in the test procedures. CHO cells were grown in 24-well tissue culture plates in Dulbecco's Modified Eagle Media with 10% fetal bovine serum, MEM non-essential amino acids, Penicillin-Streptompycin and Geneticin. On the day of test procedure, growth medium was replaced with preincubation media (Dulbecco's Modified Eagle Media and incubated for 30 minutes at 37° C. Preincubation medium was replaced with 0.2 ml treatment medium containing DMEM media containing 250 μM IBMX (isobutyl-1-methylxantine) plus 1 mM ascorbic acid with test compound dissolved in DMSO. Test compounds were tested over a concentration range of $10^{-9}$ M to $10^{-5}$ M for $\beta_3$ cells and $10^{-8}$ to $10^{-4}$ M for $\beta_1$ and $\beta_2$ transfected cells. Isoproterenol ($10^{-5}$ M) was used as an internal standard for comparison of activity. Cells were incubated at 37° C. on a rocker for 30 min with the $\beta_3$ cells and 15 min for $\beta_1$ and $\beta_2$ cells. Incubation was stopped with the addition of 0.2N HCl and neutralized with 2.5N NaOH. The plates, containing the cells and neutralized media, were stored at −20 degrees celsius until ready to test for cAMP using the SPA test kit (Amersham).

Data Analysis and Results: Data collected from the SPA test procedure were analyzed as per cent of the maximal isoproterenol response at $10^{-5}$ M. Activity curves were plotted using the SAS statistical and graphics software. $EC_{50}$ values were generated for each compound and the maximal response (IA) developed for each compound is compared to the maximal response of isoprotenol at $10^{-5}$ M from the following formula:

IA=% activity compound/% activity isoproterenol

Table I shows the $EC_{50}$ and IA values for the representative compounds of this invention that were evaluated in this standard pharmacological test procedure that measured binding selectivity at that $\beta$-adrenergic receptors.

TABLE I

| Example | beta-3 $EC_{50}$ μM (IA) | beta-2 $EC_{50}$ μM (IA) | beta-1 $EC_{50}$ μM (IA) |
| --- | --- | --- | --- |
| 1 | 0.017 (0.92) | (0) | (0.09) |
| 2 | 0.094 (1.1) | (0.03) | (0.16) |
| 3 | 0.015 (1.1) | 0.31 (0.59) | 2.1 (0.66) |
| 4 | 0.021 (0.78) | (0) | (0.17) |
| 5 | 0.016 (0.98) | (0.07) | 2.2 (0.59) |
| 6 | 0.2 (0.76) | | |
| 7 | 0.02 (0.8) | (0.01) | 0.6 (0.15) |
| 8 | 0.016 (0.91) | 0.61 (0.28) | 3.6 (0.41) |
| 10 | 0.1 (0.45) | | |
| 11 | 0.33 (0.83) | | |
| 12 | 0.01 (1) | | |
| 13 | 0.05 (0.7) | | |
| 14 | 0.001 (1.3) | 0.17 (0.53) | 0.64 (1) |
| 15 | 0.001 (1) | 0.16 (0.37) | 13 (0.23) |
| 16 | 0.003 (0.86) | | |
| 17 | 0.028 (0.81) | | |
| 18 | 0.041 (0.99) | 1 (0.55) | (0.29) |
| 19 | 0.007 (1) | (0.2) | 0.79 (0.54) |
| 20 | 0.01 (1) | 10 (0.3) | 10 (0.4) |
| 21 | 0.001 (1) | 0.64 (0.82) | 0.06 (0.88) |
| 22 | 0.002 (1) | 0.04 (0.63) | 0.2 (1.08) |
| 23 | 0.016 (1) | 1.67 (0.89) | 1.32 (0.68) |
| 24 | 0.033 (0.88) | 1 (0.68) | 1 (0.35) |
| 25 | 0.052 (1) | 1.43 (0.37) | 1 (0.63) |
| 26 | 0.023 (0.98) | 0.27 (0.29) | 0.24 (0.41) |
| 27 | 0.002 (1) | 0.54 (0.29) | 0.42 (0.22) |
| 28 | 0.002 (0.94) | 6.6 (0.85) | (0.24) |
| 29 | 0.007 (1.3) | 2.9 (0.48) | 2.0 (0.57) |
| 30 | 0.004 (1.2) | 3.6 (0.36) | 9.8 (1.1) |
| 31 | 0.007 (1.2) | 12 (0.33) | 20 (0.96) |
| 32 | 0.004 (1) | 10 (0.57) | 6.7 (0.48) |
| 33 | 0.018 (1) | (0.15) | 25 (0.66) |
| 34 | 0.006 (1.1) | (0.14) | 10 (0.49) |
| 35 | 0.011 (1.1) | (0.04) | 49 (0.66) |
| 36 | 0.009 (1) | 0.72 (0.19) | 4.8 (0.85) |
| 37 | 0.016 (0.89) | 0.9 (0.42) | 5.6 (0.43) |
| 38 | 0.032 (1.1) | 0.38 (0.32) | 1.1 (0.5) |
| 39 | 0.03 (1) | (0.23) | 10 (0.42) |
| 40 | 0.004 (1.2) | 0.04 (0.31) | 1.9 (0.45) |
| 41 | 0.002 (1) | 2 (0.24) | 0.8 (0.58) |
| 42 | 0.001 (1) | 0.37 (0.35) | 1.32 (0.69) |
| 43 | 0.001 (1) | 0.09 (0.68) | 1.28 (0.58) |
| 44 | 0.003 (0.95) | 2 (0.43) | 12 (0.71) |
| 45 | 0.001 (1) | 0.7 (0.63) | 0.02 (0.74) |
| 46 | 0.009 (1.1) | | |
| 47 | 0.006 (0.93) | 3.2 (0.46) | 1 (0.47) |
| 48 | 0.59 (1) | 10 (0.54) | 10 (0.26) |
| 49 | 0.009 (0.96) | | |
| 50 | 0.01 (1) | 7 (0.35) | 2.6 (0.72) |

TABLE I-continued

| Example | beta-3 $EC_{50}$ μM (IA) | beta-2 $EC_{50}$ μM (IA) | beta-1 $EC_{50}$ μM (IA) |
| --- | --- | --- | --- |
| 52 | 0.006 (1) | 0.48 (0.65) | 0.96 (0.48) |
| 53 | 0.034 (1.2) | (0.23) | (0.24) |
| 54 | 0.014 (1.2) | 12 (0.42) | 2.3 (0.33) |
| 55 | 0.41 (0.94) | | |
| 56 | 0.014 (1) | 1.6 (0.27) | 9.5 (0.31) |
| 57 | 0.006 (0.85) | (0.18) | (0.18) |
| 58 | 0.011 (1) | 3.9 (0.31) | 3.6 (0.65) |
| 59 | 0.015 (0.98) | 12 (0.2) | 7.8 (0.52) |
| 60 | 0.021 (1.1) | 10 (0.21) | 10 (0.18) |
| 61 | 0.001 (1.1) | (0.2) | 1.9 (0.3) |
| 62 | 0.009 (1) | 5 (0.31) | 5 (0.32) |
| 63 | 0.005 (0.91) | (0.15) | 10 (0.88) |
| 64 | 0.004 (1.1) | 5.9 (0.22) | (0.11) |
| 65 | 0.16 (0.93) | 16 (0.67) | (0.23) |
| 66 | 0.025 (0.95) | (0.17) | 2.7 (0.44) |
| 67 | 0.005 (0.96) | (0.17) | 1 (0.48) |

Based on the results obtained in these standard pharmacological test procedures, representative compounds of this invention have been shown to be selective $\beta_3$ adrenergic receptor agonists and are therefore useful in treating metabolic disorders related to insulin resistance or hyperglycemia, typically associated with obesity or glucose intolerance. More particularly, the compounds of this invention useful in the treatment or inhibition of type II diabetes, and in modulating glucose levels in disorders such as type I diabetes. As used herein, the term modulating means maintaining glucose levels within clinically normal ranges.

As used in accordance with this invention, the term providing an effective amount means either directly administering such a compound of this invention, or administering a prodrug, derivative, or analog which will form an effective amount of the compound of this invention within the body.

It is understood that the effective dosage of the active compounds of this invention may vary depending upon the particular compound utilized, the mode of administration, the condition, and severity thereof, of the condition being treated, as well as the various physical factors related to the individual being treated. For treating treating metabolic disorders related to insulin resistance or hyperglycemia generally satisfactory results may be obtained when the compound of this invention are administered to the individual in need at a daily dosage of from about 0.1 mg to about 1 mg per kilogram of body weight, preferably administered in divided doses two to six times per day, or in a sustained release form. For most large mammals, the total daily dosage is from about 3.5 mg to about 140 mg. It is preferred that the administration of one or more of the compounds herein begin at a low dose and be increased until the desired effects are achieved.

Such doses may be administered in any manner useful in directing the active compounds herein to the recipient's bloodstream, including orally, via implants, parenterally (including intravenous, intraperitoneal and subcutaneous injections), rectally, intranasally, vaginally, and transdermally. For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Oral formulations containing the active compounds of this invention may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Oral formulations herein may utilize standard delay or time release formulations to alter the absorption of the active compound(s).

In some cases it may be desirable to administer the compounds directly to the airways in the form of an aerosol.

The compounds of this invention may also be administered parenterally or intraperitoneally. Solutions or suspensions of these active compounds as a free base or pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparation contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Suppository formulations may be made from traditional materials, including cocoa butter, with or without the addition of waxes to alter the suppository's melting point, and glycerin. Water soluble suppository bases, such as polyethylene glycols of various molecular weights, may also be used.

The compounds of the present invention also possess utility for increasing lean meat deposition and/or improving lean meat to fat ratio in edible animals, i.e. ungulate animals and poultry.

Animal feed compositions effective for increasing lean meat deposition and for improving lean meat to fat ratio in poultry, swine, sheep, goats, and cattle are generally prepared by mixing the compounds of the present invention with a sufficient amount of animal feed to provide from about 1 to 1000 ppm of the compound in the feed. Animal feed supplements can be prepared by admixing about 75% to 95% by weight of a compound of the present invention with about 5% to about 25% by weight of a suitable carrier or diluent. Carriers suitable for use to make up the feed supplement compositions include the following: alfalfa meal, soybean meal, cottonseed oil meal, linseed oil meal, sodium chloride, cornmeal, cane molasses, urea, bone meal, corncob meal and the like. The carrier promotes a uniform distribution of the active ingredients in the finished feed into which the supplement is blended. It thus performs an important function by ensuring proper distribution of the active ingredient throughout the feed. The supplement is used as a top dressing for the feed, it likewise helps to ensure uniformity of distribution of the active material across the top of the dressed feed.

The preferred medicated swine, cattle, sheep and goat feed generally contain from 0.01 to 400 grams of active ingredient per ton of feed, the optimum amount for these animals usually being about 50 to 300 grams per ton of feed. The preferred poultry and domestic pet feed usually contain about 0.01 to 400 grams and preferably 10 to 400 grams of active ingredient per ton of feed.

For parenteral administration the compounds of the present invention may be prepared in the form of a paste or a pellet and administered as an implant, usually under the skin of the head or ear of the animal in which increase in lean meat deposition and improvement in lean mean to fat ratio is sought. In general, parenteral administration involves injection of a sufficient amount of the compounds of the present invention to provide the animal with 0.001 to 100 mg/kg/day of body weight of the active ingredient. The preferred dosage for swine, cattle, sheep and goats is in the range of from 0.001 to 50 mg/kg/day of body weight of active ingredient; whereas, the preferred dose level for poultry and domestic pets is usually in the range of from 0.001 to 35 mg/kg/day of body weight.

Paste formulations can be prepared by dispersing the active compounds in a pharmaceutically acceptable oil such as peanut oil, sesame oil, corn oil or the like. Pellets containing an effective amount of the compounds of the present invention can be prepared by admixing the compounds of the present invention with a diluent such as carbowax, carnuba wax, and the like, and a lubricant, such as magnesium or calcium stearate, can be added to improve the pelleting process. It is, of course, recognized that more than one pellet may be administered to an animal to achieve the desired dose level which will provide the increase in lean meat deposition and improvement in lean meat to fat ratio desired. Moreover, it has been found that implants may also be made periodically during the animal treatment period in order to maintain the proper drug level in the animal's body. For the poultry and swine raisers, using the method of the present invention yields leaner animals.

Additionally, the compounds of this invention are useful in increasing the lean mass to fat ratio in domestic pets, for the pet owner or veterinarian who wishes to increase leanness and trim unwanted fat from pet animals, the present invention provides the means by which this can be accomplished.

The following procedures describe the preparation of representative aryloxypropanolamines and arylethanolamines used in the preparation of compounds of this invention.

(1R)-2-Amino-1-(3-chloro-phenyl)-ethanol:

Lithium azide (7.5 g, 150 mmol) was added to a solution of (1R)-1-(3-chloro-phenyl)oxirane (15.5 g, 100 mmol) in hexamethylphosphoramide (70 mL). After being stirred at room temperature for 16 hours the suspension was poured into ice-water and the mixture was extracted with diethyl ether. The combined extracts were dried (MgSO$_4$) and concentrated. The residue was dissolved in 550 mL of THF/H$_2$O (10:1) and triphenylphosphine (30 g, 114 mmol) was added. After overnight stirring at room temperature, the solvents were removed and the residue was purified by column chromatography on silica gel using triethylamine-methanolmethylene chloride (1:1:8) as the eluent to give the title compound as a free base. The free base was then dissolved in diethyl ether and slowly treated with HCl gas. The precipitate was collected by filtration to yield 15 g (72%) of the title compound as a white powder; $^1$H NMR (300 MHz, DMSO-d6) δ 2.83 (dd, J=12.8, 9.5 Hz, 1H), 3.06 (dd, J=12.8, 3.2 Hz, 1H), 4.80 –4.90 (m, 1H), 6.22 (d, J=4.0 Hz, 1H), 7.10–7.75 (m, 4H), 8.08 (brs, 2); MS (ES) m/z: 171.7, 173.7 (M$^+$+H); HRMS Calcd. for $C_8H_{10}ClNO$(M$^+$): 172.0529. Found: 172.0531.

(2S)-1-Amino-3-(4-benzyloxy-phenoxy)-propan-2-ol:

The title compound was prepared from (2S)-2-(4-benzyloxy-phenoxymethyl-oxirane (EP 0 714 883) according to the procedure described above as a white solid; $^1$H NMR (300 MHz, CDCl$_3$) δ 2.50–2.70 (m, 2H), 3.33 (brs, 2H), 3.60–3.90 (m, 3H), 5.02 (s, 2), 6.90 (d, J=6.7 Hz, 2H), 6.93 (d, J=6.7 Hz, 2H), 7.25–7.50 (m, 5H); MS (ES) m/z: 274.1 (M$^+$+H); HRMS Calcd. for $C_{16}H_{19}NO_3$(M$^+$): 273.1365. Found: 273.1347. Anal. Calcd. for $C_{16}H_{19}NO_3$: C, 70.31; H, 7.01; N, 5.12. Found: C, 70.39; H, 6.80; N, 5.23.

(2S)-1-Amino-3-(4-hydroxy-phenoxy)-propan-2-ol:

A mixture of (2S)-1-amino-3-(4-benzyloxy-phenoxy)-propan-2-ol ( ) (0.9 g, 3.3 mmol) 0.2 mL of acetic acid and 10% Pd/C (0.3 g) in 70 mL of ethanol was pressurized with 20 psi hydrogen and shaken over 2 hours. The catalyst was then removed by filtering through a short pad of silica gel and the solvent was removed to give the title compound as an off-white solid; $^1$H NMR (300 MHz, DMSO-d$_6$) δ 1.86 (s, 1H), 2.66 (dd, J=12.8, 5.3 Hz, 1H), 2.85 (dd, J=12.8, 3.5 Hz, 1H), 3.79–3.95 (m, 3H), 6.67 (d, J=6.6 Hz, 2H), 6.75 (d, J=6.6 Hz, 2H); MS (ES) m/z: 183.1 (M$^+$+H); HRMS Calcd. for $C_9H_{13}NO_3$(M$^+$+H): 183.0895. Found: 183.0892.

N-[2-Benzyloxy-5-(2-dibenzylamino-1-oxo-ethyl)-phenyl]-methanesulfonamide:

N-[2-Benzyloxy-5-(2-chloro-1-oxo-ethyl)-phenyl]-methanesulfonamide (EP 0 659 737) (17.0 g, 42.8 mmol) was dissolved in 200 mL of dimethylformamide and treated with dibenzylamine (22.0 g, 110 mmol). The mixture was stirred at room temperature overnight and then the solvent was removed. The residue was purified by silica gel chromatography using 20–50% ethyl acetate/hexanes as elute to give the title compound as a white solid; $^1$H NMR (300 MHz, CDCl$_3$) δ 2.94 (s, 3H), 3.77 (s, 2H), 3.82 (s, 2H), 5.16 (s, 2H), 6.75 (brs, 1H), 6.96 (d, J=8.7 Hz, 1H), 7.20–7.50 (m, 15 H), 7.67 (dd, J=8.7, 2.1 Hz, 1H), 8.10 (d, J=2.1 Hz, 1H); MS (ES) m/z: 515.2 (M$^+$+H); HRMS Calcd. for $C_{30}H_{30}N_2O_4S$(M$^+$): 514.1926. Found: 514.1927.

N-[2-Benzyloxy-5-(2-dibenzylamino-1-hydroxy-ethyl)-phenyl]-methanesulfonamide:

Sodium borohydride (0.37 g, 9.7 mmol) was added in portions to a stirred solution of N-[2-benzyloxy-5-(2-dibenzylamino-1-oxo-ethyl)-phenyl]-methanesulfonamide (1.0 g, 1.9 mmol) in 20 mL of methanol/tetrahydrofuran (5:2) at room temperature and the resulting solution was stirred for 2 hours. Methylene chloride was added and the resulting solution was washed with aqueous sodium bicarbonate, dried over MgSO$_4$. and the solvent was removed. Recrystallization from methylene chloride/hexanes gave the title compound as a crystalline solid; $^1$H NMR (300 MHz, CDCl$_3$) δ 2.58 (d, J=6.7 Hz, 2H), 2.86 (s, 2H), 2.92 (s, 2H), 3.55 (d, J=13.5 Hz, 2H), 3.70 (d, J=13.5 Hz, 2H), 4.11 (s, 1H), 4.64 (t, J=6.7 Hz, 1H), 5.10 (s, 2H), 6.92 (d, J=8.5 Hz, 1H), 7.00 (dd, J=8.5, 2.0 Hz, 1H), 7.20–7.50 (m, 16H), 7.89 (brs, 1H); MS (ES) m/z: 517.1 (M$^+$+H); HRMS Calcd. for $C_{30}H_{32}N_2O_4S$(M$^+$): 516.2083. Found: 516.2074.

N-[2-Benzyloxy-5-(2-amino-(1R)-1-hydroxy-ethyl)-phenyl]-methanesulfonamide:

A mixture of N-{2-benzyloxy-5-(2-iodo-(1R)-1-[(triethylsilyl)oxy-]-ethyl)-phenyl}-methanesulfonamide (EP 0 659 737) (4.48 g, 8 mmol) and sodium azide (0.65 g, 1 mmol) in 100 mL of hexamethylphosphoramide was stirred at 60° C. overnight. After cooling to room temperature the mixture was diluted with diethyl ether, washed with water, dried over Na$_2$SO$_4$ and concentrated under reduced pressure. The residue was dissolved in 200 mL of THF/H$_2$O (10:1) and triphenylphosphine (2.62 g, 10 mmol) was added. After overnight stirring at room temperature, the solvents were removed and the residue was partitioned between ethyl acetate and water. The organic layers were combined and dried over MgSO$_4$ and concentrated. The residue was redissolved in 100 mL of THF and tetrabutylammonium fluoride (10 mL, 1 M solution in THF) was added. The reaction was stirred for 2 hours then the solvent was removed in vacuo. The residue was purified by column chromatography on silica gel using triethylamine-methanol-methylene chloride (1:1:3) to give the title compound as a white solid; MS (ES) m/z:337.4 (M$^+$+H).

N-[5-(2-Amino-1-hydroxy-ethyl)-2-hydroxy-phenyl]-methanesulfonamide:

To a stirred suspension of N-[2-benzyloxy-5-(2-dibenzylamino-1-hydroxy-ethyl)-phenyl]-methanesulfonamide (1.03 g, 2 mmol) and 10% Pd/C (0.4 g) in methanol (100 mL) at room temperature is added anhydrous HCO$_2$NH$_4$ (1.26 g, 20 mmol) under a nitrogen atmosphere. The resulting mixture is refluxed for 2 hours. After cooling to room temperature the catalyst is removed by filtration through a celite pad and washed with methanol. The filtrate is evaporated under reduced pressure to give the titled compound as a pale yellowish solid; $^1$H NMR (300 MHz, DMSO-d$_6$) δ 2.62 (dd, J=12.6, 8.7 Hz, 1H), 2.75 (dd, J=12.6, 3.7 Hz, 1H), 2.90 (s, 3H), 4.47 (dd, J=8.7, 3.7 Hz, 1H), 6.84 (d, J=9.1 Hz, 1H), 6.96 (dd, J=9.1, 2.0 Hz, 1H), 7.16 (d, J=2.1 Hz, 1H), 8.44 (s, 1H); MS (ES) m/z: 246.7 (M$^+$+H); HRMS Calcd. for $C_9H_{14}N_2O_4S$(M$^+$): 246.0674. Found: 246.0672.

N-[5-(2-Amino-(1R)-1-hydroxy-ethyl)-2-hydroxy-phenyl]-methanesulfonamide:

Method A: A mixture of N-{2-benzyloxy-5-(2-iodo-(1R)-1-[(triethylsilyl)oxy-]-ethyl)-phenyl}-methanesulfonamide (EP 0 659 737) (8.60 g, 15.3 mmol) and benzylamine (21.4 g, 200 mmol) was heated at 60° C. for 24 hours. The reaction mixture was cooled, diluted with hexanes (500 mL), and the residue was washed with diethyl ether. The combined solvents were removed and the residue was purified by silica gel column eluting with 30 to 100% Et$_2$O/hexanes. The fractions with molecular weight of 540 were concentrated and re-dissolved in 200 mL of THF and TBAF (20 mL, 1.0 M solution in THF) was added. After stirring at room temperature for 4 hours the reaction mixture was then poured into water and extracted with CH$_2$Cl$_2$. The organic layers were passed through a short pad of silica gel eluting with 10% methanol/CH$_2$Cl$_2$. The solvents were removed and the residue were dissolved in methanol (200 mL). 10% Pd/C (0.6 g) and anhydrous HCO$_2$NH$_4$ (6.3 g, 100 mmol) were added. The resulting mixture was refluxed under a nitrogen atmosphere for 2 hours. After cooling to room temperature the catalyst was removed by filtration through a celite pad and washed with methanol. The filtrate is evaporated under reduced pressure to give the title compound as an off-white solid; $^1$H NMR (300 MHz, MeOH-d$_4$) δ 2.95 (s, 3H), 2.99 (dd, J=9.7, 9.2 Hz, 1H), 3.07 (dd, J=9.7, 3.6 Hz, 1H), 4.75 (dd, J=9.2, 3.6 Hz, 1H), 6.90 (d, J=8.3 Hz, 1H), 7.12 (dd, J=8.3, 2.1 Hz, 1H), 7.38 (d, J=2.1 Hz, 1H), 8.44 (s, 1H); MS (ES) m/z: 246.7 (M$^+$+H)); HRMS Calcd. for $C_9H_{14}N_2O_4S$: 246.0674. Found: 246.0672.

Method B: To a stirred solution of N-[2-benzyloxy-5-(2-Bromo-1-hydroxy-ethyl)-phenyl]-methanesulfonamide (EP 0 659 737) (15.05 g, 0.376 mol) in DMSO (150 ml) was added sodium iodide (3.76 g, 0.376 mol) and sodium azide (9.48 g, 0.150 mol). The mixture was stirred for 5 days under Nitrogen atmosphere. The reaction mixture was poured onto water and extracted three times with ethyl acetate. The combined organic layers were dried over sodium sulfate and concentrated. The residue was triturated with water and hexanes. Recovered yellow solid as of N-[5-((1R)-2-azido-1-hydroxy-ethyl)-2-benzyloxy-phenyl]-methanesulfonamide (12.85 g, 94%): $^1$H NMR (300 MHz, CDCl$_3$): δ 2.93(s, 3H), 3.45(d, J=9.0 Hz, 2H), 3.46(m, 1H), 5.11(s, 2H), 6.80(s, 1H), 6.99(d, J=8.4 Hz, 1H), 7.15(dd, J=6 Hz, 2.1 Hz, 1H), 7.26(s, 1H), 7.39(s, 5H), 7.53(d, J=2.1 Hz, 1H); MS (ES) m/z 361.4 (M$^+$–H, 70%). A mixture of N-[5-((1R)-2-Azido-1-hydroxy-ethyl)-2-benzyloxy-phenyl]-methanesulfonamide ( ) (12.85 g, 0.037 mol) and 10% Palladium on carbon (2.75 g) in ethanol (100 ml) was hydrogenated under 45 PSI for two days. The reaction mixture was filtered through celite and concentrated. The title compound was recovered as a tan solid (6.08 g, 66%): $^1$H NMR (300 MHz, DMSO-d$_6$): δ 2.60(m, 2H), 2.87(s, 3H), 4.34(m, 1H), 6.79(d, J=9.0 Hz, 1H), 6.89(d, J=9.0 Hz, 2H).

The following procedures describe the preparation of intermediates useful in the preparation of compounds of this invention.

INTERMEDIATE 1

N-(3,4-Dimethoxy-phenyl)-4-fluoro-benzenesulfonamide 3,4-Dimethoxyaniline(1.01 g, 6.99 mM) was added to a solution of 4-Fluorobenzenesulfonyl chloride (1.50 g, 7.69 mM) in anhydrous pyridine(10 ml). The reaction was stirred overnight. The reaction was quenched with 1N HCl$_{aq}$. (20 ml) and washed with ethyl acetate(3×20 ml). The organic extracts were combined, dried(sodium sulfate), solids filtered off and concentrated. The desired product was isolated using silica gel flash chromatography of 1.30 g as a yellow solid. H$^1$ NMR(CDCl$_3$) δ 3.79(s, 3H), 3.86(s, 3H), 6.50(d, 1H), J=4.71 Hz), 6.68(d, 1H, J=2.64 Hz), 6.71 (d, 1H, J=2.76 Hz), 7.11 (d, 2H, J=8.67 Hz), 7.75(m, 2H). MS(ES) m/z 328.9; (M+NH$_4$$^+$); HRMS for (MH$^+$) $C_{14}H_{14}SFNO_4$: 260.1511.

INTERMEDIATE 2

N-Benzyl-N-(3,4-dimethoxy-phenyl)-4-fluoro-benzenesulfonamide

N-(3,4-Dimethoxy-phenyl)-4-fluoro-benzenesulfonamide (0.51 g, 1.61 mM) was added to a solution of benzyl bromide (0.57 g, 4.82 mM) and potassium carbonate (0.66 g, 4.82 mM)in anhyrous acetone(10 ml). The reaction was stirred overnight. The undissolved solids were removed by filtration and the mother liquor was concentrated. This gum was triturated with hexanes to afford 0.52 g of the desired product as an off-white solid. H$^1$ NMR(CDCl$_3$) δ 3.66(s, 3H), 3.81(s, 3H), 6.42(m, 2H), 6.66(d, 1H, J=8.70 Hz), 7.23(m, 7H), 7.71(m, 2H). MS(ES) m/z 401.9; (MH$^+$); HRMS for $C_{21}H_{20}SFNO_4$: 401.1094.

INTERMEDIATE 3

N-Benzyl-N-(3,4-dimethoxy-phenyl)-4-(1,4-dioxa-8-aza-spiro[4.5]dec-8-yl)-benzenesulfonamide 1,4-Dioxa-8-azaspiro[4.5]decane (0.14 ml, 0.95 mM) was added to a solution of N-Benzyl-N-(3,4-dimethoxy-phenyl)-4-fluoro-benzenesulfonamide(0.19 g, 0.47 mM) and potassium carbonate (0.66 g, 4.82 mM)in anhyrous 1,3-dimethyl-3,4,5,6-tetrahydro-2(1H)-pyrimidinone(5 ml). The reaction was stirred at 70° C. for two days. The reaction was quenched with water(50 ml). The precipitate was washed with water and dried under reduced pressure to afford 0.15 g of the desired product as a tan solid. H$^1$ NMR(CDCl$_3$) δ 1.81(t, 4H, J=5.67 Hz), 3.50(t, 4H, J=5.97 Hz), 3.65(s, 3H), 3.81 (s, 3H), 4.01 (s, 4H), 4.66(s, 2H), 6.43(d, 1H, J=2.34 Hz), 6.53(m, 1H), 6.66(d, 1H, J=8.58 Hz), 6.90(d, 1H, J=9.03 Hz), 7.19(m, 6H), 7.53(d, 2H, J=9.00 Hz). MS(ES) m/z 525.0; (MH$^+$); HRMS for $C_{28}H_{32}SN_2O_6$: 525.2049.

INTERMEDIATE 4

N-Benzyl-4-fluoro-benzenesulfonamide

The title compound was prepared according to the procedure of Intermediate 1 as a yellow solid. H$^1$ NMR(CDCl$_3$) δ 4.17(d, 2H, J=6.06 Hz), 4.81(t, 1H, J=5.82 Hz), 7.19(m, 4H), 7.27(m, 3H), 7.88(m, 2H). MS(ES) m/z 265.9; (MH$^+$); HRMS for $C_{13}H_{12}S$ F NO$_2$: 266.0625.

INTERMEDIATE 5

N-Benzyl-N-(3,4-dimethoxy-phenyl)-4-(4-oxo-piperidin-1-yl)-benzenesulfonamide

N-Benzyl-N-(3,4-dimethoxy-phenyl)-4-(1,4-dioxa-8-aza-spiro[4.5]dec-8-yl)-benzenesulfonamide(0.10 g, 0.19 mM) was stirred in 6M HCl (2 ml) and acetone(5 ml) at 60° C. overnight. The reaction mixture was basified with 5N NaOH$_{aq}$. (until pH>7) and washed with ethyl acetate (3×10 ml). The organic extracts were dried with sodium sulfate, passed through a plug of magnesol, concentrated and triturated with hexanes to afford 0.65 g of the desired product as a white solid. H$^1$ NMR(CDCl$_3$) δ 2.58(t, 4H, J=6.06 Hz), 3.67(s, 3H), 3.74(t, 4H, J=6.12 Hz), 3.81(s, 3H), 4.71(s, 2H), 6.48(m, 3H), 6.67(d, 1H, J=8.46 Hz), 6.93(d, 2H), J=9.9 Hz), 7.20(m, 4H), 7.59(d, 2H, J=4.71 Hz). MS(ES) m/z 481.0; (MH$^+$); HRMS for $C_{26}H_{28}SN_2O_5$: 481.1778.

INTERMEDIATE 6

N-Benzyl-N-(tert-butylcarbonyl)-4-fluoro-benzenesulfonamide t-Boc-Anhydride(0.18 g, 0.83 mM) was added to N-Benzyl-4-fluoro-benzenesulfonamide(0.2 g, 0.75 mM) and 4-dimethylaminopyridine(scoopful) in anhydrous methylene chloride (5 ml). The reaction was stirred for two hours at room temperature. The reaction was quenched with 1N HCl(20 ml) and washed with methylene chloride(3×10 ml). The organic extracts were combined, dried with sodium sulfate and passed through a plug of magnesol and concentrated to afford an oil. The oil was triturated with hexanes to afford 0.22 g of the desired product as a white solid. H$^1$ NMR(CDCl$_3$) δ 1.34(s, 9 H), 5.11(s, 2H), 7.08(t, 2H, J=3.42 Hz), 7.34(m, 5H), 7.66(m, 2H). MS(ES) m/z 383.1; (M+NH$_4$$^+$); HRMS for $C_{26}H_{28}SN_2O_5$: 366.1179.

INTERMEDIATE 7

N-Benzyl-N-butyl-4-(1,4-dioxa-8-aza-spiro[4.5]dec-8-yl)benzenesulfonamide

The title compound was prepared according to the procedure of Intermediate 3 as a yellow solid. H$^1$ NMR(CDCl$_3$) δ 0.74(t, 3 H, J=7.26 Hz), 1.08(m, 2H), 1.29(m, 2H), 1.79(t, 4H, J=5.70 Hz), 3.05(t, 2H, J=7.74 Hz), 3.50(t, 4H, J=5.76

Hz), 4.01(s, 4H), 4.27(s, 6.93(d, 2H, J=5.31 Hz), 7.28(m, 5H), 7.66(d, 2H, J=5.41 Hz). MS(ES) m/z 445.3; (MH$^+$); HRMS for $C_{24}H_{32}SN_2O_4$: 444.2082.

INTERMEDIATE 8

N-Benzyl-N-(tert-butylcarbonyl)-4-(1,4-dioxa-8-aza-spiro[4.5]dec-8-yl)benzenesulfonamide The title compound was prepared according to the procedure of Intermediate 3 as a yellow solid. H$^1$ NMR(CDCl$_3$) δ 1.34(s, 9 H), 1.78(t, 4H, J=5.82 Hz), 3.48(t, 4H, J=5.82 Hz), 3.99(s, 4H), 5.09(s, 2H), 6.81(t, 2H, J=4.83 Hz), 7.35(m, 5H), 7.50d, 2H, =4.97 Hz). MS(ES) m/z 489.0; (MH$^+$); HRMS for $C_{25}H_{32}SN_2O_6$: 488.1977.

INTERMEDIATE 9

N-Benzyl-N-butyl-4-(4-oxo-piperidin-1-yl)-benzenesulfonamide

The title compound was prepared from Intermediate 7 according to the procedure of Intermediate 5 as a yellow solid. H$^1$ NMR(CDCl$_3$) δ 0.75(t, 3H, J=7.26 Hz), 1.12(m, 2H), 1.32(m, 2H), 2.59(t, 4H, J=6.09 Hz), 3.08(t, 2H, J=7.77 Hz), 3.76(t, 4H, J=6.18 Hz), 4.32 (s, 2H), 6.94(d, 2H, J=5.31 Hz), 7.31(m, 5H), 7.72(d, 2H, J=5.41 Hz). MS(ES) m/z 401.5; (MH$^+$); HRMS for $C_{22}H_{28}SN_2O_3$.

INTERMEDIATE 10

N-Butyl-4-(1,4-dioxa-8-aza-spiro[4.5]dec-8-yl)-benzenesulfonamide

The title compound was prepared from N-butyl-4-fluoro-benzenesulfonamide) according to the procedure of Intermediate 3 as a white solid; mp 122–124° C.; $^1$H NMR (CDCl$_3$) δ 0.85 (t, J=7.23 Hz, 3H), 1.21–1.30 (m, 2H), 1.32–1.49 (m, 2H), 1.65 (s, 1H), 1.80 (t, J=5.79 Hz, 4H), 2.90 (q, J=6.75 Hz, 2H), 3.48 (t, J=5.7 Hz, 4H), 4.00 (s, 4H), 6.88–6.93 (m, 2H), 7.67–7.77 (m, 2H); MS (ES) m/z 355.0 (MH$^+$); $C_{17}H_{26}N_2O_4S$.

INTERMEDIATE 11

N-Butyl-4-(4-oxo-piperidin-1-yl)-benzenesulfonamide

The title compound was prepared from N-butyl-4-(1,4-dioxa-8-aza-spiro[4.5]dec-8-yl)-benzenesulfonamide according to the procedure of Intermediate 5 as an off-white solid; mp 79–82° C.; $^1$H NMR (CDCl$_3$) δ 0.85 (t, J=7.26 Hz, 3H), 1.23–1.37 (m, 2H), 1.40–1.50 (m, 2H), 1.65 (s, 1H), 2.59 (t, J=6.12 Hz, 4H), 2.92 (q, J=6.69 Hz, 2H), 3.75 (t, J=6.09 Hz, 4h), 6.92–6.97 (m, 2H), 7.70–7.80 (m, 2H); MS (ES) m/z 311.0 (MH$^+$); HRMS for $C_{15}H_{22}N_2O_{3S}$: 310.1349.

INTERMEDIATE 12

1-(4-Fluoro-benzenesulfonyl)-pyrrolidine-2-carboxylic Acid Isopropyl Ester

The title compound was prepared from DL-proline, isopropanol, and 4-fluorobezenesulfonyl chloride according to the procedure of Intermediate 48 as a clear oil; $^1$H NMR (CDCl$_3$) δ 1.21–1.28 (m, 6H), 1.80–1.85 (m, 1H), 1.95–2.10 (m, 3H), 3.31–3.49 (m, 2H), 4.26–4.36 (m, 1H), 4.95–5.08 (m, 1H), 7.15–7.23 (m, 2H), 7.89–8.08 (m, 2H); MS (ES) m/z 315.8 (MH$^+$); HRMS for $C_{14}H_{18}FNO_4S$: 338.0830 (M+Na).

INTERMEDIATE 13

1-[4-(1,4-Dioxa-8-aza-spiro[4.5]dec-8-yl)-benzenesulfonyl]-pyrrolidine-2-carboxylic Acid Isopropyl Ester The title compound was prepared with 1-(4-fluoro-benzenesulfonyl)-pyrrolidine-2-carboxylic acid isopropyl ester ( ) according to the procedure of Intermediate 3 as a clear oil; $^1$H NMR (CDCl$_3$) δ 1.23–1.28 (m, 6H), 1.80–1.85 (t, J=5.82 Hz, 4H), 1.91–2.05 (m, 3H), 3.24–3.29 (m, 2H), 3.42–3.51 (m, 4H), 4.00 (s, 4H), 4.19–4.25 (m, 1H), 4.96–5.09 (m, 2H), 6.88–6.93 (m, 2H), 7.66–7.74 (m, 2H); MS (ES) m/z 438.9 (MH$^+$); HRMS for $C_{21}H_{30}N_2O_6S$: 439.1896 (MH$^+$).

INTERMEDIATE 14

1-[4-(4-Oxo-piperidin-1-yl)-benzenesulfonyl]-pyrrolidine-2-carboxylic Acid Isopropyl Ester The title compound was prepared with 1-[4-(1,4-dioxa-8-aza-spiro[4.5]dec-8-yl)-benzenesulfonyl]-pyrrolidine-2-carboxylic acid isopropyl ester ( ) according to the procedure of Intermediate 5 as a white solid; mp 97–101° C.; $^1$H NMR (CDCl$_3$) δ 1.23–1.28 (m, 6H), 1.75–1.80 (m, 1H), 1.94–2.07 (m, 3H), 2.58 (t, J=6.3 Hz, 4H), 3.27–3.36 (m, 1H), 3.42–3.51 (m, 1H), 3.75 (t, 6.09 Hz, 4H), 4.23–4.28 (m, 1H), 4.97–5.10 (m, 1H), 6.91–6.96 (m, 2H) 7.70–7.84 (m, 2H); MS (ES) m/z 394.9 (MH$^+$); HRMS for $C_{19}H_{26}N_2O_5S$: 395.1631 (MH$^+$).

INTERMEDIATE 15

1-(4-Fluoro-benzenesulfonyl)-pyrrolidine-2-carboxylic Acid

To a stirred solution of 2.06 g (6.5 mmol) of 1-(4-fluoro-benzenesulfonyl)-pyrrolidine-2-carboxylic acid isopropyl ester ( ) in 10 mL of methanol was added 2.3 mL (13 mmol) of 5N NaOH. After 2 hours, the solvent was removed in vacuo and the aqueous residue was acidified with 1N HCl and then extracted twice with ethyl acetate. The organic layer was dried over magnesium sulfate and concentrated in vacuo to afford 1.69 g of the title compound as a white solid; ; mp 145–148° C.; $^1$H NMR (DMSO) δ 1.56–1.63 (m, 1H), 1.78–2.05 (m, 4H), 3.13–3.21 (m, 1H), 4.10–4.15 (m, 1H), 7.42–7.50 (m, 2H), 7.88–7.95 (m, 2H), 12.75 (bs, 1H); MS (ES) m/z 271.9 (MH$^-$); HRMS for $C_{11}H_{12}N_2FO_4S$: 274.0543 (MH$^+$).

INTERMEDIATE 16

1-(4-Fluoro-benzenesulfonyl)-pyrrolidine-2-carboxylic Acid Benzyl Ester

HCl gas was bubbled into a solution of 1.49 g of 1-(4-fluoro-benzenesulfonyl)-pyrrolidine-2-carboxylic acid ( ) and 6 mL of benzyl alcohol for 15 minutes and the resulting mixture was allowed to stir overnight. 10 mL of 2,3-butanediol and a catalytic amount of DMAP was then added and stirred for 2 days. The solvent was removed in vacuo and the residue was purified by flash column chromatography (3:1 Hexanes:Ethyl Acetate) to give 1.01 g of the title compound as a clear gum; $^1$H NMR (CDCl$_3$) δ 1.74–1.85 (m, 1H), 1.95–2.18 (m, 3H), 3.32–3.58 (m, 2H), 4.40–4.44 (m, 1H), 5.15 (s, 2H), 7.11–7.17 (m, 2H), 7.33–7.41 (m, 5H), 7.84–7.90 (m, 2H); MS (ES) m/z 363.9 (MH$^+$); HRMS for $C_{18}H_{18}FNO_4S$: 364.1012 (MH$^+$).

INTERMEDIATE 17

1-[4-(1,4-Dioxa-8-aza-spiro[4.5]dec-8-yl)-benzenesulfonyl]-pyrrolidine-2-carboxylic Acid Benzyl Ester The title compound was prepared from 1-(4-fluoro-benzenesulfonyl)-pyrrolidine-2-carboxylic acid benzyl ester ( ) according to the procedure of Intermediate 3 as a gum; $^{1}$H NMR (CDCl$_3$) δ 1.54–1.62 (m, 1H), 1.67 (t, J=5.64 Hz, 4H), 1.69–1.90 (m, 4H), 3.07–3.15 (, 1H), 3.35–3.48 (m, 4H), 3.92 (s, 4H), 4.15–4.20 (m, 1H), 5.14 (s, 2H), 7.05 (d, J=9.09 Hz, 2H), 7.22–7.43 (m 5H), 7.58 (d, J=9.00 Hz, 2H); MS (ES) m/z 487.0 (MH$^+$); HRMS for C$_{25}$H$_{30}$N$_2$O$_6$S: 487.1890 (MH$^+$).

INTERMEDIATE 18

{Butyl-[4-(4-oxo-piperidin-1-yl)-benzenesulfonyl]-amino}-acetic Acid Benzyl Ester The title compound was prepared from N-butyl-4-(4-oxo-piperidin-1-yl)-benzenesulfonamide ( ) and benzyl bromoacetate according to the procedure of Intermediate 2 as a gum; $^{1}$H NMR (CDCl$_3$) δ 0.85 (t, J=7.23 Hz, 3H), 1.19–1.32 (m, 2H), 1.43–1.53 (m, 2H), 2.56 (t, J=6.12 Hz, 4H), 3.19 (t, J=7.47 Hz, 2H), 3.72 (t, J=6.06 Hz, 4H), 4.09 (s, 2H), 5.10 (s, 2H), 6.84–6.89 (m, 2H), 7.29–7.40 (m, 5H), 7.69–7.74 (m, 2H); MS (ES) m/z 45.94 (MH$^+$); HRMS for C$_{25}$H$_{30}$N$_2$O$_6$S: 459.1945 (MH$^+$).

INTERMEDIATE 19

(2S)-1-4-Fluoro-benzenesulfonyl)-pyrrolidine-2-carboxylic Acid Benzyl Ester

The title compound was prepared from L-proline, benzyl alcohol, and 4-fluorobezenesulfonyl chloride according to the procedure of Intermediate 48 as a gum; $^{1}$H NMR (CDCl$_3$) δ 1.80–1.85 (m, 1H), 1.94–2.30 (m, 3H), 3.31–3.51 (m, 2H), 4.42 (dd, J=3.57 Hz, 8.13 Hz, 1H), 5.14 (s, 2H), 6.91–7.17 (m, 2H), 7.32–7.40 (m, 5H), 7.84–7.90 (m, 2H); MS (ES) m/z 363.8 (MH$^+$); HRMS for C$_{18}$H$_{18}$FNO$_4$S: 364.1011.

INTERMEDIATE 20

1-[4-(1,4-Dioxa-8-aza-spiro[4.5]dec-8-yl)-benzenesulfonyl]-pyrrolidine-2-carboxylic Acid Methylamide 0.57 g of 1-[4-(1,4-dioxa-8-aza-spiro[4.5]dec-8-yl)-benzenesulfonyl]-pyrrolidine-2-carboxylic acid isopropyl ester ( ) was stirred in 20 mL methyl amine (40% wt in water) at 100° C. in a sealed tube for 5 days. The methyl amine was allowed to evaporate and the residual aqueous solution was left to stand overnight uncapped. The following morning, a white precipitate was present, which was collected by vacuum filtration. The precipitate was washed with water and hexanes. The original aqueous solution was then extracted twice with ethyl acetate. The organic layer was then dried over sodium sulfate and concentrated in vacuo to afford more product. 0.31 g of the title compound was collected as a white solid; mp 137–139° C.; $^{1}$H NMR (CDCl$_3$) δ 1.52–1.72 (m, 5H), 1.81 (t, J=5.82 Hz, 4H), 2.15–2.20 (m, 1H), 2.86 (d, J=4.95 Hz, 3H), 3.08–3.55 (m, 1H), 3.49–3.55 (m, 4H), 4.00 (s, 4H), 6.89–6.94 (M, 2H), 6.99–7.01 (m, 1H), 7.61–7.73 (m, 2H); MS (ES) m/z 410.0 (MH$^+$); HRMS for C$_{19}$H$_{27}$N$_3$O$_5$S: 410.1740.

INTERMEDIATE 21

(2S)-1-[4-(1,4-Dioxa-8-aza-spiro[4.5]dec-8-yl)-benzenesulfonyl]-pyrrolidine-2-carboxylic Acid Benzyl Ester The title compound was prepared with 1-(4-fluoro-benzenesulfonyl)-pyrrolidine-2-carboxylic acid benzyl ester ( ) according to the procedure of Intermediate 3 as a colorless gum; $^{1}$H NMR (CDCl$_3$) δ 1.67–1.82 (m, 4H), 1.92–2.03 (m, 3H), 3.17–3.36 (m, 3H), 3.42–3.64 (m, 4H), 4.00 (s, 4H), 4.24–4.47 (m, 1H), 5.16 (s, 2H), 6.62–6.91 (m, 2H), 7.29–7.42 (m, 5H), 7.66–7.72 (m, 2H); MS (ES) m/z 487.0 (MH$^+$); HRMS for C$_{25}$H$_{30}$N$_2$O$_6$S: 487.1893.

INTERMEDIATE 22

(2S)-1-[4-(4-Oxo-piperidin-1-yl)-benzenesulfonyl]-pyrrolidine-2-carboxylic Acid Benzyl Ester The title compound was prepared with (2S)-1-[4-(1,4-dioxa-8-aza-spiro[4.5]dec-8-yl)-benzenesulfonyl]-pyrrolidine-2-carboxylic acid benzyl ester ( ) according to the procedure of Intermediate 5 as a gum; $^{1}$H NMR (CDCl$_3$) δ 1.65–1.82 (m, 1H), 1.90–2.17 (m, 3H), 2.57 (t, J=6.09 Hz, 4H), 3.28–3.34 (m, 1H), 3.42–3.49 (m, 1H), 3.73 (t, J=6.09 Hz, 4H), 4.35–4.39 (M, 1H), 5.16 (s, 2H), 6.87–6.92 (m, 2H), 7.29–7.40 (m, 5H), 7.73–7.79 (m, 2H); MS (ES) m/z 442.9 (MH$^+$); HRMS for C$_{23}$H$_{26}$N$_2$O$_5$S: 443.1631 (MH$^+$).

INTERMEDIATE 23

(2R)-1-[4-(4-Oxo-piperidin-1-yl)-benzenesulfonyl]-pyrrolidine-2-carboxylic Acid Benzyl Ester The title compound was prepared with (2R)-1-[4-(1,4-dioxa-8-aza-spiro[4.5]dec-8-yl)-benzenesulfonyl]-pyrrolidine-2-carboxylic acid benzyl ester according to the procedure of Intermediate 5 as a gum; $^{1}$H NMR (CDCl$_3$) δ 1.61–1.82 (m, 1H), 1.92–2.06 (m, 3H), 2.58 (t, J=6.18 Hz, 4H), 3.27–3.35 (m, 1H), 3.42–3.52 (m, 1H), 3.73 (t, J=6.06 Hz, 4H), 4.35–4.39 (dd, J=3.87 Hz, 7.98 Hz, 1H), 5.17 (s, 2H), 6.85–6.92 (m, 2H), 7.29–7.41 (m, 5H), 7.73–7.88 (m, 2H); MS (ES) m/z 442.9 (MH$^+$); HRMS for C$_{23}$H$_{26}$N$_2$O$_5$S: 443.1632 (MH$^+$).

INTERMEDIATE 24

8-[4-(Toluene-4-sulfonyl)-phenyl]-1,4-dioxa-8-aza-spiro[4.5]decane

To a solution of 4-fluorophenyl-4-tolylsulfone (1.25 g, 5 mmol) in N,N'-dimethylpropyleneurea (5 ml) was added 1,4-dioxa-8-aza-spiro[4.5]decane (0.88 g, 6 mmol), and potassium carbonate (0.83 g, 6 mmol). The mixture was stirred at room temperature for 4 h and then heated at 70° C. for 18 h. An additional 0.22 g of 1,4-dioxa-8-aza-spiro[4.5]decane was added, and the reaction was continued for 1 day. The mixture was cooled to room temperature, and treated with water. The resulting suspension was filtered, and the precipitate washed with water and methanol, and dried in vacuo to give 1.80 g of a white solid; m.p. 164–165° C.; MS (ES) m/z 373.9 (MH$^+$); HRMS (EI) Calcd. for C$_{20}$H$_{23}$NO$_4$S (M$^+$): 373.1348, Found: 373.1342.

INTERMEDIATE 25

1-[4-(Toluene-4-sulfonyl)-phenyl]-piperidin-4-one

The title compound was prepared according to the procedure of Intermediate 40 from 2.0 g (4.7 mmol) of 8-[4-(toluene-4-sulfonyl)-phenyl-1,4-dioxa-8-aza-spiro[4.5] decane, yielding 1.42 g of a white solid; m.p. 159–160° C.; MS (ES) m/z 329.9 (MH$^+$); HRMS (EI) Calcd. for C$_{18}$H$_{19}$NO$_3$S (M$^+$): 329.1086, Found: 329.1073.

INTERMEDIATE 26

2-But-2-ynyl-2-[4-(1,4-dioxa-8-aza-spiro[4.5]dec-8-yl)-benzenesulfonyl]-hex-4-ynoic Acid tert-Butyl Ester The title compound was prepared according to the procedure of Intermediate 24 from 0.53 g (3.6 mmol) of 1,4-dioxa-8-aza-spiro[4.5]decane and 1.13 g (3.0 mmol) of 2-but-2-[4-fluorobenzenesulfonyl]-hex-4-ynoic acid tert-butyl ester, yielding 1.52 g of a colorless foam; MS (ES) m/z 502.3 (MH$^+$); HRMS (EI) Calcd. for $C_{27}H_{35}NO_6S$ (M$^+$): 501.2185, Found: 501.2177.

INTERMEDIATE 27

2-But-2-ynyl-2-[4-(4-oxo-piperidin-1-yl)-benzenesulfonyl]-hex-4-ynoic Acid tert-Butyl Ester The title compound was prepared according to the procedure of Intermediate 40 from 1.40 g (2.8 mmol) of 2-but-2-ynyl-2-[4-(1,4-dioxa-8-aza-spiro[4.5]dec-8-yl)-benzenesulfonyl]-hex-4-ynoic acid tert-butyl ester, yielding 1.19 g of a white solid; m.p. 128–130° C.; MS (ES) m/z 458.2 (MH$^+$); HRMS (EI) Calcd. for $C_{25}H_{31}NO_5S$ (M$^+$): 457.1923, Found: 457.1919.

INTERMEDIATE 28

4-Fluoro-N-(2-hydroxyethyl)-benzenesulfonamide

The title compound was prepared according to the procedure of Intermediate 33 from 3.97 g (20 mmol) of 4-fluorobenzenesulfonyl chloride and 3.11 g (50 mmol) of ethanolamine, yielding 3.0 g of a white solid; m.p. 77–78° C.; MS (ES) m/z 219.8 (MH$^+$); HRMS (EI) Calcd. for $C_8H_{10}FNO_3S$ (M$^+$): 219.0366, Found: 219.0369.

INTERMEDIATE 29

4-(1,4-Dioxa-8-aza-spiro[4.5]dec-8-yl)-N-(2-hydroxyethyl)-benzenesulfonamide

The title compound was prepared according to the procedure of Intermediate 24 from 2.28 g (15.6 mmol) of 1,4-dioxa-8-aza-spiro[4.5]decane and 2.85 g (13.0 mmol) of 4-fluoro-N-(2-hydroxyethyl)-benzenesulfonamide, yielding 3.0 g of a colorless gum; MS (ES) m/z 343.2 (MH$^+$); HRMS (EI) Calcd. for $C_{15}H_{22}N_2O_5S$ (M$^+$): 342.1249, Found: 342.1235.

INTERMEDIATE 30

N-(2-Hydroxyethyl)-4-(4-oxo-piperidin-1-yl)-benzenesulfonamide

The title compound was prepared according to the procedure of Intermediate 40 from 2.23 g (6.5 mmol) of 4-(1,4-dioxa-8-aza-spiro[4.5]dec-8-yl)-N-(2-hydroxyethyl)-benzenesulfonamide, yielding 1.88 g of a colorless gum; MS (ES) m/z 299.1 (MH$^+$); HRMS (EI) Calcd. for $C_{13}H_{18}N_2O_4S$ (M$^+$): 298.0988, Found: 298.0974.

INTERMEDIATE 31

8-[4-(Piperidine-1-sulfonyl)-phenyl]-1,4-dioxa-8-aza-spiro[4.5]decane

The title compound was prepared with N-piperidine-4-fluoro-benzenesulfonamide according to the procedure of Intermediate 37 as a white solid; $^1$H NMR (CDCl$_3$) δ 1.36–1.44 (m, 2H), 1.59–1.67 (m, 4H), 1.81 (t, J=5.79 Hz, 4H), 2.95 (t, J=5.37 Hz, 4H), 3.49 (t, J=5.7 Hz, 4H), 4.00 (s, 4H), 6.89–6.93 (m, 2H), 7.56–7.61 (m, 2H); MS (ES) m/z 367.32 (MH$^+$); HRMS for $C_{18}H_{26}N_2O_4S$: 367.1683.

INTERMEDIATE 32

8-[4-(Pyrrolidine-1-sulfonyl)-phenyl]-1,4-dioxa-8-aza-spiro[4.5]decane

The title compound was prepared with N-pyrrolidine-4-fluoro-benzenesulfonamide according to the procedure of Intermediate 37 as a white needles; $^1$H NMR (CDCl$_3$) δ 1.72–1.77 (m, 4H), 1.79–1.83 (m, 4H), 3.14–3.23 (m, 4H), 3.47–3.51 (m, 4H), 4.00 (s, 4H), 6.89–6.95 (m, 2H), 7.61–7.72 (m, 2H); MS (ES) m/z 353.29 (MH$^+$); HRMS for $C_{17}H_{24}N_2O_4S$: 353.1.

INTERMEDIATE 33

N-Cyclopropylmethyl-4-fluoro-benzenesulfonamide

To a stirred solution of 2 mL (23 mmol) of aminomethyl cyclopropane in 25 mL methylene chloride was added 4.8 mL (28 mmol) of diisopropylethyl amine. After 10 minutes of stirring, 4.49 g (23 mmol) of 4-fluorobenzene sulfonyl chloride was added and the mixture was allowed to stir for 4 hours. The reaction mixture was quenched with water and the organic layer was washed twice with 1N HCl, twice with water, dried over magnesium sulfate and then concentrated in vacuo. Then the solid was dried under vacuum to give 4.65 g of the title compounds as an off white solid; $^1$H NMR (CDCl$_3$) δ 0.08–0.13 (m, 2H), 0.45–0.51 (m, 2H), 0.83–0.94 (m, 1H), 2.86 (t, J=6.9 Hz, 2H), 4.66–4.71 (m, 1H), 7.12–7.23 (m, 2H); MS (ES) m/z 218.23 (MH$^+$); HRMS for $C_{10}H_{12}FNO_2S$: 218.0637.

INTERMEDIATE 34

1-[4-(Pyrrolidine-1-sulfonyl)-phenyl]-piperidin-4-one

The title compound was prepared with 8-[4-(pyrrolidine-1-sulfonyl)-phenyl]-1,4-dioxa-8-aza-spiro(4.5]decane according to the procedure of Intermediate 40 as a fluffy beige solid; $^1$H NMR (CDCl$_3$) δ 1.70–1.79 (m, 4H), 2.59 (t, J=6.18 Hz, 4H), 3.20–3.29 (m, 4H), 3.75 (t, J=6.09 Hz, 4H), 6.86–6.97 (m, 2H), 7.70–7.76 (m, 2H); MS (ES) m/z 230.2 (MH$^+$); HRMS for $C_{15}H_{20}N_2O_3S$: 230.0645.

INTERMEDIATE 35

1-[4-(Piperidine-1-sulfonyl)-phenyl]-piperidin-4-one

The title compound was prepared with 8-[4-(piperidine-1-sulfonyl)-phenyl]-1,4-dioxa-8-aza-spiro[4.5]decane according to the procedure of Intermediate 40 as an off white solid; $^1$H NMR (CDCl$_3$) δ 1.37–1.45 (m, 2H), 1.60–1.68 (m, 4H), 2.59 (t, J=6.18 Hz, 4H), 2.67 (t, J=5.4 Hz, 4H), 3.75 (t, J=6.09 Hz, 4H), 6.90–6.97 (m, 2H), 7.61–7.68 (m, 2H); MS (ES) m/z 323.3 (MH$^+$); HRMS for $C_{16}H_{22}N_2O_3S$: 323.1398.

INTERMEDIATE 36

4-(1,4-Dioxa-8-aza-spiro[4.5]dec-8-yl)-N-isobutyl-benzenesulfonamide

The title compound was prepared with 4-fluoro-n-isobutyl-benzenesulfonamide according to the procedure of Intermediate 37 as a light yellow solid; $^1$H NMR (CDCl$_3$) δ 0.86–0.89 (m, 6H), 1.78 (t, J=5.76 Hz, 4H), 2.69–2.82 (m, 3H), 2.95 (s, 1H), 3.49 (t, J=5.79 Hz, 4H), 4.00 (s, 4H), 6.88–6.94 (m, 2H), 7.66–7.71 (m, 2H); MS (ES) m/z 355.3 (MH$^+$).

INTERMEDIATE 37

N-Cyclopropylmethyl-4-(1,4-dioxa-8-aza-spiro[4.5]dec-8-yl)-benzenesulfonamide

A mixture of 2.5 g (11 mmol) n-cyclopropylmethyl-4-fluoro-benzene-sulfonamide, 1.87 g (13 mmol) 1,4-dioxa-8- azaspiro[4,5]decane and 1.81 g (13 mmol) potassium carbonate was heated at 65° C. in 6 mL 1,3-dimethyl-3,4,5,6-tetrahydro-2(1H)-pyrimidinone and 3 mL acetonitrile overnight. The reaction mixture was quenched with water and extracted twice with ethyl acetate. The organic layer was then washed twice with 1N HCl, twice with water, dried over sodium sulfate and then concentrated in vacuo. After drying overnight on a vacuum line, 3.33 g of the title compound was isolated as a yellow solid; $^1$H NMR (CDCl$_3$) δ 0.51 (m, 2H), 0.81–0.94 (m, 2H), 1.80 (t, J=5.85 Hz, 4H), 2.77–2.84 (m, 2H), 2.92 (s, 1H), 3.48 (t, J=5.76 Hz, 4H), 4.00 (s, 4H), 4.32–4.37 (m, 1H), 6.88–6.93 (m, 2H), 7.66–7.71 (m, 2H); MS (ES) m/z 353.3 (MH$^+$); HRMS for C$_{17}$H$_{24}$N$_2$O$_4$S: 353.1539.

INTERMEDIATE 38

{(4-(1,4-Dioxa-8-aza-spiro[4.5]dec-8-yl)-benzenesulfonyl]-methyl-amino}-acetic Acid Ethyl Ester The title compound was prepared with [(4-fluoro-benzenesulfonyl)-methyl-amino]-acetic acid ethyl ester according to the procedure of Intermediate 37 as a red oil; $^1$H NMR (CDCl$_3$) δ 1.25 (t, J=5.58 Hz, 3H), 1.80 (t, J=5.85 Hz, 3H), 2.84 (s, 1H), 2.92 (s, 1H), 3.53 (m, 4H), 3.92 (s, 3H), 4.00 (s, 4H), 4.13 (q, J=5.22 Hz, 2H), 6.88–6.95 (m, 2H), 7.58–7.67 (m, 2H); MS (ES) m/z 399.2 (MH$^+$); HRMS for C$_{18}$H$_{26}$N$_2$O$_6$S: 399.1585.

INTERMEDIATE 39

N-isobutyl-4-(4-oxo-piperidin-1-yl)-benzenesulfonamide

The title compound was prepared with 4-(1,4-dioxa-8-aza-spiro[4.5]dec-8-yl)-N-isobutyl-benzenesulfonamide according to the procedure of Intermediate 40 as an beige solid; $^1$H NMR (CDCl$_3$) δ 0.87 (d, J=6.72 Hz, 6H), 1.63–1.81 (m, 1H), 2.59 (t, J=6.15 Hz, 4H), 2.75 (q, J=6.75 Hz, 2H), 2.92 (s, 1H), 3.75 (t, J=6.09 Hz, 4H), 6.86–6.97 (m, 2H), 7.70–7.78 (m, 2H); MS (ES) m/z 311.3 (MH$^+$); HRMS for C$_{15}$H$_{22}$N$_2$O$_3$S: 311.1420.

INTERMEDIATE 40

N-Cyclopropylmethyl-4-(4-oxo-piperidin-1-yl)-benzenesulfonamide

A solution of 3 g (8.5 mmol) n-cyclopropylmethyl-4-(1,4-dioxa-8-aza-spiro[4.5]dec-8-yl)-benzenesulfonamide in 40 mL acetone and 40 mL 10% sulfuric acid in water was stirred for 3 days. The solvent was removed in vacuo and the resulting mix was quenched with water and neutralized with 10% sodium carbonate. The aqueous mixture was extracted twice with methylene chloride. The organic layer was dried over magnesium sulfate and concentrated in vacuo. The resulting solid was then triturated with hexanes and ether. After drying via high vacuum, 2.56 g of the title compound was isolated as a beige solid; $^1$H NMR (CDCl$_3$) δ 0.81–0.97 (m, 2H), 1.26 (s, 1H), 2.59 (t, J=6.15 Hz, 4H), 2.77–2.87 (m, 4H), 2.92 (s, 1H), 3.75 (t, J=6.06 Hz, 4H), 6.89–6.96 (m, 2H), 7.73–7.78 (m, 2H); MS (ES) m/z 309.3 (MH$^+$); HRMS for C$_{15}$H$_{20}$N$_2$O$_3$S: 309.1251.

INTERMEDIATE 41

{Methyl-[4-(4-oxo-piperidin-1-yl)-benzenesulfonyl]-amino}-acetic Acid

The title compound was prepared with {[4-(1,4-dioxa-8-aza-spiro[4.5]dec-8-yl)-benzenesulfonyl]-methyl-amino}-acetic acid ethyl ester according to the procedure of Intermediate 40 as a red gum; $^1$H NMR (CDCl$_3$) δ 2.61 (t, J=6.12 Hz, 4H), 2.87 (s, 1H), 2.92 (s, 1H), 3.77 (t, J=6.09 Hz, 4H), 3.97 (s, 2H), 6.91–6.99 (m, 2H), 7.69–7.73 (m, 2H; MS (ES) m/z 327.2 (MH$^+$); HRMS for C$_{14}$H$_{18}$N$_2$O$_5$S: 327.1019.

INTERMEDIATE 42

{Methyl-[4-(4-oxo-piperidin-1-yl)-benzenesulfonyl]-amino}-acetic Acid Ethyl Ester A solution of 0.53 g (1.6 mmol) {methyl-[4-(4-oxo-piperidin-1-yl)-benzenesulfonyl]-amino}-acetic acid in 8 mL anhydrous tetrahydrofuran was treated with 0.32 g (2.0 mmol) 1,1'-carbonyl-diimidazole. After stirring for 45 minutes, 1 mL of ethanol was added. The resulting mixture was then permitted to stir overnight. The solvent was removed in vacuo and the residue was dissolved in ethyl acetate. The organics were washed twice with saturated sodium bicarbonate, twice with water, dried over sodium sulfate and concentrated in vacuo. After drying via high vacuum overnight, 0.76 g of the title compound was isolated as a red solid; $^1$H NMR (CDCl$_3$) δ 1.23–1.29 (m, 3H), 2.59 (t, J=6.15 Hz, 4H), 2.87 (s, 1H), 3.76 (t, J=6.09 Hz, 4H), 3.96 (s, 2H), 4.11–4.18 (m, 2H), 6.89–6.96 (m, 2H), 7.67–7.75 (m, 2H); MS (ES) m/z 355.3 (MH$^+$); HRMS for C$_{16}$H$_{22}$N$_2$O$_5$S: 355.1332.

INTERMEDIATE 43

{Butyl-[4-(4-oxo-piperidin-1-yl)-benzenesulfonyl]-amino}-acetic Acid Ethyl Ester The title compound was prepared with N-butyl-4-(4-oxo-piperidin-1-yl)-benzenesulfonamide and ethyl bromoacetate according to the procedure of Intermediate 2 as a yellow oil; $^1$H NMR (CDCl$_3$) δ 0.88 (t, J=7.29 Hz, 3H), 1.23 (t, J=7.11 Hz, 3H), 1.19–1,35 (m, 2H), 1.48–1.56 (m, 2H), 2.58 (t, J=6.18 Hz, 4H), 3.20 (t, J=7.47 Hz, 2H), 3.47 (t, J=6.09 Hz, 4H), 4.03 (s, 2H), 4.13 (q, J=7.14 Hz, 2H), 6.89–6.95 (m, 2H), 7.72–7.78 (m, 2H); MS (ES) m/z 397.2 MH$^+$); HRMS for C$_{19}$H$_{28}$N$_2$O$_5$S: 397.1791.

INTERMEDIATE 44

4-(1,4-Dioxa-8-aza-spiro[4.5]dec-8-yl)-N-isopropyl-benzenesulfonamide

The title compound was prepared with 4-fluoro-N-isopropyl-benzenesulfonamide according to the procedure of Intermediate 37 as a colorless oil; $^1$H NMR (CDCl$_3$) δ 1.06 (d, J=6.54 Hz, 6H), 1.81 (t, J=5.85 Hz, 4H), 1.92–2.01 (m, 1H), 2.92 (s, 1H), 3.35 (t, J=5.94 Hz, 4H), 4.00 (s, 4H), 6.89–6.94 (m, 2H), 7.68–7.72 (m, 2H); MS (ES) m/z 341.2 (MH$^+$); HRMS for C$_{16}$H$_{24}$N$_2$O$_4$S: 341.1526.

INTERMEDIATE 45

{Cyclopropylmethyl-[4-(4-oxo-piperidin-1-yl)-benzenesulfonyl]-amino}-acetic Acid Ethyl Ester The title compound was prepared with n-cyclopropylmethyl-4-(4-oxo-piperidin-1-yl)-benzenesulfonamide and ethyl bromoacetae according to the procedure of Intermediate 2 as a yellow oil; $^1$H NMR (CDCl$_3$) δ 0.10 (m, 2H), 0.50–0.54 (m, 2H), 0.82–0.94 (m, 1H), 1.23 (t, J=7.14 Hz, 3H), 2.58 (t, J=6.18 Hz, 4H), 3.13 (d, J=6.96 Hz, 2H), 3.74 (t, J=6.09 Hz, 4H), 4.13 (q, J=7.14 Hz, 2H), 4.21 (s, 2H), 6.89–6.94 (m, 2H), 7.73–7.78 (m, 2H); MS (ES) m/z 3.95 (MH$^+$); HRMS for C$_{19}$H$_{26}$N$_2$O$_5$S: 395.1578.

INTERMEDIATE 46

{Isobutyl-[4-(4-oxo-piperidin-1-yl)-benzenesulfonyl]-amino}-acetic Acid Ethyl Ester The title compound was prepared with N-isobutyl-4-(4-oxo-piperidin-1-yl)-benzenesulfonamide and ethyl bromoacetae according to the procedure of Intermediate 2 as a yellow oil; $^1$H NMR (CDCl$_3$) δ 0.90 (d, J=7.29 Hz, 6H), 1.22 (t, J=7.11 Hz, 3H), 1.72–1.89 (m, 1H), 2.58 (t, J=6.12 Hz, 4H), 3.02 (d, J=7.53 Hz, 2H), 3.74 (t, J=6.06 Hz, 4H), 4.00 (s, 4H), 4.11 (q, J=7.14 Hz, 2H), 6.89–6.96 (m, 2H), 7.70–7.76 (m, 2H); MS (ES) m/z 397.2 (MH$^+$); HRMS for C$_{19}$H$_{26}$N$_2$O$_5$S: 397.1702.

INTERMEDIATE 47

N-Isopropyl-4-(4-oxo-piperidin-1-yl)-benzenesulfonamide

The title compound was prepared with 4-(1,4-dioxa-8-aza-spiro[4.5]dec-8-yl)-N-isopropyl-benzenesulfonamide according to the procedure of Intermediate 40 as a white solid; mp 103–105° C.; $^1$H NMR (CDCl$_3$) δ 1.09 (d, J=6.48 Hz, 6H), 2.59 (t, J=6.18 Hz, 4H), 3.36–3.43 (m, 1H), 3.47–3.54 (m, 1H), 3.75 (t, J=6.09 Hz, 4H), 6.89–6.96 (m, 2H), 7.71–7.79 (m, 2H); MS (ES) m/z 297.2 (MH$^+$); HRMS for C$_{14}$H$_{20}$N$_2$O$_3$S: 296.1196.

INTERMEDIATE 48

1-(4-Fluoro-benzenesulfonyl)-pyrrolidine-(2R)-2-carboxylic Acid Ethyl Ester

To 5 g (43 mmol) of D-proline in 20 g (434 mmol) ethanol was added 100 mL 1N HCl in ether. (mixture should become homogenous over time) After stirring for 3 days, the solvent was removed in vacuo. The residue was then dissolved in methylene chloride, which was then treated with 12 mL (86 mmol) of triethylamine. After 15 minutes, 8.45 g (43 mmol) of 4-fluoro-benzenesulfonyl chloride was added and the resulting mixture was stirred overnight. The reaction mixture was quenched with water and the organic layer was washed twice with saturated sodium carbonate, twice with 1N HCl and twice with water. After drying over magnesium sulfate, the organics were concentrated in vacuo and dried via high vacuum to give 11.56 g of the title compound as a white solid; mp 62–63° C.; $^1$H NMR (CDCl$_3$) δ 1.26 (t, J=7.11 Hz, 3H), 1.81–1.86 (m, 1H), 1.95–2.17 (m, 2H), 3.32–3.48 (m, 2H), 4.08–4.24 (m, 2H), 4.37 (q, J=3.99 Hz, 2H), 7.15–7.23 (m, 2H), 7.88–7.98 (m, 2H); MS (ES) m/z 302.3 (MH$^+$); HRMS for C$_{13}$H$_{16}$FNO$_4$S: 302.2934.

INTERMEDIATE 49

1-(4-Fluoro-benzenesulfonyl)-pyrrolidine-2-carboxylic Acid Ethyl Ester

The title compound was prepared with DL-proline according to the procedure of Intermediate 48 as a white semi-solid; $^1$H NMR (CDCl$_3$) δ 1.26 (t, J=7.11 Hz, 3H), 1.81–1.85 (m, 1H), 1.95–2.13 (m, 2H), 3.32–3.48 (m, 2H), 4.08–4.24 (m, 2H), 4.34 (q, J=4.47 Hz, 2H), 7.15–7.23 (m, 2H), 7.89–7.96 (m, 2H); MS (ES) m/z 302.3 (MH$^+$); HRMS for C$_{13}$H$_{16}$FNO$_4$S: 302.0830.

INTERMEDIATE 50

1-(4-Fluoro-benzenesulfonyl)-pyrrolidine-(2S)-2-carboxylic Acid Ethyl Ester

The title compound was prepared with L-proline according to the procedure of Intermediate 48 as a white solid; mp 58–59° C.; $^1$H NMR (CDCl$_3$) δ 1.26 (t, J=7.14 Hz, 3H), 1.81–1.85 (m, 1H), 1.95–2.11 (m, 2H), 3.31–3.48 (m, 2H), 4.09–4.24 (m, 2H), 4.34 (q, J=4.41 Hz, 2H), 7.15–7.23 (m, 2H), 7.88–7.98 (m, 2H); MS (ES) m/z 302.3 (MH$^+$); HRMS for C$_{13}$H$_{16}$FNO$_4$S: 302.0855.

INTERMEDIATE 51

1-(4-(1,4-Dioxa-8-aza-spiro[4.5]dec-8-yl)-benzenesulfonyl]-pyrrolidine-(2R)-2-carboxylic Acid Ethyl Ester The title compound was prepared with 1-(4-fluoro-benzenesulfonyl)-pyrrolidine-(2R)-2-carboxylic acid ethyl ester ( ) according to the procedure of Intermediate 37 as a yellow oil; $^1$H NMR (CDCl$_3$) δ 1.27 (t, J=7.14 Hz, 3H), 1.76–1.81 (m, 4H), 1.92–1.99 (m, 4H), 3.22–3.31 (m, 3H), 3.42–3.51 (m, 4H), 4.00 (s, 4H), 4.18 (q, J=4.80 Hz, 2H), 6.91 (d, J=9.03 Hz, 2H), 7.68–7.74 (m, 2H); MS (ES) m/z 425.3 (MH$^+$); HRMS for C$_{20}$H$_{28}$N$_2$O$_6$S: 425.1685.

INTERMEDIATE 52

1-[4-(1,4-Dioxa-8-aza-spiro[4.5]dec-8-yl)-benzenesulfonyl]-pyrrolidine-2-carboxylic Acid Ethyl Ester The title compound was prepared with 1-(4-fluoro-benzenesulfonyl)-pyrrolidine-2-carboxylic acid ethyl ester according to the procedure of Intermediate 37 as a yellow oil; $^1$H NMR (CDCl$_3$) δ 1.23–1.29 (m, 3H), 1.78–1.83 (m, 4H), 1.92–2.06 (m, 4H), 3.22–3.32 (m, 3H), 3.44–3.50 (m, 4H), 4.00 (s, 4H), 4.16–4.20 (m, 2H), 6.88–6.94 (m, 2H), 7.68–7.75 (m, 2H); MS (ES) m/z 425.2 (MH$^+$); HRMS for C$_{20}$H$_{28}$N$_2$O$_6$S: 425.1661.

INTERMEDIATE 53

1-[4-(4-Oxo-piperidin-1-yl)-benzenesulfonyl]-pyrrolidine-(2R)-2-carboxylic Acid Ethyl Ester The title compound was prepared with 1-[4-(1,4-dioxa-8-aza-spiro[4.5]dec-8-yl)-benzenesulfonyl]-pyrrolidine-(2R)-2-carboxylic acid ethyl ester according to the procedure of Intermediate 40 as a yellow oil; $^1$H NMR (CDCl$_3$) δ 1.27 (t, J=7.14 Hz, 3H), 1.76–1.81 (m, 1H), 1.94–2.10 (m, 2H), 2.61 (t, J=7.44 Hz, 4H), 3.23–3.36 (m, 2H), 3.44–3.49 (m, 2H), 4.17–4.22 (m, 2H), 6.91–6.96 (m, 2H), 7.75–7.81 (m, 2H); MS (ES) m/z 381.2 (MH$^+$); HRMS for C$_{18}$H$_{24}$N$_2$O$_5$S: 380.1398.

INTERMEDIATE 54

1-[4-(1,4-Dioxa-8-aza-spiro[4.5]dec-8-yl)-benzenesulfonyl]-pyrrolidine-(2S)-2-carboxylic Acid Ethyl Ester The title compound was prepared with 1-(4-fluoro-benzenesulfonyl)-pyrrolidine-(2S)-2-carboxylic acid ethyl ester according to the procedure of Intermediate 37 as a light yellow semi-solid; $^1$H NMR (CDCl$_3$) δ 1.26 (t, J=7.11 Hz, 3H), 1.83 (t, J=5.76 Hz, 4H), 1.92–2.01 (m, 3H), 3.25 (t, J=5.94, 4H), 3.42–3.51 (m, 2H), 4.00 (s, 4H), 4.14–4.21 (m, 4H), 6.94 (d, J=8.97 Hz, 2H), 7.71 (d, J=11.94 Hz, 2H); MS (ES) m/z 425.2 (MH$^+$); HRMS for C$_{20}$H$_{28}$N$_2$O$_6$S: 424.1699.

INTERMEDIATE 55

1-[(4-(4-Oxo-piperdin-1-yl)-benzenesulfonyl]-pyrrolidine-2-carboxylic Acid Ethyl Ester The title compound was prepared with 1-[4-(1,4-dioxa-8-aza-spiro[4.5]dec-8-yl)-benzenesulfonyl]-pyrrolidine-2- carboxylic acid ethyl ester according to the procedure of Intermediate 40 as a light orange oil; $^1$H NMR (CDCl$_3$) δ 1.22–1.29 (t, 3H), 1.77–1.80 (m, 4H), 2.59 (t, J=6.18 Hz, 4H), 3.25–3.37 (m, 3H), 3.75 (t, J=6.09 Hz, 4H), 4.13–4.22 (m, 2H), 6.90–6.96 (m, 2H), 7.74–7.81 (m, 2H); MS (ES) m/z 381.2 (MH$^+$); HRMS for C$_{18}$H$_{24}$N$_2$O$_5$S: 380.9760

INTERMEDIATE 56

1-[4-(4-Oxo-piperidin-1-yl)-benzenesulfonyl]-pyrrolidine-(2S)-2-carboxylic Acid Ethyl Ester The title compound was prepared with 1-[4-(1,4-dioxa-8-aza-spiro[4.5]dec-8-yl)-benzenesulfonyl]-pyrrolidine-(2S)-2-carboxylic acid ethyl ester according to the procedure of Intermediate 40 as an orange oil; $^1$H NMR (CDCl$_3$) δ 1.27 (t, J=7.11 Hz, 3H), 1.92–2.01 (m, 3H), 2.61 (t, J=6.42 Hz, 4H), 3.24 (t, J=5.91 Hz, 3H), 3.75 (t, J=6.12 Hz, 4H), 4.14–4.23 (m, 2H), 6.91–6.96 (m, 2H), 7.75–7.83 (m, 2H); MS (ES) m/z 381.3 (MH$^+$); HRMS for C$_{18}$H$_{24}$N$_2$O$_5$S: 380.9760.

INTERMEDIATE 57

(2S)-2-(4-Fluoro-benzenesulfonylamino)-4-methyl-pentanoic Acid Ethyl Ester

The title compound was prepared with L-leucine ethyl ester hydrochloride and 2.5 equivalents of triethylamine according to the procedure of Intermediate 33 as a colorless oil; $^1$H NMR (CDCl$_3$) δ 0.88–0.93 (m, 6H), 1.11 (t, J=7.14 Hz, 4H), 1.51 (t, J=7.53 Hz, 1H), 1.73–1.87 (m, 1H), 3.84–3.99 (m, 2H), 5.10 (d, J=9.99 Hz, 1H), 7.12–7.20 (m, 2H), 7.80–7.89 (m, 2H); MS (ES) m/z 318.2 (MH$^+$); HRMS for C$_{14}$H$_{20}$FNO$_4$S: 317.109.

INTERMEDIATE 58

(2S)-2-(4-Fluoro-benzenesulfonylamino)-3-methyl-butyric Acid Ethyl Ester

The title compound was prepared with L-valine ethyl ester hydrochloride and 2.5 equivalents of triethylamine according to the procedure of Intermediate 33 as a white solid; $^1$H NMR (CDCl$_3$) δ 0.87 (d, J=6.87 Hz, 3H), 0.97 (d, J=6.78 Hz, 3H), 1.10 (t, J=7.14 Hz, 4H), 1,97–2.13 (m, 1H), 3.71 (q, J=4.92 Hz, 1H), 3.74–4.01 (m, 2H), 5.10 (d, J=10.02 Hz, 1H), 7.12–720 (m, 2H), 7.81–7.88 (m, 2H); MS (ES) m/z 304.1 (MH$^+$); HRMS for C$_{13}$H$_{18}$FNO$_4$S: 303.00953.

INTERMEDIATE 59

Ethyl (2S)-2-({[4-(1,4-Dioxa-8-azaspiro[4.5]dec-8-yl)phenyl]sulfonyl}amino)-4-methylpentanoate The title compound was prepared with (2S)-2-(4-fluoro-benzenesulfonylamino)-4-methylpentanoic acid ethyl ester according to the procedure of Intermediate 37 as a yellow oil; $^1$H NMR (CDCl$_3$) δ 0.87–0.91 (m, 3H), 1.07–1.13 (m, 4H), 1.48 (t, J=7.23 Hz, 4H), 3.49 (t, J=5.67, 4H), 3.81–3.92 (m, 8H), 4.00 (s, 4H), 4.96 (d, J=10.08 Hz, 1H), 6.86–6.91 (m, 2H), 7.62–7.67 )m, 2H); MS (ES) m/z 441.3 (MH$^+$); HRMS for C$_{21}$H$_{32}$N$_2$O$_6$S: 440.1984.

INTERMEDIATE 60

Ethyl (2S)-2-({[4-(1,4-Dioxa-8-azaspiro[4.5]dec-8-yl)phenyl]sulfonyl}amino)-3-methylbutanoate The title compound was prepared with (2S)-2-(4-fluoro-benzenesulfonylamino)-3-methylbutyric acid ethyl ester according to the procedure of Intermediate 37 as a dark orange oil; $^1$H NMR (CDCl$_3$) δ 0.87 (d, J=6.81 Hz, 3H), 0.97 (d, J=6.72 Hz, 3H), 1.06–1.13 (m, 3H), 1.79 (t, J=5.67 Hz, 4H), 3.44–3.49 (m, 4H), 3.89–3.92 (m, 2H), 4.00 (s, 4H), 5.03 (d, J=10.05 Hz, 1H), 6.90 (m, J=8.76 Hz, 2H), 7.62–7.68 (m, 2H); MS (ES) m/z 427.2 (MH$^+$); HRMS for C$_{20}$H$_{30}$N$_2$O$_6$S: 426.1822.

INTERMEDIATE 61

Ethyl (2S)-4-Methyl-2-({[4-(4-oxo-1-piperidinyl)phenyl]sulfonyl}amino)pentanoate The title compound was prepared with ethy (2S)-2-({[4-(1,4-dioxa-8-azaspiro[4.5]dec-8-yl)phenyl]sulfonyl}amino)-4-methylpentanoate according to the procedure of Intermediate 40 as an orange oil; $^1$H NMR (CDCl$_3$) δ 0.87–0.93 (m, 6H), 1.11 (t, J=7.14 Hz, 3H), 1.45–1.51 (m, 2H), 1.75–1.86 (m, 2H), 2.57 (t, J=6.15 Hz, 4H), 3.73 (t, J=6.09 Hz, 4H), 3.84–4.00 (m, 2H), 5.04 (d, J=10.02 Hz, 1H), 6.88–6.94 (m, 2H), 7.69–7.76 (m, 2H); MS (ES) m/z 397.2 (MH$^+$); HRMS for C$_{19}$H$_{28}$N$_2$O$_5$S: 396.1685.

INTERMEDIATE 62

Ethyl (2S)-3-Methyl-2-({[4-(4-oxo-1-piperidinyl)phenyl]sulfonyl}amino)butanoate

The title compound was prepared with ethyl(2S)-2-({[4-(1,4-dioxa-8-azaspiro[4.5]dec-8-yl)phenyl]sulfonyl}amino)-3-methylbutanoate according to the procedure of Intermediate 40 as an orange solid; mp 77–80° C.; $^1$H NMR (CDCl$_3$) δ 0.87 (d, J=6.81 Hz, 3H), 0.98 (d, J=6.78 Hz, 3H), 1.10 (t, J=7.14 Hz, 3H), 2.00–2.10 (m, 2H), 2.57 (t, J=6.15 Hz, 4H), 3.73 (t, J=6.09 Hz, 4H), 3.88–4.00 (m, 2H), 5.04 (d, J=10.02 Hz, 1H), 6.87–6.92 (m, 2H), 7.60–7.75 (m, 2H); MS (ES) m/z 383.3 (MH$^+$); HRMS for C$_{18}$H$_{26}$N$_2$O$_5$S: 383.1633.

INTERMEDIATE 63

Ethyl 1-{[(4-Fluorophenyl)sulfonyl]amino}cyclohexanecarboxylate

The title compound was prepared with 1-aminocyclohexanecarboxylic acid, with gentle warming to get the mixture homogenous, according to the procedure of Intermediate 48 as a white solid; mp 96–98° C.; $^1$H NMR (CDCl$_3$) δ 61.23 (t, J=7.17 Hz, 3H), 1.26–1.46 (m, 6H), 1.82–1.87 (m, 4H), 4.00 (q, J=7.11 Hz, 2H), 4.79 (s, 1H), 7.12–7.21 (m, 2H), 7.85–7.92 (m, 2H); MS (ES) m/z 330.2 (MH$^+$); HRMS for C$_{15}$H$_{20}$FNO$_4$S: 329.1082.

INTERMEDIATE 64

Ethyl 1-{[(4-Fluorophenyl)sulfonyl]amino}cyclopentanecarboxylate

The title compound was prepared with 1-aminocyclopentanecarboxylic acid, with gentle warming to get the mixture homogenous, according to the procedure of Intermediate 48 as a white solid; $^1$H NMR (CDCl$_3$) δ 1.23 (t, J=7.14 Hz, 3H), 1.62–1.71 (m, 4H) 1.90–1.98 (m, 2H), 2.03–2.11 (m, 2H), 4.04 (q, J=7.14 Hz, 2H), 5.09 (s, 1H), 7.12–7.21 (m, 2H), 7.85–7.92 (m, 2H); MS (ES) m/z 316.2 (MH$^+$); HRMS for C$_{14}$H$_{18}$FNO$_4$S: 315.0932.

INTERMEDIATE 65

Ethyl 1-({[4-(1,4-Dioxa-8-azaspiro[4.5]dec-8)phenyl]sulfonyl}amino)-cyclopentanecarboxylate The title compound was prepared with ethyl 1-{[(4-fluorophenyl)sulfonyl]-amino}cyclopentanecarboxylate according to the procedure of Intermediate 37 as a light yellow solid; $^1$H NMR (CDCl$_3$) δ 61.21 (t, J=7.14 Hz, 3H), 1.64–1.69 (m, 4H), 1.79 (t, J=5.7 Hz, 4H), 1.90–2.10 (m, 2H), 6H), 3.48 (t, J=5.79 Hz, 4H), 3.97–4.04 (m, 2H), 4.00 (s, 4H), 4.99 (s, 1H), 6.85–6.91 (m, 2H), 7.60–7.71 (m, 2H); MS (ES) m/z 439.2 (MH$^+$); HRMS for C$_{21}$H$_{30}$N$_2$O$_6$S: 438.1812.

INTERMEDIATE 66

Ethyl 1-({[4-(4-Oxo-1-piperidinyl)phenyl] sulfonyl}amino)cyclopentanecarboxylate The title compound was prepared with ethyl 1-({[4-(1,4-dioxa-8-azaspiro[4.5-dec-8-phenyl]sulfonyl}amino) cyclopentanecarboxylate according to the procedure of Intermediate 40 as a yellow gum; $^1$H NMR (CDCl$_3$) δ 1.24 (t, J=7.14 Hz, 3H), 1.57–1.69 (m, 4H), 1.90–1.96 (m, 2H), 1.97–2.11 (m, 2H), 2.58 (t, J=6.09 Hz, 4H), 3.74 (t, J=6.06 Hz, 4H), 4.04 q, J=7.14 Hz, 2H), 5.03 (s, 1H), 6.86–6.93 (m, 2H), 7.72–7.78 (m, 2H); MS (ES) m/z 395.2 (MH$^+$); HRMS for C$_{19}$H$_{26}$N$_2$O$_5$S: 395.1631.

INTERMEDIATE 67 ethyl 1-({[4-(1,4-Dioxa-8-azaspiro[4.5]dec-8-l) phenyl]sulfonyl}amino)cyclohexanecarboxylate The title compound was prepared with ethyl 1-{[(4-fluorophenyl)sulfonyl]-amino}cyclohexanecarboxylate according to the procedure of Intermediate 37 as a yellow gum; $^1$H NMR (CDCl$_3$) δ 1.20–1.29 (m, 3H), 1.44–1.47 (m, 8H), 1.77–1.85 (m, 6H), 3.48 (t, J=5.7 Hz, 4H), 3.98 (q, J=7.59 Hz, 2H), 4.00 (s, 4H), 4.72 (s, 1H), 6.85–6.91 (m, 2H), 7.65–7.71 (m, 2H); MS (ES) m/z 453.2 (MH$^+$); HRMS for C$_{22}$H$_{32}$N$_2$O$_6$S: 453.2054.

INTERMEDIATE 68

Ethyl 1-({[4-(4-Oxo-1-piperidinyl)phenyl] sulfonyl}amino)cyclohexanecarboxylate

The title compound was prepared with ethyl 1-({[4-(1,4-dioxa-8-azaspiro[4.5]dec-8-l)phenyl]sulfonyl}amino) cyclohexanecarboxylate according to the procedure of Intermediate 40 as a white solid; $^1$H NMR (CDCl$_3$) δ 1.23 (t, J=7.11 Hz, 3H), 1.26–1.47 (m, 6H), 1.83–1.87 (m, 4H), 2.58 (t, J=6.12 Hz, 4H), 3.74 (t, J=6.03 Hz, 4H), 4.01 (q, J=7.14 Hz, 2H), 4.75 (s, 1H), 7.12–7.21 (m, 2H), 7.85–7.92 (m, 2H); MS (ES) m/z 409.3 (MH$^+$); HRMS for C$_{20}$H$_{28}$N$_2$O$_5$S: 409.1788.

INTERMEDIATE 69

Ethyl (Isopropyl{[4-(4-oxo-1-piperidinyl)phenyl] sulfonyl}amino)acetate

The title compound was prepared with N-isopropyl-4-(4-oxo-piperidin-1-yl)-benzenesulfonamide according to the procedure of Intermediate 2 as a yellow oil; $^1$H NMR (CDCl$_3$) δ 1.02–1.10 (m, 6H), 1.25–1.33 (m, 3H), 2.56–2.61 (m, 4H), 3.38–3.50 (m, 1H), 3.74 (t, J=6.06 Hz, 4H), 3.89–3.97 (m, 2H), 4.16–4.28 (m, 2H), 6.89–7.18 (m, 2H), 7.71–7.79 (m, 1H), 7.86–7.91 (m, 1H); MS (ES) m/z 383.3 (MH$^+$); HRMS for C$_{18}$H$_{26}$N$_2$O$_5$S: 383.1630.

INTERMEDIATE 70

N-Benzyl-4-(4-oxo-piperidin-1-yl)-benzenesulfonamide

The title compound was prepared from Intermediate 8, N-Benzyl-N-(tert-butylcarbonyl)-4-(1,4-dioxa-8-aza-spiro [4.5]dec-8-yl)benzenesulfonamide, according to the procedure of Intermediate 5 as a white solid; mp 136–140° C.; MS (ES) m/z 345.0 (MH$^+$); HRMS (EI) for C$_{18}$H$_{20}$N$_2$O$_3$S: 344.1166.

INTERMEDIATE 71

(3,4-Dimethoxyphenyl)[(4-fluorophenyl)sulfonyl] carbamic Acid, tert-Butyl Ester

The title compound was prepared from Intermediate 1, N-(3,4-dimethoxy-phenyl)-4-fluoro-benzenesulfonamide, according to the procedure of Intermediate 6 as a tan solid; mp 99–102° C.; MS (ES) m/z 412.0 (MH$^+$); HRMS (EI) for C$_{19}$H$_{22}$FNO$_6$S: 344.1166.

INTERMEDIATE 72

(3,4-Dimethoxyphenyl)[[4-(1,4-dioxa-8-azaspiro [4.5]dec-8-yl)phenyl]sulfonyl]carbamic Acid, tert-Butyl Ester The title compound was prepared from Intermediate 71, (3,4-dimethoxy-phenyl)[(4-fluorophenyl)sulfonyl]carbamic acid, tert-butyl ester, according to the procedure of Intermediate 3 as a gum; MS (ES) m/z 434.9 (M-BOC+H$^+$).

INTERMEDIATE 73

N-(3,4-Dimethoxy-phenyl)-4-(4-oxo-piperidin-1-yl)-benzenesulfonamide

The title compound was prepared from Intermediate 72, (3,4-dimethoxyphenyl)-[[4-(1,4-dioxa-8-azaspiro[4.5]dec-8-yl)phenyl]sulfonyl]carbamic acid, tert-butyl ester, according to the procedure of Intermediate 5 as a yellow solid; mp 50–56° C.; MS (ES) m/z 391.0 (MH$^+$); HRMS (EI) for C$_{19}$H$_{22}$N$_2$O$_5$S: 390.1246.

The following procedures describe the preparation of representative examples of this invention.

EXAMPLE 1

N-Benzyl-N-(3,4-dimethoxy-phenyl)-4-{4-[2-hydroxy-3-(2-oxo-2,3-dihydro-1H-benzoimidazol-4-yloxy)-propylamino]-piperidin-1-yl}-benzenesulfonamide Sodium Triacetoxyborohydride (0.015 g, 0.72 mM) was added to a solution of 4-((2S)-3-Amino-2-hydroxy-propoxy)-1,3-dihydro-benzoimidazol-2-one(0.08 g, 0.36 mM), N-Benzyl-N-(3,4-dimethoxy-phenyl)- 4-(4-oxo-piperidin-1-yl)-benzenesulfonamide (0.19 g, 0.39 mM), and acetic acid (0.025 ml, 0.43 mM) in anhydrous dimethylforamide (5 ml). The reaction was stirred overnight. The reaction was quenched with 50% H$_2$O/sat. NaHCO$_3$aq. (20 ml). The solids were captured on a filter and washed with ethyl acetate, diethyl ether, and hexanes to afford 0.075 g of the desired product as a brown solid. $^1$H NMR (DMSO) δ 1.31 (m, 2H), 1.89 (m, 2H), 2.71 (m, 2H), 2.87 (m, 3H), 3.53(s, 3H), 3.67 (s, 3H), 3.87 (m, 4H), 3.98 (m, 1H), 4.67(s, 2H), 4.95(bs, 1H), 6.44 (s, 1H), 6.59(m, 2H), 6.79 (m, 2H), 7.05 (d, 2H, J=8.7 Hz), 7.25 (m, 6H), 7.41(d, 2H, J=8.4 Hz), 10.59 (bs, 1H), 10.72 (bs, 1H); MS (ES) m/z: 688.1 (MH$^+$); HRMS for C$_{36}$H$_{41}$N$_5$O$_7$S: 688.2799 (MH$^+$).

EXAMPLE 2

N-Benzyl-N-butyl-4-{4-[(2S)-2-hydroxy-3-(2-oxo-2,3-dihydro-1H-benzoimidazol-4-yloxy)-propylamino]-piperidin-1-yl}-benzenesulfonamide The title compound was prepared from 4-((2S)-3-Amino-2-hydroxy-propoxy)-1,3-dihydro-benzoimidazol-2-one and Reference Example 9 according to the procedure of Example 1 as a brown solid. ¹H NMR (DMSO) δ 0.67(t, 3H, J=7.17 Hz), 1.04(m, 2H), 1.24(m, 2H), 1.37 (m, 2H), 1.90 (m, 2H), 2.73 (m, 2H), 2.84(m, 2H), 2.99(m, 4H), 3.87(m, 3H), 4.03(M, 1H), 4.21(s, 2H), 5.07(bs, 1H), 6.61 (m, 1H), 6.84(t, 1H, J=8.1 Hz), 7.07(d, 2H, J=9.0 Hz), 7.32 (m, 6H), 7.59 (d, 2H, J=8.7 Hz), 10.59 (bs, 1H), 10.72 (bs, 1H); MS (ES) m/z: 608.3 (MH$^+$); HRMS for $C_{32}H_{41}N_5O_5S$: 608.2915 (MH$^+$).

EXAMPLE 3

N-Benzyl-N-butyl-4-{4-[2-hydroxy-2-(4-hydroxy-3-methanesulfonylamino-phenyl)-ethylamino]-piperidin-1-yl}-benzenesulfonamide The title compound was prepared from N-[5-(2-Amino-1-hydroxy-ethyl)-2-hydroxy-phenyl]-methanesulfonamide and Reference Example 9 according to the procedure of Example 1 as an off-white solid. ¹H NMR (DMSO) δ 0.67(t, 3H, J=7.08 Hz), 1.06(m, 2H), 1.22(m, 2H), 1.36 (m, 2H), 1.89 (m, 2H), 2.69 (m, 3H), 2.92(s, 3H), 2.99(m, 2H), 3.69(m, 2H), 3.85(M, 2H), 4.21(s, 2H), 4.52(m, 1H), 6.82 (d, 1H, J=11.52 Hz), 7.03(d, 2H, J=8.1 Hz), 7.19 (s, 1H), 7.32 (m, 6H), 7.61 (d, 2H, J=8.7 Hz); MS (ES) m/z 631.2 (MH$^+$); HRMS for $C_{31}H_{42}N_4O_6S_2$: 631.2626 (MH$^+$).

EXAMPLE 4

N-Benzyl-4-{4-[2-hydroxy-3-(2-oxo-2,3-dihydro-1H-benzoimidazol-4-yloxy)-propylamino]-piperidin-1-yl}-benzenesulfonamide The title compound was prepared from 4-((2S)-3-Amino-2-hydroxy-propoxy)-1,3-dihydro-benzoimidazol-2-one and Reference Example 70, N-benzyl-4-(4-oxo-piperidin-1-yl)-benzenesulfonamide, according to the procedure of Example 1 as a grey solid. ¹H NMR (DMSO) δ 1.37 (m, 2H), 1.90 (m, 2H), 2.73 (m, 2H), 2.84(m, 2H), 2.99(m, 4H), 3.87(m, 3H), 4.03(m, 1H), 5.07(bs, 1H), 6.67 (m, 1H), 6.85(t, 1H, J=8.1 Hz), 7.07(d, 2H, J=9.0 Hz), 7.32 (m, 6H), 7.59 (d, 2H, J=8.7 Hz), 10.59 (bs, 1H), 10.72 (bs, 1H); MS (ES) m/z: 552.1 (MH$^+$); HRMS for $C_{28}H_{33}N_5O_5S$: 552.2267 (MH$^+$).

EXAMPLE 5

N-Benzyl-4-{4-[2-hydroxy-2-(4-hydroxy-3-methanesulfonylamino-phenyl)-ethylamino]-piperidin-1-yl}-benzenesulfonamide The title compound was prepared from N-[5-(2-Amino-1-hydroxy-ethyl)-2-hydroxy-phenyl]-methanesulfonamide and Reference Example 70, N-benzyl-4-(4-oxo-piperidin-1-yl)-benzenesulfonamide, according to the procedure of Example 1 as an off-white solid. ¹H NMR (DMSO) δ 1.33 (m, 2H), 1.86 (m, 2H), 2.67(m, 3H), 2.89(s, 3H), 2.99(m, 2H), 3.69(m, 2H), 3.85(s, 2H), 4.49(m, 1H), 6.83 (d, 1H, J=6.0 Hz), 7.00(m, 2H), 7.19 (s, 1H), 7.24 (m, 6H), 7.56 (d, 2H, J=6.6 Hz); MS (ES) m/z: 575.1 (MH$^+$); HRMS for $C_{27}H_{34}N_4O_6S_2$: 575.2015 (MH$^+$).

EXAMPLE 6

N-Benzyl-4-{4-[(2S)-2-hydroxy-3-(4-hydroxy-phenoxy)-propylamino]-piperidin-1-yl}-benzenesulfonamide The title compound was prepared from 4-((2S)-3-Amino-2-hydroxy-propoxy)-phenol and Reference Example 70, N-benzyl-4-(4-oxo-piperidin-1-yl)-benzenesulfonamide, according to the procedure of Example 1 as a tan solid. ¹H NMR (DMSO) δ 1.27 (m, 2H), 1.86 (m, 2H), 2.75(m, 3H), 2.91(t, 2H, J=8.4 Hz), 3.82(m, 5H), 3.89(s, 2H), 4.89(m, 1H), 6.67 (d, J=6.6 Hz), 6.76(d, 2H, J=6.6 Hz), 7.02 (d, 2H, J=6.6 Hz), 7.26 (m, 5H), 7.57 (d, 2H, J=6.6 Hz), 7.78)bs, 1H), 8.87(bs, 1H); MS (ES) m/z: 512.1 (MH$^+$); HRMS for $C_{27}H_{33}N_3O_5S$: 511.2215 (MH$^+$).

EXAMPLE 7

N-(3,4-Dimethoxy-phenyl)-4-{4-[(2S)-2-hydroxy-3-(2-oxo-2,3-dihydro-1H-benzoimidazol-4-yloxy)-propylamino]-piperidin-1-yl}-benzenesulfonamide The title compound was prepared from 4-((2S)-3-Amino-2-hydroxy-propoxy)-1,3-dihydrobenzoimidazol-2-one and Reference Example 73, N-(3,4-dimethoxy-phenyl)-4-(4-oxo-piperidin-1-yl)-benzenesulfonamide, according to the procedure of Example 1 as a grey solid. ¹H NMR (DMSO) δ 1.28 (m, 2H), 1.84 (m, 2H), 2.65(m, 1H), 2.81 (m, 4H), 3.62(s, 3h), 3.64(s, 3H). 3.77(m, 2H), 3.89(m, 2H), 4.03(m, 1H), 4.87(bs, 1H), 6.59 (m, 4H), 6.74(d, 1H, J=8.7 Hz), 6.83(d, 1H, J=8.1 Hz), 6.91 (d, 2H, J=9.0 Hz), 7.45(d, 2H, J=9.0 Hz), 10.57 (bs, 1H), 10.69 (bs, 1H); MS (ES) m/z: 598.1 (MH$^+$); HRMS for $C_{29}H_{35}N_5O_7S$: 598.2296 (MH$^+$).

EXAMPLE 8

N-(3,4-Dimethoxy-phenyl)-4-{4-[2-hydroxy-2-(4-hydroxy-3-methanesulfonylamino-phenyl)-ethylamino]-piperidin-1-yl}-benzenesulfonamide The title compound was prepared from N-[5-(2-Amino-1-hydroxy-ethyl)-2-hydroxy-phenyl]-methanesulfonamide, and Reference Example 73, N-(3,4-dimethoxy-phenyl)-4-(4-oxo-piperidin-1-yl)-benzenesulfonamide, according to the procedure of Example 1 as a yellow solid; mp 205–218° C.; ¹H NMR (300 MHz, DMSO-d$_6$) δ 1.15–1.30 (m, 2H), 1.70–1.90 (m, 2H), 2.50–3.00 (m, 5H), 2.89 (s, 3H), 3.62 (s, 3H), 3.65 (s, 3H), 3.65–3.85 (m 2H), 4.40–4.40 (m, 1H), 6.50–7.10 (m, 8H), 7.45 (d, 2H), 9.11 (s, 1H); MS (ES) m/z: 621.0 (MH$^+$); HRMS Calcd. for $C_{28}H_{37}N_4O_8S_2$ (MH$^+$): 621.2053. Found: 621.2058.

EXAMPLE 9

4-{4-[(2S)-3-(4-Benzyloxy-phenoxy)-2-hydroxy-propylamino]-piperidin-1-yl}-N-(3,4-dimethoxy-phenyl)-benzenesulfonamide The title compound was prepared from 1-Amino-3-(4-benzyloxy-phenoxy)-propan-2-ol and Reference Example 73, N-(3,4-dimethoxy-phenyl)-4-(4-oxo-piperidin-1-yl)-benzenesulfonamide, according to the procedure of Example 1 as an off-white solid; mp 113–121° C.; ¹H NMR (300 MHz, DMSO-d$_6$) δ 1.15–1.35 (m, 2H), 1.75–1.90 (m, 2H), 5H), 2.89 (s, 3H), 3.61 (s, 3H), 3.64 (s, 3H), 3.64–3.80 (m, 5H), 5.02 (s, 2H), 6.70–7.00 (m, 9H), 7.30–7.70 (m, 7H); MS (ES) m/z: 648.1 (MH$^+$); HRMS Calcd. for $C_{35}H_{42}N_3O_7S$ (MH$^+$): 648.2743. Found: 648.2710.

EXAMPLE 10

4-{4-[(2S)-3-(9H-Carbazol-4-yloxy)-2-hydroxy-propylamino]-piperidin-1-yl}-N-(3,4-dimethoxy-phenyl)-benzenesulfonamide The title compound was prepared from 1-Amino-3-(9H-carbazol-4-yloxy)-propan-2-ol and Reference Example 73, N-(3,4-dimethoxy-phenyl)-4-(4-oxo-piperidin-1-yl)- benzenesulfonamide, according to the procedure of Example 1 as an off-white solid; mp 58–64° C.; $^1$H NMR (300 MHz, DMSO-d$_6$) δ 1.20–1.40 (m, 2H), 1.80–1.95 (m, 2H), 2.60–2.90 (m, 5H), 3.62 (s, 3H), 3.64 (s, 3H), 3.60–3.80 (m, 2H), 4.00–4.20 (m, 3H), 6.40–7.50 (m, 12H), 7.95 (s, 1H), 8.20 (d, 1H), 11.30 (s, 1H); MS (ES) m/z: 631.1 (MH$^+$); HRMS Calcd. for C$_{34}$H$_{39}$N$_4$O$_6$S (MH$^+$): 631.2590. Found: 631.2595.

EXAMPLE 11

N-(3,4-Dimethoxy-phenyl)-4-{4-[(2S)-2-hydroxy-3-(4-hydroxy-phenoxy)-propylamino]-piperidin-1-yl}-benzenesulfonamide The title compound was prepared from 4-((2S)-3-Amino-2-hydroxy-propoxy)-phenol and Reference Example 73, N-(3,4-dimethoxy-phenyl)-4-(4-oxo-piperidin-1-yl)-benzenesulfonamide, according to the procedure of Example 1 as an off-white solid; mp 101–106° C.; $^1$H NMR (300 MHz, DMSO-d$_6$) δ 1.15–1.30 (m, 2H), 1.70–1.90 (m, 2H), 2.50–2.90 (m, 5H), 3.61 (s, 3H) 3.63 (s, 3H), 3.60–3.90 (m, 5H), 6.45 (dd, 1H), 6.60–6.80 (m, 8H), 6.90 (d, 1H), 7.45 (d, 1H); MS (ES) m/z: 557.9 (MH$^+$); HRMS Calcd. for C$_{28}$H$_{36}$N$_3$O$_7$S (MH$^+$): 558.2274. Found: 558.2293.

EXAMPLE 12

N-Butyl-4-{4-[(2S)-2-hydroxy-3-(2-oxo-2,3-dihydro-1H-benzoimidazol-4-yloxy)-propylamino]-piperidin-1-yl}-benzenesulfonamide The title compound was prepared from 4-((2S)-3-amino-2-hydroxy-propoxy)-1,3-dihydro-benzoimidazol-2-one and Reference Example 11, N-butyl-4-(4-oxo-piperidin-1-yl)-benzenesulfonamide, according to the procedure of Example 1 as an off-white solid; mp 69–75° C.; $^1$H NMR (300 MHz, DMSO-d$_6$) δ 0.79 (t, 3H), 1.10–1.40 (m, 6H), 1.75–1.90 (m, 2H), 2.67 (t, 2H), 2.10–3.00 (m, 5H), 3.70–4.10 (m, 5H), 6.55 (d, 3H), 6.62 (d, 1H), 6.83 (t, 1H), 7.00 (d, 2H), 7.52 (d, 2H), 10.45–10.80 (m, 2H); MS (ES) m/z: 518.1 (MH$^+$); HRMS Calcd. for C$_{25}$H$_{36}$N$_5$O$_5$ S (MH$^+$): 518.2437. Found: 518.2446.

EXAMPLE 13

N-Butyl-4-{4-[(2S)-3-(9H-carbazol-4-yloxy)-2-hydroxy-propylamino]-piperidin-1-yl}-benzenesulfonamide The title compound was prepared from 1-amino-3-(9H-carbazol-4-yloxy)-propan-2-ol and Reference Example 11, N-butyl-4-(4-oxo-piperidin-1-yl)-benzenesulfonamide, according to the procedure of Example 1 as an off-white solid; mp 166–179° C.; $^1$H NMR (300 MHz, DMSO-d$_6$) δ 0.79 (t, 3H), 1.15–1.40 (m, 6H), 1.75–1.90 (m, 2H), 2.64 (t, 2H), 2.60–3.00 (m, 5H), 3.60–4.20 (m, 5H), 6.69 (d, 1H), 6.80–7.60 (m, 7H), 7.90 (s, 1H), 8.20 (d, 2H), 11.35 (s, 1H); MS (ES) m/z: 551.1 (MH$^+$); HRMS Calcd. for C$_{30}$H$_{39}$N$_4$O$_4$S (MH$^+$): 551.2692. Found: 551.2664.

EXAMPLE 14

N-Butyl-4-{4-[(2R)-2-hydroxy-2-(4-hydroxy-3-methanesulfonylamino-phenyl)-ethylamino]-piperidin-1-yl}-benzenesulfonamide The title compound was prepared from N-[5-((1R)-2-Amino-1-hydroxy-ethyl)-2-hydroxy-phenyl]-methanesulfonamide and Reference Example 11, N-butyl-4-(4-oxo-piperidin-1-yl)-benzenesulfonamide, according to the procedure of Example 1 as a white solid; mp 71–75° C.; $^1$H NMR (300 MHz, DMSO-d$_6$) δ 0.80 (t, 3H), 1.10–1.40 (m, 6H), 1.80–1.95 (m, 2H), 2.50–2.90 (m, 5H), 2.92 (s, 3H), 3.70–3.90 (m, 2H), 4.45–4.55 (m, 1H), 6.82 (d, 1H), 7.02 (d, 3H), 7.02 (d, 3H), 7.19 (d, 1H), 7.54 (d, 2H); MS (ES) m/z: 541.0 (MH$^+$); HRMS Calcd. for C$_{24}$H$_{37}$N$_4$O$_6$S$_2$ (MH$^+$): 541.2155. Found: 541.2136.

EXAMPLE 15

1-(4-{4-[2-Hydroxy-2-(4-hydroxy-3-methanesulfonylamino-phenyl)-ethylamino]-piperidin-1-yl}-benzenesulfonyl)-pyrrolidine-2-carboxylic Acid Isopropyl Ester The title compound was prepared from N-[5-((1R)-2-Amino-1-hydroxy-ethyl)-2-hydroxy-phenyl]-methanesulfonamide and Reference Example 14, 1-[4-(4-oxo-piperidin-1-yl)-benzenesulfonyl]-pyrrolidine-2-carboxylic acid isopropyl ester, according to the procedure of Example 1 as an off-white solid; mp 52–58° C.; $^1$H NMR (300 MHz, DMSO-d$_6$) δ 1.10–1.20 (m, 6). 1.20–1.35 (m, 2H), 1.50–2.00 (m, 6H), 2.91 (s, 3H), 2.50–3.00 (m, 7H) 3.70–3.90 (m, 2H), 4.00 (m, 1H), 4.40–4.50 (m, 1H), 4.85–5.00 (m, 1H), 6.77 (d, 1H), 6.98 (d, 1H), 7.03 (d, 2H), 7.18 (d, 1H), 7.57 (d, 2H); MS (ES) m/z: 625.1 (MH$^+$); HRMS Calcd. for C$_{28}$H$_{40}$N$_4$O$_8$S$_2$ (MH$^+$): 625.2360. Found: 625.2366.

EXAMPLE 16

1-(4-{4-[2-Hydroxy-3-(2-oxo-2,3-dihydro-1H-benzoimidazol-4-yloxy)-propylamino]-piperidin-1-yl}-benzenesulfonyl)-pyrrolidine-2-carboxylic Acid Isopropyl Ester The title compound was prepared from 4-((2S)-3-Amino-2-hydroxy-propoxy)-1,3-dihydro-benzoimidazol-2-one and Reference Example 14, 1-[4-(4-oxo-piperidin-1-yl)-benzenesulfonyl]-pyrrolidine-2-carboxylic acid isopropyl ester, according to the procedure of Example 1 as an off-white solid; mp 74–83° C.; $^1$H NMR (300 MHz, DMSO-d$_6$) δ 1.10–1.20 (m, 6H), 1.20–1.90 (m, 8H), 2.60–3.40 (m, 6H), 3.80–4.10 (m, 6H), 4.85–4.95 (m, 1H), 6.65 (d, 1H), 6.75 (d, 1H), 6.75 (d, 1H), 6.84 (t, 2H), 7.00 (d, 2H), 7.57 (d, 2H), 10.57 (br s, 1H), 10.70 (br s, 1H); MS (ES) m/z: 602.1 (MH$^+$); HRMS Calcd. for C$_{29}$H$_{40}$N$_5$O$_7$S (MH$^+$): 602.2634. Found: 602.2642.

EXAMPLE 17

1-(4-{4-[(2S)-2-Hydroxy-3-(2-oxo-2,3-dihydro-1H-benzoimidazol-4-yloxy)-propylamino]-piperidin-1-yl}-benzenesulfonyl)-pyrrolidine-2-carboxylic Acid Methylamide Reference Example 20, 1-[4-(1,4-dioxa-8-aza-spiro[4.5]dec-8-yl)-benzenesulfonyl]-pyrrolidine-2-carboxylic acid methylamide, was hydrolyzed to the corresponding ketone according to the procedure of Reference Example 5, and then reacted with 4-((2S)-3-amino-2-hydroxy-propoxy)-1,3-dihydro-benzoimidazol-2-one according to the procedure of Example 1 to give the title compound as a tan solid; mp 36–39° C.; $^1$H NMR (300 MHz, DMSO-d$_6$) δ 1.20–2.00 (m, 8H), 2.55 (d, 3H), 2.50–3.40 (m, 6H), 3.70–4.10 (m, 6H), 4.85–4.95 (m, 1H), 6.55 (d, 1H), 6.60 (d, 1H), 6.80 (t, 2H), 7.35 (d, 2H), 7.60 (d, 2H), 7.90 (q, 1H), 10.60 (br s, 1H), 10.70 (br s, 1H), MS (ES) m/z: 573.1 (MH$^+$); HRMS Calcd. for C$_{27}$H$_{37}$N$_6$O$_6$S (MH$^+$): 573.2490. Found: 573.2495.

EXAMPLE 18

1-(4-{4-[2-Hydroxy-2-(4-hydroxy-3-methanesulfonylamino-phenyl)-ethylamino]-piperidin-1-yl}-benzenesulfonyl)-pyrrolidine-2-carboxylic Acid The title compound was prepared from Example 15 according to the procedure of Example 31 as gum; MS (ES) m/z: 583.1 (MH$^+$).

EXAMPLE 19

[Butyl-(4-{4-[(2R)-2-hydroxy-2-(4-hydroxy-3-methanesulfonylamino-phenyl)-ethylamino]-piperidin-1-yl}-benzenesulfonyl)-amino]-acetic Acid Benzyl Ester The title compound was prepared from N-[5-((1R)-2-Amino-1-hydroxy-ethyl)-2-hydroxy-phenyl]-methanesulfonamide and Reference Example 18, {butyl-[4-(4-oxo-piperidin-1-yl)-benzenesulfonyl]-amino}-acetic acid benzyl ester, according to the procedure of Example 1 as a white solid; mp 59–64° C.; $^1$H NMR (300 MHz, DMSO-d$_6$) δ 0.78 (t, 3H), 1.10–1.40 (m, 6H), 1.80–1.95 (m, 2H), 2.60–3.00 (m, 5H), 2.91 (s, 3H), 3.05 (t, 2H), 3.70–3.80 (m, 2H), 4.04 (s, 2H), 4.40–4.50 (m, 1H), 5.20 (s, 2H), 6.80 (d, 1H), 6.95 (d, 2H), 7.00 (d, 2H), 7.18(d, 1H), 7.30–7.45 (m, 5H), 7.50 (d, 2H); MS (ES) m/z: 689.1 (MH$^+$).

EXAMPLE 20

[Butyl-(4-{4-[(2R)-2-hydroxy-2-(4-hydroxy-3-methanesulfonylamino-phenyl)-ethylamino]-piperidin-1-yl}-benzenesulfonyl)-amino]-acetic Acid Example 19 (0.20 g, 0.29 mmol) and a catalytic amount of 10% Pd/C in methanol (10 ml) was hydrogenated at 37 psi for 18 h. The mixture was filtered through Celite and evaporated to give 0.10 g of the title compound as an off-white solid; mp 125–138° C.; MS (ES) m/z: 599.3 (MH$^+$).

EXAMPLE 21

(2R)-1-(4-{4-[(2R)-2-Hydroxy-2-(4-hydroxy-3-methanesulfonylamino-phenyl)-ethylamino]-piperidin-1-yl}-benzenesulfonyl)-pyrrolidine-2-carboxylic Acid Benzyl Ester The title compound was prepared from N-[5-((1R)-2-Amino-1-hydroxy-ethyl)-2-hydroxy-phenyl]-methanesulfonamide and Reference Example 23, (2R)-1-[4-(4-oxo-piperidin-1-yl)-benzenesulfonyl]-pyrrolidine-2-carboxylic acid benzyl ester, according to the procedure of Example 1 as a white solid; mp 62–69° C.; $^1$H NMR (300 MHz, DMSO-d$_6$) δ 1.20–1.40 (m, 2H), 1.40–1.90 (m, 6H), 2.50–3.20 (m, 5H), 3.75–3.85 (m, 2H), 4.15 (dd, 1H), 4.40–4.50 (m, 1H), 5.19 (s, 2H), 6.80 (d, 1H), 6.92 (d, 3H), 7.15 (d, 1H), 7.40–7.50(m, 5H), 7.52 (d, 2H); MS (ES) m/z: 673.1.1 (MH$^+$).

EXAMPLE 22

(2S)-1-(4-{4-[(2R)-2-Hydroxy-2-(4-hydroxy-3-methanesulfonylamino-phenyl)-ethylamino]-piperidin-1-yl}-benzenesulfonyl)-pyrrolidine-2-carboxylic Acid Benzyl Ester The title compound was prepared from N-[5-((1R)-2-Amino-1-hydroxy-ethyl)-2-hydroxy-phenyl]-methanesulfonamide and Reference Example 22, (2S)-1-[4-(4-oxo-piperidin-1-yl)-benzenesulfonyl]-pyrrolidine-2-carboxylic acid benzyl ester, according to the procedure of Example 1 as a white solid; mp 65–71° C.; $^1$H NMR (300 MHz, DMSO-d$_6$) δ 1.20–1.40 (m, 2H), 1.40–1.90 (m, 6H), 2.50–3.20 (m, 5H), 3.75–3.85 (m, 2H), 4.15 (dd, 1H), 4.40–4.50 (m, 1H), 5.19 (s, 2H), 6.80 (d, 1H), 6.92 (d, 3H), 7.15 (d, 1H), 7.40–7.50(m, 5H), 7.52 (d, 2H); MS (ES) m/z: 673.1 (MH$^+$).

EXAMPLE 23

[Butyl-(4-{4-[(2R)-2-hydroxy-2-(4-hydroxy-3-methanesulfonylamino-phenyl)-ethylamino]-piperidin-1-yl}-benzenesulfonyl)-amino]-acetic Acid Ethyl Ester The title compound was prepared according to the procedure of Example 1 from 1.03 g (2.6 mmol) of Reference Example 43, {butyl-[4-(4-oxo-piperidin-1-yl)-benzenesulfonyl]-amino{-acetic acid ethyl ester, and 0.77 9 (3.1 mmol) of (R)-N-[5-(2-amino-1-hydroxy-ethyl)-2-hydroxy-phenyl}-methanesulfonamide, yielding 1.05 g of a light yellow solid; m.p. 94–95° C.; MS (ES) m/z 627.2 (MH$^+$); HRMS (ES) Calcd. for C$_{28}$H$_{43}$N$_4$O$_8$S$_2$ (MH$^+$): 627.2517, Found: 627.2505.

EXAMPLE 24

N-(2-Hydroxyethyl)-4-{4-[(2R)-2-hydroxy-2-(4-hydroxy-3-methanesulfonylamino-phenyl)-ethylamino]-piperidin-1-yl)-benzenesulfonamide The title compound was prepared according to the procedure of Example 1 from 0.12 g (0.4 mmol) of Reference Example 30, N-(2-hydroxyethyl)-4-(4-oxo-piperidin-1-yl)-benzenesulfonamide, and 0.12 g (0.5 mmol) of (R)-N-[5-(2-amino-1-hydroxy-ethyl)-2-hydroxy-phenyl}-methanesulfonamide, yielding 0.22 g of an off-white solid; m.p. 78–81° C.; MS (ES) m/z 529.2 (MH$^+$); HRMS (ES) Calcd. for C$_{22}$H$_{33}$N$_4$O$_7$S$_2$ (MH$^+$): 529.1785, Found: 529.1779.

EXAMPLE 25

[(4-{4-[(2R)-2-Hydroxy-2-(4-hydroxy-3-methanesulfonylamino-phenyl)-ethylamino]-piperidin-1-yl}-benzenesulfonyl)-methyl-amino]-acetic Acid Ethyl Ester The title compound was prepared from Reference Example 42 and (R)-N-[5-(2-amino-1-hydroxy-ethyl)-2-hydroxy-phenyl}-methanesulfonamide according to the procedure of Example 1 as a light brown solid; $^1$H NMR (DMSO) δ 1.15 (t, J=3.3 Hz, 3H), 1.23–1.35 (m, 2H), 1.83–1.91 (m, 2H), 2–60–2.71 (m, 5H), 2.87–2.96 (m, 3H), 2.92 (s, 3H), 3.38–3.48 (m, 2H), 3.80–3.89 (m, 5H), 4.06 (q, J=3.03 Hz, 2H), 4.48–4.52 (m, 1H), 5.37 (bs, 1H), 6.83 (d, J=8.35 Hz,1H), 6.98–7.04 (m, 3H), 7.18 (d, J=1.98 Hz, 1H), 7.52 (d, J=9.0 Hz, 2H); MS (ES) m/z 585.2 (MH$^+$); HRMS for C$_{25}$H$_{36}$N$_4$O$_8$S$_2$: 585.2034.

EXAMPLE 26

N-Cyclopropylmethyl-4-{4-[(2R)-2-hydroxy-2-(4-hydroxy-3-methanesulfonylamino-phenyl)-ethylamino]-piperidin-1-yl}-benzenesulfonamide The title compound was prepared from Reference Example 40 and (R)-N-[5-(2-amino-1-hydroxy-ethyl)-2- hydroxy-phenyl}-methanesulfonamide according to the procedure of Example 1 as a beige solid; $^1$H NMR (DMSO) δ 0.02–0.1 (m, 2H), 0.3–0.4 (m, 2H), 0.73–0.82 (m, 1H), 1.23–1.33 (m, 2H), 1.81–1.90 (m, 2H), 2.56 (d, J=6.81 Hz, 2H), 2.60–2.71 (m, 4H), 2.83–2.88 (m, 3H), 2.92 (s, 3H), 3.17 (s, 2H), 3.76–3.80 (m, 2H), 4.46–4.50 (m, 1H), 5.5 (bs, 1H), 6.82 (d, J=8.22 Hz, 1H), 6.98–7.02 (m, 3H), 7.18 (d, J=1.98 Hz, 1H), 7.53 (d, J=9.0 Hz, 2H); MS (ES) m/z 539.2 (MH$^+$); HRMS for $C_{24}H_{34}N_4O_6S_2$: 539.1985.

EXAMPLE 27

4-{4-[(2R)-2-Hydroxy-2-(4-hydroxy-3-methanesulfonylamino-phenyl)-ethylamino]-piperidin-1-yl}-N-isobutyl-benzenesulfonamide The title compound was prepared from Reference Example 39 and (R)-N-[5-(2-amino-1-hydroxy-ethyl)-2-hydroxy-phenyl}-methanesulfonamide according to the procedure of Example 1 as a beige solid; $^1$H NMR (DMSO) δ 0.79 (d, J=6.66 Hz, 6H), 1.23–1.35 (m, 2H), 1.53–1.67 (m, 1H), 1.82–1.90 (m, 2H), 2.45 (d, J=6.81 Hz, 2H), 2.59–2.72 (m, 4H), 2.84–2.88 (m, 3H), 2.92 (s, 3H), 3.17 (s, 2H), 3.77–3.81 (m, 2H), 4.47–4.51 (m, 1H), 5.4 (bs, 1H), 6.82 (d, J=8.25 Hz, 1), 6.99–7.03 (m, 3H), 7.18 (d, J=2.01 Hz, 1H), 7.53 (d, J=9.0 Hz, 2H); MS (ES) m/z 541.3 (MH$^+$); HRMS for $C_{24}H_{36}N_4O_6S_2$: 541.2138.

EXAMPLE 28

[Cyclopropylmethyl-(4-{4-[(2R)-2-hydroxy-2-(4-hydroxy-3-methanesulfonylamino-phenyl)-ethylamino]-piperidin-1-yl}-benzenesulfonyl)-amino]-acetic Acid Ethyl Ester The title compound was prepared from Reference Example 45 and (R)-N-[5-(2-amino-1-hydroxy-ethyl)-2-hydroxy-phenyl}-methanesulfonamide according to the procedure of Example 1 as a tan solid; $^1$H NMR (DMSO) δ 0.76–0.83 (m, 2H), 1.14 (t, J=7.11 Hz, 3H), 1.23–1.33 (m, 2H), 1.82–1.90 (m, 2H), 2.58–2.71 (m, 5H), 2.86–2.97 (m, 4H), 2.92 (s, 3H), 2.98 (d, J=6.9 Hz, 2H), 3.16 (s, 2H), 3.78–3.83 (m, 2H), 4.00–4.07 (m, 4H), 4.46–4.51 (m, 1H), 5.3 (bs, 1H), 6.82 (d, J=8.22 Hz, 1H), 6.97–7.03 (m, 3H), 7.18 (d, J=1.98 Hz, 1H), 7.54 (d, J=9.03 Hz, 2H); MS (ES) m/z 625.3 (MH$^+$); HRMS for $C_{28}H_{40}N_4O_8S2$: 625.2350.

EXAMPLE 29

4-{4-[(2R)-2-Hydroxy-2-(4-hydroxy-3-methanesulfonylamino-phenyl)-ethylamino]-piperidin-1-yl}-N-isopropyl-benzenesulfonamide The title compound was prepared from Reference Example 44 and (R)-N-[5-(2-amino-1-hydroxy-ethyl)-2-hydroxy-phenyl)-methanesulfonamide according to the procedure of Example 1 as an off-white solid; $^1$H NMR (DMSO) δ 0.92 (d, J=6.57 Hz, 6H), 1.28–1.32 (m, 2H), 1.76–1.90 (m, 2H), 2.58–2.68 (m, 5H), 2.83–2.88 (m, 3H), 2.92 (s, 3H), 3.13–3.17 (m, 2H), 3.76–3.80 (m, 2H), 4.47–4.51 (m, 1H), 5.2 (bs, 1H), 6.82 (d, J=8.22 Hz, 1H), 6.99–7.03 (m. 3H), 7.18 (d, J=1.98 Hz, 1H), 7.54 (d, J=8.97 Hz, 2H); MS (ES) m/z 527.2 (MH$^+$); HRMS for $C_{23}H_{34}N_4O_6S_2$: 527.1987.

EXAMPLE 30

1-(4-{4-[(2R)-2-Hydroxy-2-(4-hydroxy-3-methanesulfonylamino-phenyl)-ethylamino]-piperidin-1-yl}-benzenesulfonyl)-pyrrolidine-(2R)-2-carboxylic Acid Ethyl Ester The title compound was prepared from Reference Example 53 and (R)-N-[5-(2-amino-1-hydroxy-ethyl)-2-hydroxy-phenyl}-methanesulfonamide according to the procedure of Example 1 as a light brown solid; $^1$H NMR (DMSO) δ 1.18 (t, J=7.11 Hz, 3H), 1.27–1.32 (m, 2H), 1.55–160 (m, 2H), 1.74–1.92 (m, 6H), 2.63–2.75 (m, 2H), 2.87–2.96 (m, 3H), 2.92 (s, 3H), 3.07–3.17 (m, 2H), 3.80–3.84 (m, 2H), 4.03–4.13 (m, 4H), 4.48 (m, 1H), 5.2 (bs, 1H), 6.82 (d, J=8.22 Hz, 1H), 6.99–7.05 (m, 3H), 7.18 (d, J=1.98 Hz, 1H), 7.56 (d, J=9.03 Hz, 2H); MS (ES) m/z 611.1 (MH$^+$); HRMS for $C_{28}H_{40}N_4O_8S_2$: 611.2195.

EXAMPLE 31

[Cyclopropylmethyl-(4-{4-[(2R)-2-hydroxy-2-(4-hydroxy-3-methanesulfonylamino-phenyl)-ethylamino]-piperidin-1-yl}-benzenesulfonyl)-amino]-acetic Acid To a stirred solution of 0.15 9 (0.24 mmol) of [cyclopropylmethyl-(4-{4-[(2R)-2-hydroxy-2-(4-hydroxy-3-methanesulfonylamino-phenyl)-ethylamino]-piperidin-1-yl}-benzenesulfonyl)-amino]-acetic acid ethyl ester ( ) in 2 mL of ethanol, 0.1 g (2.4 mmol) of lithium hydroxide monohydrate in 2 ml of water was added dropwise over 10 minutes. After 20 minutes, the reaction mixture was quenched with .13 ml (2.4 mmol) of glacial acetic acid. The solvent was removed in vacuo and the pink aqueous residue was pipetted out of the flask. The solid was then washed with water and ethyl acetate and then dried via vacuum line to give 0.134 g of the title compound as a tan solid; $^1$H NMR (DMSO) δ 0.82 (m, 1H), 1.41 (m, 2H), 1.85–1.97 (m, 2H), 2.68–2.82 (m, 8H), 2.92 (s, 3H), 3.04 (d, J=6.84 Hz, 2H), 3.30 (m, 5H), 3.76 (m, 4H), 4.58 (m, 1H), 6.83 (d, J=8.25 Hz, 1H), 6.94–7.05 (m, 3H), 7.18 (d, J=1.86 Hz, 1H), 7.60 (d, J=8.88 Hz, 2H); MS (ES) m/z 597.1 (MH$^+$); HRMS (MH$^-$) for $C_{26}H_{36}N_4O_8S2$: 595.1904.

EXAMPLE 32

[(4-{4-[(2R)-2-Hydroxy-2-(4-hydroxy-3-methanesulfonylamino-phenyl)-ethylamino]-piperidin-1-yl}-benzenesulfonyl)-isobutyl-amino]-acetic Acid Ethyl Ester The title compound was prepared from Reference Example 46 and (R)-N-[5-(2-amino-1-hydroxy-ethyl)-2-hydroxy-phenyl}-methanesulfonamide according to the procedure of Example 1 as a light brown solid; $^1$H NMR (DMSO) δ 0.82 (d, J=6.54 Hz, 6H), 1.13 (t, J=7.11 Hz, 4H), 1.23–1.33 (m, 2H), 1.68–1.90 (m, 4H), 2.58–2.75 (m, 2H), 2.84–2.87 (m, 3H), 3.79–3.83 (m, 4H), 3.89 (s, 2H), 4.00 (q, J=7.05 Hz, 2H), 4.46–4.51 (m, 2H), 5.2 (bs, 1H), 6.82 (d, J=8.22 Hz, 1H), 6.98–7.03 (m, 3H), 7.18 (d, J=2.01 Hz, 1H), 7.52 (d, J=9.0 Hz, 2H); MS (ES) m/z 627.2 (MH$^+$); HRMS for $C_{28}H_{42}N_4O_8S_2$: 627.2509.

EXAMPLE 33

[(4-{4-[(2R)-2-Hydroxy-2-(4-hydroxy-3-methanesulfonylamino-phenyl)-ethylamino]-piperidin-1-yl}-benzenesulfonyl)-methyl-amino]-acetic Acid The title compound was prepared from [(4-{4-[(2R)-2-Hydroxy-2-(4-hydroxy-3-methanesulfonylamino-phenyl)-ethylamino]-piperidin-1-yl}-benzenesulfonyl)-methyl-amino]-acetic acid ethyl ester according to the procedure of Example 31 as a brown solid; $^1$H NMR (DMSO) δ 1.06 (t, J=7.11 Hz, 4H), 1.43–1.47 (m, 2H), 1.90–1.95 (m, 3H), 2.64 (s, 3H), 2.72–2.87 (m, 4H), 2.92 (s, 3H), 3.41–3.47 (m, 4H), 3.84–3.88 (m, 4H), 4.64–4.66 (m, 1H), 6.85 (d, J=8.25 Hz, 1H), 6.99–7.06 (m, 3H), 7.21 (d, J=1.89 Hz, 1H), 7.52 (d, J=8.88 Hz, 2H); MS (ES) m/z 557.2 (MH$^+$); HRMS (MH$^-$) for $C_{23}H_{32}N_4O_8S_2$: 555.1580.

EXAMPLE 34

[(4-{4-[(2R)-2-Hydroxy-2-(4-hydroxy-3-methanesulfonylamino-phenyl)-ethylamino]-piperidin-1-yl}-benzenesulfonyl)-isobutyl-amino]-acetic Acid The title compound was prepared from [(4-{4-[(2R)-2-Hydroxy-2-(4-hydroxy-3-methanesulfonylamino-phenyl)-ethylamino]-piperidin-1-yl}-benzenesulfonyl)-isobutyl-amino]-acetic acid ethyl ester according to the procedure of Example 31 as an off white solid; $^1$H NMR (DMSO) δ 0.81 (d, J=6.6 Hz, 6H), 1.37–1.41 (m, 2H), 1.75–1.91 (m, 4H), 2.69–2.85 (m, 8H), 2.92 (s, 3H), 3.45 (m, 3H), 3.73 (m, 4H), 4.60–4.62 (m, 1H), 6.83 (d, J=8.25 Hz, 1H), 6.95–7.05 (m, 3H), 7.19 (d, J=2.01 Hz, 1H), 7.57 (d, J=8.94 Hz, 2H); MS (ES) m/z 597.2 (MH$^-$); HRMS for $C_{26}H_{38}N_4O_8S_2$: 597.2052.

EXAMPLE 35

1-(4-{4-[(2R)-2-Hydroxy-2-(4-hydroxy-3-methanesulfonylamino-phenyl)-ethylamino]-piperidin-1-yl}-benzenesulfonyl)-pyrrolidine-(2R)-2-carboxylic Acid The title compound was prepared from 1-(4-{4-[(2R)-2-Hydroxy-2-(4-hydroxy-3-methanesulfonylamino-phenyl)-ethylamino]-piperidin-1-yl}-benzenesulfonyl)-pyrrolidine-(2R)-2-carboxylic acid ethyl ester according to the procedure of Example 31 as a tan solid; $^1$H NMR (DMSO) δ 1.32–1.36 (m, 2H), 1.51 (m, 2H), 1.77 (m, 2H), 1.90 (s, 1H), 2.66–2.78 (m, 6H), 2.92 (s, 3H), 3.12–3.15 (m, 4H), 3.27 (m, 2H), 3.79 (m, 2H), 3.93–3.98 (m, 2H), 4.52–4.56 (m, 1H), 6.83 (d, J=8.25 Hz, 1H), 6.98–7.04 (m, 3H), 7.19 (d, J=1.92 Hz, 1H), 7.57 (d, J=8.97 Hz, 2H); MS (ES) m/z 581.1 (MH$^-$); HRMS for $C_{25}H_{34}N_4O_8S_2$: 581.1747.

EXAMPLE 36

Ethyl (2S)-1-[(4-{4-[((2R)-2-Hydroxy-2-{4-hydroxy-3-[(methylsulfonyl)amino]phenyl}ethyl)amino]-1-piperidinyl}phenyl)sulfonyl]-2-pyrrolidinecarboxylate The title compound was prepared from Reference Example 56 and (R)-N-(5-(2-amino-1-hydroxy-ethyl)-2-hydroxy-phenyl}-methanesulfonamide according to the procedure of Example 1 as a tan foam; $^1$H NMR (DMSO) δ 1.16 (t, J=7.08 Hz, 3H), 1.24–1.32 (m, 2H), 1.55–1.60 (M, 2H), 1.77–1.94 (m, 5H), 2.63–2.75 (m, 3H), 2.87–2.96 (m, 2H), 2.92 (s, 3H), 3.09–3.13 (m, 1H), 3.28–3.39 (m, 3H), 3.80–3.85 (m, 2H), 4.03–4.14 (m, 4H), 4.47–4.52 (m, 1H), 6.83 (d, J=8.25 Hz, 1H), 6.99–7.05 (m, 3H), 7.18 (d, J=2.01 Hz, 1H), 7.56 (d, J=9.0 Hz, 2H); MS (ES) m/z 611.1 (MH$^+$); HRMS for $C_{27}H_{38}N_4O_8S_2$: 611.2194.

EXAMPLE 37

Ethyl (2S)-2-{[(4-{4-[((2R)-2-Hydroxy-2-{4-hydroxy-3-[(methylsulfonyl)amino]-phenyl}ethyl)amino]-1-piperidinyl}phenyl)sulfonyl]amino}-4-methylpentanoate The title compound was prepared from Reference Example 61 and (R)-N-[5-(2-amino-1-hydroxy-ethyl)-2-hydroxy-phenyl}-methanesulfonamide according to the procedure of Example 1 as a tan foam; $^1$H NMR (DMSO) δ 0.70 (d, J=6.51 Hz, 3H), 0.80 (d, J=6.6 Hz, 3H), 1.02 (t, J=7.08 Hz, 3H), 1.23–1.40 (m, 5H), 1.51–1.70 (m, 2H), 1.85–1.90 (m, 3H), 2.59–2.76 (m, 3H), 2.84–2.89 (m, 2H), 2.92 (s, 3H), 3.63 (m, 2H), 3.77–3.85 (m, 4H), 4.47–4.52 (m, 1H), 5.25 (bs, 1H), 6.82 (d, J=8.22 Hz, 1H), 6.99–7.03 (m, 3H), 7.18 (d, J=2.01 Hz, 1H), 7.48 (d, J=9.0 Hz, 2H); MS (ES) m/z 627.2 (MH$^+$); HRMS for $C_{28}H_{42}N_4O_8S_2$: 627.2509.

EXAMPLE 38

Ethyl (2S)-2-{[(4-{4-[((2R)-2-hydroxy-2-{4-hydroxy-3-[(methylsulfonyl)amino]-phenyl}ethyl)amino]-1-piperidinyl}phenyl)sulfonyl]amino}-3-methylbutanoate The title compound was prepared from Reference Example 62 and (R)-N-[5-(2-amino-1-hydroxy-ethyl)-2-hydroxy-phenyl}-methanesulfonamide according to the procedure of Example 1 as a brown foam; $^1$H NMR (DMSO) δ 0.80 (t, J=6.96 Hz, 3H), 1.00 (t, J=7.14 Hz, 3H), 1.23–1.34 (m, 2H), 1.76–1.90 (m, 4H), 2.60–2.72 (m, 4H), 2.83–2.88 (m, 2H), 2.92 (s, 3H), 3.39–3.41 (m, 2H), 3.74–3.83 (m, 5H), 4.48–4.52 (m, 1H), 5.3 (bs, 1H), 6.82 (d, J=8.25 Hz, 1h), 6.95–7.03 (m, 3H), 7.18 (d, J=2.01 Hz, 1H), 7.49 (d, J=9.0 Hz, 2H); MS (ES) m/z 613.2 (MH$^+$); HRMS for $C_{27}H_{40}N_4O_8S_2$: 613.2350.

EXAMPLE 39

(2S)-1-[(4-{4-[((2R)-2-Hydroxy-2-{4-hydroxy-3-[(methylsulfonyl)amino]-phenyl}ethyl)amino]-1-piperidinyl}phenyl)sulfonyl]-2-pyrrolidinecarboxylic Acid The title compound was prepared from ethyl (2S)-1-[(4-(4-[((2R)-2-hydroxy-2-{4-hydroxy-3-[(methylsulfonyl)amino]phenyl}ethyl)amino]-1-piperidinyl}phenyl)sulfonyl]-2-pyrrolidinecarboxylate according to the procedure of Example 31 as a brown solid; $^1$H NMR (DMSO) δ 1.37 (m, 2H), 1.46–1.50 (m, 1H), 1.68–1.79 (m, 3H), 1.85–1.96 (m, 2H), 1.90 (s, 1H), 2.65–2.72 (m, 3H), 2.77–2.89 (m, 3H), 2.92 (s, 3H), 3.06–3.12 (m, 2H), 3.21–3.23 (m, 3H), 3.80–3.85 (m, 2H), 3.92–3.96 (m, 1H), 4.56–4.58 (m, 1H), 6.84 (d, J=8.28 Hz, 1H), 6.99–7.05 (m, 3H), 7.20 (d, J=1.95 Hz, 1H), 7.57 (d, J=8.97 Hz, 2H); MS (ES) m/z 583.1 (MH$^+$); HRMS for $C_{25}H_{34}N_4O_8S_2$: 583.1883.

EXAMPLE 40

1-(4-{4-[2-Hydroxy-2-(4-hydroxy-3-methanesulfonylmethyl-phenyl)-ethylamino]-piperidin-1-yl}-benzenesulfonylamino)-cyclopentane Carboxylic Acid Ethyl Ester The title compound was prepared from Reference Example 66 and (R)-N-[5-(2-amino-1-hydroxy-ethyl)-2-hydroxy-phenyl}-methanesulfonamide according to the procedure of Example 1 as a beige solid; $^1$H NMR (DMSO) δ 1.11 (t, J=7.11 Hz, 3H), 1.27–1.30 (m, 4H), 1.49 (m, 4H), 1.88 (m, 8H), 2.63–2.73 (m, 3H), 2.83–2.88 (m, 2H), 2.92 (s, 3H), 3.77–3.82 (m, 2H), 3.89 (q, J=708 Hz, 2H), 4.48 (m, 1H), 5.2 (bs, 1H), 6.82 (d, J=8.25 Hz, 1H), 6.95–7.03 (m, 3H), 7.18 (d, J=2.01 Hz, 1H), 7.50 (d, J=9.0 Hz, 2H); MS (ES) m/z 625.2 (MH$^+$); HRMS for $C_{28}H40_{N4}O_8S2$: 625.2361.

EXAMPLE 41

N-{2-Hydroxy-5-[(1R)-1-hydroxy-2-({1-[4-(1-pyrrolidinylsulfonyl)phenyl]-piperidinyl}-4-amino)ethyl]phenyl}methanesulfonamide The title compound was prepared from Reference Example 34 and (R)-N-[5-(2-amino-1-hydroxy-ethyl)-2- hydroxy-phenyl}-methanesulfonamide according to the procedure of Example 1 as a beige solid; $^1$H NMR (DMSO) δ 1.23–1.35 (m, 2H), 1.60–1.65 (m, 4H), 1.83–1.91 (m, 2H), 2.59–2.76 (m, 5H), 2.86–2.95 (m, 2H), 2.92 (s, 3H), 3.03–3.08 (m, 4H), 3.16 (s, 1H), 3.79–3.84 (m, 2H), 4.47–4.52 (m, 1H), 5.3 (bs, 1H), 6.82 (d, J=8.25 Hz, 1H), 6.99–7.05 (m, 3H), 7.18 (d, J=2.01 Hz, 1H), 7.54 (d, J=8.97 Hz, 2H); MS (ES) m/z 539.2 (MH$^+$); HRMS for $C_{24}H_{34}N_4O_6S_2$: 539.1990.

EXAMPLE 42

N-{2-Hydroxy-5-[(1R)-1-hydroxy-2-({1-[4-(1-piperidinylsulfonyl)phenyl]-piperidinyl}-4-amino)ethyl]phenyl}methanesulfonamide The title compound was prepared from Reference Example 35 and (R)-N-[5-(2-amino-1-hydroxy-ethyl)-2-hydroxy-phenyl}-methanesulfonamide according to the procedure of Example 1 as an off white solid; $^1$H NMR (DMSO) δ 1.24–1.35 (m, 4H), 1.50–1.53 (m, 4H), 1.83–1.90 (m, 2H), 2.59–2.71 (m, 4H), 2.75–2.82 (m, 4H), 2.87–2.95 (m, 2H), 2.92 (s, 3H), 3.17 (s, 2H), 3.79–3.84 (m, 2H), 4.47–4.51 (m, 1H), 5.3 (bs, 1H), 6.82 (d, J=8.25 Hz, 1H), 6.99–7.05 (m, 3H), 7.18 (d, J=2.01 Hz, 1H), 7.46 (d, J=9.0 Hz, 2H); MS (ES) m/z 553.2 (MH$^+$); HRMS for $C_{25}H_{36}N_4O_6S_2$: 553.2149.

EXAMPLE 43

1-(4-{4-[2-Hydroxy-2-(4-hydroxy-3-methanesulfonylmethyl-phenyl)ethylamino]-piperidin-1-yl}-benzenesulfonylamino)cyclohexane Carboxylic Acid Ethyl Ester The title compound was prepared from Reference Example 68 and (R)-N-[5-(2-amino-1-hydroxy-ethyl)-2-hydroxy-phenyl}-methanesulfonamide according to the procedure of Example 1 as a beige solid; $^1$H NMR (DMSO) δ 1.10 (t, J=7.14 Hz, 3H), 1.23–1.33 (m, 8H), 1.63–1.90 (m, 6H), 2.59–2.76 (m, 4H), 2.83–2.88 (m, 2H), 3.17 (s, 3H), 3.77–3.86 )m, 2H), 4.47–4.52 (m, 1H), 5.3 (bs, 1H), 6.82 (d, J=8.22 Hz, 1H), 6.96–7.03 (m, 3H), 7.18 (d, J=1.98 Hz, 1H), 7.51 (d, J=8.97 Hz, 2H); MS (ES) m/z 639.2 (MH$^+$); HRMS for $C_{29}H_{42}N_4O_8S_2$: 639.2517.

EXAMPLE 44

1-(4-{4-[2-Hydroxy-2-(4-hydroxy-3-methanesulfonylmethyl-phenyl)-ethylamino]-piperidin-1-yl}-benzenesulfonyl)-isopropyl-amino]acetic Acid Ethyl Ester The title compound was prepared from Reference Example 69 and (R)-N-[5-(2-amino-1-hydroxy-ethyl)-2-hydroxy-phenyl}-methanesulfonamide according to the procedure of Example 1 as a beige solid; $^1$H NMR (DMSO) δ 0.91 (d, J=6.69 Hz, 6H), 1.19 (t, J=7.08 Hz, 3H), 1.28–1.35 (m, 2H), 1.83–1.90 (m, 2H), 2.59–2.76 (m, 5H), 2.86 (m, 2H), 2.92 (s, 3H), 3.74–3.84 (m, 4H), 3.91 (s, 2H), 4.10 (q, J=7.05 Hz, 2H), 4.47–4.52 (m, 1H), 5.3 )bs, 1H), 6.82 (d, J=8.25 Hz, 1H), 6.99–7.03 (m, 3H), 7.18 (d, J=2.01 Hz, 1H), 7.62 (d, J=9.03 Hz, 2H); MS (ES) m/z 613.2 (MH$^+$); HRMS for $C_{29}H_{42}N_4O_8S_2$: 613.2362.

EXAMPLE 45

N-[2-Hydroxy-5-(1-hydroxy-2-{1-[4-(toluene-4-sulfonyl)-phenyl]-piperidin-4-ylamino}-ethyl)-phenyl]-methanesulfonamide The title compound was prepared according to the procedure of Example 1 from 0.13 g (0.4 mmol) of Reference Example 25, 1-[4-(Toluene-4-sulfonyl)-phenyl]-piperidin-4-one, and 0.12 g (0.5 mmol) of (R)-N-[5-(2-amino-1-hydroxy-ethyl)-2-hydroxy-phenyl}-methanesulfonamide, yielding 0.18 g of a white solid; m.p. 115–118° C.; MS (ES) m/z 560.0 (MH$^+$); HRMS (FAB) Calcd. for $C_{27}H_{34}N_3O_6S_2$ (MH$^+$): 560.1889, Found: 560.1886.

EXAMPLE 46

4-((2S)-2-Hydroxy-3-{1-[4-(toluene-4-sulfonyl)-phenyl]-piperidin-4-ylamino}-propoxy)-1,3-dihydro-benzoimidazol-2-one The title compound was prepared according to the procedure of Example 1 from 0.13 g (0.4 mmol) of Reference Example 25, 1-[4-(toluene-4-sulfonyl)-phenyl]-piperidin-4-one, and 0.13 g (0.6 mmol) of 4-((2S)-3-Amino-2-hydroxy-propoxy)-1,3-dihydro-benzoimidazol-2-one, yielding 0.18 g of a white solid; m.p. 130–132° C.; MS (ES) m/z 537.0 (MH$^+$); HRMS (FAB) Calcd. for $C_{28}H_{33}N_4O_5S$ (MH$^+$): 537.2166, Found: 537.2169.

EXAMPLE 47

2-(2-Butynyl)-2-[(4-{4-[((2R)-2-hydroxy-2-{4-hydroxy-3-[(methylsulfonyl)amino]-phenyl}ethyl)amino]-1-piperidinyl}phenyl)sulfonyl]-4-hexynoicacid tert-Butyl Ester The title compound was prepared according to the procedure of Example 1 from 0.37 g (0.8 mmol) of Reference Example 27, 2-But-2-ynyl-2-[4-(4-oxo-piperidin-1-yl)-benzenesulfonyl]-hex-4-ynoic acid tert-butyl ester, and 0.24 g (1.0 mmol) of (R)-N-[5-(2-amino-1-hydroxy-ethyl)-2-hydroxy-phenyl}-methanesulfonamide, yielding 0.54 g of an off-white solid; m.p. 93–95° C.; MS (ES) m/z 688.2 (MH$^+$); HRMS (ES) Calcd. for $C_{34}H_{46}N_3O_8S_2$ (MH$^+$): 688.2721, Found: 688.2722.

EXAMPLE 48

2-(2-Butynyl)-2-[(4-{4-[((2R)-2-hydroxy-2-{4-hydroxy-3-[(methylsulfonyl)amino]phenyl}ethyl)amino]-1-piperidinyl}phenyl)sulfonyl]-4-hexynoicacid To a solution of 2-(2-butynyl)-2-[(4-{4-[((2R)-2-hydroxy-2-[4-hydroxy-3-[(methylsulfonyl)amino)-phenyl)ethyl)amino]-1-piperidinyl}phenyl)sulfonyl]-4-hexynoicacid tert-butyl ester 0.21 g (0.3 mmol) in dichloromethane (3 ml) was added trifluoroacetic acid (0.23 ml, 3 mmol), and the mixture was stirred at room temperature for 2 days. It was then evaporated and treated with 10% sodium bicarbonate solution until pH 6. The resulting suspension was filtered and the precipitate washed with water, and dried in vacuo to give 85 mg of a beige solid; m.p. 175–177° C.; MS (ES) m/z 630.6 (M–H$^-$); HRMS (EI) Calcd. for $C_{30}H_{36}N_3O_8S_2$ (M–H$^-$): 630.1949, Found: 630.1943.

EXAMPLE 49

1-(4-{4-[(2S)-2-Hydroxy-3-(2-oxo-2,3-dihydro-1H-benzoimidazol-4-yloxy)-propylamino]-piperidin-1-yl}-benzenesulfonyl)-imidazolidine-2,4-dione Step a) N-[(4-Fluorophenyl)sulfonyl]-glycine A saturated sodium carbonate solution was added dropwise into a mixture of 4-fluorobenzenesulfonyl chloride (30.0 g, 154 mmol), glycine (11.5 g, 154 mmol), and dioxane (200 mL), until a basic (pH about 9) solution was achieved. After 30 minutes the mixture was neutralized with HCl (2 N), and the volatiles were removed in vacuo. The residue was recrystallized from cold (0° C.) to yield a white solid (23.6 g, 66% yield): mp 144–146° C.; $^1$H NMR (400 MHz, DMSO-d$_6$): δ 3.58 (s, 2H), 7.39–7.42 (m, 2H), 7.81–7.86 (m, 2H), 8.06 (brs, 1H), 12.5 (brs, 1H); MS m/e232 (M−H)$^+$; Analysis for: C$_8$H$_8$FNO$_4$S Calc'd: C, 41.20; H, 3.46; N, 6.01 Found: C, 41.14; H, 3.51; N, 5.85.

Step b) 1-[(4-Fluorophenyl)sulfonyl]-2-thioxo-4-imidazolidinone

A mixture of N-[(4-fluorophenyl)sulfonyl]-glycine (17.0 g, 72.9 mmol), ammonium thiocyanate (7.2 g, 94.8 mmol), acetic anhydride (17.2 mL, 182.2 mmol), and pyridine (70 mL) was stirred at 100° C. for 24 hours. Then, the mixture was into water and extracted with ethyl acetate. The organic extracts were dried over MgSO4. Evaporation and purification by flash chromatography (hexanes/ethyl acetate 2/1) gave a yellow solid (19.6 g, 98% yield): mp 208–210° C.; $^1$H NMR (400 MHz, DMSO-d$_6$): δ 4.78 (s, 2H), 7.47–7.51 (m, 2H), 8.14–8.18 (m, 2H), 12.6 (S, 1H); MS m/e 274 M$^+$; Analysis for: C$_9$H$_7$FN$_2$O$_3$S$_2$ Calc'd: C, 39.41; H, 2.57; N, 10.21 Found: C, 39.90; H, 2.71; N, 10.09.

Step c) 1-[(4-Fluorophenyl)sulfonyl]-2,4-imidazolidinedione

A mixture of 1-[(4-fluorophenyl)sulfonyl]-2-thioxo-4-imidazolidinone (14.5 g, 52.9 mmol), and chloroacetic acid (100 g) was stirred at 120° C. for 2 days. Then, the mixture was poured into water and extracted with ethyl acetate. The organic extracts were dried over MgSO$_4$. Evaporation and purification by flash chromatography (hexanes/ethyl acetate 1/1) gave a white solid (12.6 g, 92% yield): mp 232–234° C.; $^1$H NMR (400 MHz, DMSO-d$_6$): δ 4.48 (s, 2H), 7.47–7.52 (m, 2H), 8.06–8.09 (m, 2H), 11.61 (s, 1H); MS m/e 257 (M−H)$^+$; Analysis for: C$_9$H$_7$FN$_2$O$_4$S Calc'd: C, 41.86; H, 2.73; N, 10.85 Found: C, 42.24; H, 2.72; N, 10.6.

Step d) 1-[[4-(1,4-Dioxa-8-azaspiro[4.5]dec-8-yl)phenyl]sulfonyl]-2,4-imidazolidinedione A mixture of 1-[(4-fluorophenyl)sulfonyl]-2,4-imidazolidinedione (3.6 g, 13.9 mmol), 1,4-dioxa-8-azaspiro[4.5-decane (3.56 mL, 27.8 mmol), 1,3-dimethyl-3,4,5,6-tetrahydro-2(1H-pyrimidinone (30 mL), acetonitrile (15 mL), and potassium carbonate (3.84 g, 27.8 mmol) was stirred at 65° C. for 2 days. Then, the mixture was poured into water and extracted with ethyl acetate. The organic extracts were dried over MgSO$_4$.

Evaporation and purification by flash chromatography (hexanes/ethyl acetate 1/1) gave a white solid (4.15 g, 78% yield): mp 222–224° C.; $^1$H NMR (400 MHz, DMSO-d$_6$): δ 1.63–1.66 (m, 4H), 3.47–3.9 (m, 4H), 3.9 (s, 4H), 4.41 (s, 2H), 7.03–7.07 (m, 2H), 7.71–7.74 (m, 2H), 11.46 (brs, 1H); MS m/e 382 (M+H)$^+$; Analysis for: C$_{16}$H$_{19}$N$_3$O$_6$S Calc'd: C, 50.39; H, 5.02; N, 11.02 Found: C, 50.22; H, 4.92; N, 10.89.

Step e) 1-[[4-(4-Oxo-1-piperidinyl)phenyl]sulfonyl]-2,4-imidazolidinedione

A mixture of 1-[[4-(1,4-dioxa-8-azaspiro[4.5]dec-8-yl)phenyl]sulfonyl]-2,4-imidazolidinedione (4.1 g, 10.76 mmol), HCl (concentrated, 10 mL), and dioxane (15 mL) was stirred at room temperature for 5 days. Then, the mixture was poured into water and extracted with ethyl acetate. The organic extracts were dried over MgSO$_4$.

Evaporation and purification by flash chromatography (hexanes/ethyl acetate 1/1) gave a white solid (3.2 g, 88% yield): mp 210–212° C.; $^1$H NMR (400 MHz, DMSO-d$_6$): δ 2.48 (m, 2H), 3.78 (m, 4H), 4.44 (s, 2H), 7.06–7.08 (m, 2H), 7.76–7.79 (m, 2H), 11.48 (s, 1H); MS m/e 338 (M+H)$^+$; Analysis for: C$_{14}$H$_{15}$N$_3$O$_5$S Calc'd: C, 49.85; H, 4.48; N, 12.46 Found: C, 49.51; H, 4.51; N, 11.84.

Step f) 1-(4-{4-[(2S)-2-Hydroxy-3-(2-oxo-2,3-dihydro-1H-benzoimidazol-4-yloxy)-propylamino]-piperidin-1-yl}-benzenesulfonyl)-imidazolidine-2,4-dione Acetic acid (0.14 mL, 2.38 mmol) was added dropwise into a mixture of 4-{[[(2S)-3-amino-2-hydroxypropyl]oxy}-1,3-dihydro-2H-benzimidazol-2-one (265 mg, 1.19 mmol), 1-[[4-(4-oxo-1-piperidinyl)phenyl]sulfonyl]-2,4-imidazolidinedione (400 mg, 1.19 mmol) and N,N-dimethylformamide (5 mL). The mixture was stirred for 20 minutes and then, sodium triacetoxyborohydride (303 mg, 1.43 mmol) was added, and the new mixture was stirred at room temperature for 24 hours. The volatiles were removed in vacuo and the residue was purified by flash chromatography (dichloromethane/methyl alcohol 3/1) to produce a brown solid (256 mg, 40% yield): mp 230° C. (decomposed); $^1$H NMR (400 MHz, DMSO-d$_6$): δ 1.52–1.63 (m, 2H), 2.04–2.15 (m, 2H), 2.48 (m, 2H), 2.9–3.0 (m, 2H), 3.13–3.15 (m, 1H), 3.2–3.4 (m, 3H), 4.0–4.1 (m, 5H), 4.42 (s, 2H), 6.6–6.63 (m, 2H), 6.8–6.85 (m, 1H), 7.03–7.05 (m, 2H), 7.78–7.8 (m, 2H), 10.6 (s, 1H), 10.7 (s, 1H); MS m/e 543 (M−H)$^+$; Analysis for: C$_{24}$H$_{28}$N$_6$O$_7$S Calc'd: C, 45.24; H, 5.38; N, 12.88 Found: C, 45.88; H, 5.36; N, 13.88.

EXAMPLE 50

N-[5-((1R)-2-{1-[4-(2,4-Dioxo-imidazolidine-1-sulfonyl)-phenyl]piperidin-4-ylamino}-1-hydroxy-ethyl)-2-hydroxy-phenyl]-methanesulfonamide Acetic acid (0.15 mL, 2.6 mmol) was added dropwise into a mixture N-{5-[(1R)-2-amino-1-hydroxyethyl]-2-hydroxyphenyl}methanesulfonamide (320 mg, 1.3 mmol), 1-[[4-(4-oxo-1-piperidinyl)phenyl]sulfonyl}-2,4-imidazolidinedione (440 mg, 1.3 mmol) and N,N-dimethylformamide (5 mL). The mixture was stirred for 20 minutes and then, sodium triacetoxyborohydride (331 mg, 1.56 mmol) was added, and the new mixture was stirred at room temperature for 24 hours. The volatiles were removed in vacuo and the residue was purified by flash chromatography (dichloromethane/methyl alcohol 4/1) to produce a white solid (496 mg, 67% yield): mp 200–202° C.; $^c$ 1.35–1.42 (m, 2H), 1.81–1.97 (m, 2H), 2.83–2.97 (m, 6H), 3.95–3.97 (m, 2H), 4.22 (s, 2H), 4.57–4.6 (m, 1H), 7.1 (M, 3H), 7.2 (m, 1H), 7.75 (m, 2H), 8.4 (brs, 2H); MS m/e 566 (M−H)$^+$; Analysis for: C$_{23}$H$_{29}$N$_5$O$_8$S$_2$ Calc'd: C, 48.67; H, 5.11; N, 12.34 Found: C, 47.64; H, 5.2; N, 11.26.

EXAMPLE 51

1-(4-{4-[((2S)-2-Hydroxy-2-(2-trifluoromethyl-thiazol-4-yl)-ethylamino]-piperidin-1-yl}-benzenesulfonyl)-imidazolidine-2,4-dione Acetic acid (0.09 mL, 1.6 mmol) was added dropwise into a (1S)-2-amino-1-[2-(trifluoromethyl)-1,3-thiazol-4-yl]-1-ethanol (152 mg, 0.71 mmol), 1-[[4-(4-oxo-1-piperidinyl)phenyl]sulfonyl]-2,4-imidazolidinedione (220 mg, 0.65 mmol) and N,N-dimethylformamide (3 mL). The mixture was stirred for 20 minutes and then, sodium triacetoxyborohydride (276 mg, 1.3 mmol) was added, and the new mixture was stirred at room temperature for 24 hours. The volatiles were removed in vacuo and the residue was purified by flash chromatography (dichloromethane/methyl alcohol 4/1) to produce an off-white solid (265 mg, 68% yield): mp 185–187° C.; $^1$H NMR (400 MHz, DMSO-d$_6$): δ 1.22–1.35 (m, 2H), 1.8–1.9 (m, 1H), 2.7–2.83 (m, 2H), 2.9–3.01 (m, 3H), 3.8 (m, 2H), 4.2 (s, 2H), 4.81 (m, 1H), 7.1 (m, 2H), 7.8 (m, 2H), 7.95 (s, 1H); MS m/e 534 (M+H)$^+$; Analysis for: $C_{20}H_{22}F_3N_5O_5S_2$ Calc'd: C, 45.02; H, 4.16; N, 13.13 Found: C, 42.79; H, 4.27; N, 11.95.

EXAMPLE 52 tert-Butyl 2-{[(4-{4-[((2R)-2-hydroxy-2-{4-hydroxy-3-[(methylsulfonyl)amino]-phenyl}ethyl) amino]-1-piperidinyl}phenyl)sulfonyl]amino}acetate Step a) tert-Butyl 2-{[(4-fluorophenyl)sulfonyl] amino}acetate N,N-Diisopropylethylamine (41.4 mL, 238.8 mmol) was added into a mixture of 4-fluorobenzenesulfonyl chloride (23.2 g, 119.4 mmol), glycine tert-butyl ester hydrochloride (20 g, 119.4 mmol) and tetrahydrofuran (200 mL). The mixture was stirred for 24 hours. The volatiles were then removed in vacuo, and the residue was taken in water (2000 mL) and stirred for 30 minutes. The precipitated solid was filtered and dried to give a white solid (32.1 g, 93% yield): mp 105–107° C.; $^1$H NMR (400 MHz, DMSO-d$_6$): δ 1.28 (s, 9 H), 3.6 (7.4 (m, 2H), 7.83 )m, 2H), 8.17 (t, J=6.37 Hz, 1H); d, J=6.37 Hz, 2H), MS m/e 289 M$^+$; Analysis for: $C_{12}H_{16}FNO_4S$ Calc'd: C, 49.82; H, 5.57; N, 4.84 Found: C, 50.06; H, 5.72; N, 4.79.

Step b) tert-Butyl 2-({[4-(4-hydroxy-1-piperidinyl)phenyl] sulfonyl}amino)acetate A mixture of tert-butyl 2-{[(4-fluorophenyl)sulfonyl] amino}acetate (22.5 g, 77.8 mmol), 4-hydroxypiperidine (11.8 g, 116.8 mmol), potassium carbonate (16.1 g, 116.8 mmol), 1,3-dimethyl-3,4,5,6-tetrahydro-2(1H)-pyrimidinone (90 mL), and acetonitrile (60 mL) was stirred at 75° C. for 2 days. The mixture was poured into water and extracted with ethyl acetate. The organic extracts were dried over MgSO$_4$. Evaporation and purification by flash chromatography (hexanes/ethyl acetate 1/1) gave a white solid (22.1 g, 77% yield): mp 125–127° C.; $^1$H NMR (400 MHz, DMSO-d$_6$): δ 1.29 (s, 9 H), 1.4 (m, 2H), 2.79 (m, 2H), 3.0 (m, 2H), 3.46 (m, 2H), 3.68 (m, 3H), 4.72 (m, 1H), 7.0 (m, 2H), 7.56 (m, 2H), 7.68 (m, 1H); MS m/e 371 (M+H)$^+$; Analysis for: $C_{17}H_{26}N_2O_5S$ Calc'd: C, 55.12; H, 7.07; N, 7.56 Found: C, 55.45; H, 7.24; N, 7.52.

Step c) tert-Butyl 2-({[4-(4-oxo-1-piperidinyl)phenyl] sulfonyl}amino)acetate

Trifluoroacetic acid (0.21 mL, 2.7 mmol) was added dropwise into a cold (0° C.) mixture of tert-butyl 2-({[4-(4-hydroxy-1-piperidinyl)phenyl]sulfonyl}amino)acetate (2.0 g, 5.4 mmol), dimethyl sulfoxide (15 mL), benzene (15 mL), pyridine (0.43 mL, 5.44 mmol), and 1,3-dicyclohexylcarbodiimide (3.34 g, 16.2 mmol). The mixture was allowed to come to room temperature, stirred for 20 hours, and then diluted with ethyl acetate. The precipitated solid was filtered and discarded. The filtrate was washed with water, and dried over MgSO$_4$. Evaporation and purification by flash chromatography (hexanes/ethyl acetate 1/1) gave a white solid (1.85 g, 93% yield): mp 130–132° C.; $^1$H NMR (400 MHz, DMSO-d$_6$): δ 1.29 (s, 9 H), 2.4 (m, 4H), 3.46 (d, J=6.15 Hz, 2H), 3.73 (m, 4H), 7.07 (m, 2H), 7.58 (m, 2H), 7.69 (t, J=6.15 Hz, 1H); MS m/e 368 M$^+$; Analysis for: $C_{17}H_{26}N_2O_5S$ Calc'd: C, 55.42; H, 6.57; N, 7.60 Found: C, 55.56; H, 6.41; N, 7.57.

Step d) tert-Butyl 2-{[(4-{4-[((2R)-2-hydroxy-2-{4-hydroxy-3-[(methylsulfonyl)amino]phenyl}ethyl)amino]-1-piperidinyl}phenyl)sulfonyl]amino}acetate Acetic acid (2.92 mL, 5.1 mmol) was added dropwise into a N-{5-[(1R)-2-amino-1-hydroxyethyl]-2-hydroxyphenyl}methanesulfonamide (627 mg, 2.55 mmol), tert-butyl 2-({[4-(4-oxo-1-piperidinyl)phenyl] sulfonyl}amino)acetate (940 mg, 2.55 mmol), and N,N-dimethylformamide (7 mL). The mixture was stirred for 20 minutes and then, sodium triacetoxyborohydride (649 mg, 3.06 mmol) was added, and the new mixture was stirred at room temperature for 24 hours. The volatiles were removed in vacuo and the residue was purified by flash chromatography (dichloromethane/methyl alcohol 8/1) to produce a white solid (1.21 g, 80% yield): mp 113–115° C.; $^1$H NMR (400 MHz, DMSO-d$_6$): δ 1.23–1.29 (m, 11H), 1.8–1.83 (m, 2H), 2.6–2.7 (m, 3H), 2.81–28.3 (m, 2H), 2.91 (s, 3H), 3.45 (s, 2H), 3.79 (M, 2H), 4.47 (m, 1H), 6.95 (m, 1H), 7.0 (m, 3H), 7.18 (m, 1H), 7.5 (m, 2H); MS m/e 599 (M+H)$^+$; Analysis for: $C_{26}H_{38}N_4O_8S_2 \times 1\ CH_3CO_2H$ Calc'd: C, 51.05; H, 6.43; N, 8.50 Found: C, 51.08; H, 6.49; N, 8.70.

EXAMPLE 53

2-{[(4-{4-[((2R)-2-hydroxy-2-{4-hydroxy-3-[(methylsulfonyl)amino]phenyl}ethyl)amino]-1-piperidinyl}phenyl)sulfonyl]amino}acetic Acid A mixture of tert-butyl 2-{[(4-{4-[((2R)-2-hydroxy-2-{4-hydroxy-3-[(methylsulfonyl)amino]phenyl}ethyl)amino]-1-piperidinyl}phenyl)sulfonyl]-amino}acetate (600 mg, 1 mmol), dichloromethane (10 mL), and trifluoroacetic acid (2 mL) was stirred at room temperature for 15 hours. The mixture was then poured into ethyl ether (50 mL) and the precipitated solid was filtered and dried. Purified by HLPC reverse phase chromatography (YMC C18 column, 85:15 water : 0.1% trifluoroacetic acid/acetonitrile) to yield a white solid (340 mg, 51%): mp 170–172° C.; MS m/e 541 (M–H)$^+$; $^1$H NMR (400 MHz, DMSO-d$_6$): δ 1.4–1.5 (m, 2H), 1.9–2.0 (m, 2H), 2.75–3.1 (m, 8H), 3.2 (s, 2H), 3.84 (m, 2H), 4.65 (m, 1H), 6.83 (m, 2H), 7.0–7.06 (m, 3H), 7.2 (m, 1H), 7.6 (2H); Analysis for: $C_{22}H_{30}N_4O_8S_2 \times 0.5\ CF_3CO_2H$ Calc'd: C, 46.08; H, 5.09; N, 9.35 Found; C, 46.15; H, 4.99; N, 9.13.

EXAMPLE 54 tert-Butyl 2-{[2-(tert-butoxy)-2-oxoethyl][(4-{4-[((2R)-2-hydroxy-2-{4-hydroxy-3-[(methylsulfonyl) amino]phenyl}ethyl)amino]-1-piperidinyl}-phenyl) sulfonyl]amino}acetate Step a) tert-Butyl 2-([2-(tert-butoxy)-2-oxoethyl-{[4-(4-oxo-1-piperidinyl)phenyl]sulfonyl}amino)acetate Sodium hydride (60% in mineral oil, 109 mg, 2.72 mmol) was added into a solution of tert-butyl 2-([4-(4-oxo-1-piperidinyl)phenyl]sulfonyl}amino)acetate 91 g, 2.72 mmol), and N,N-dimethylformamide (5 mL). The mixture was stirred at room temperature for 2 hours, and then tert-butyl bromoacetate (0.48 mL, 3.26 mmol) was added dropwise. The new mixture was stirred for 1 hour, poured into water and extracted with ethyl acetate. The organic extracts were dried over MgSO$_4$. Evaporation and purification by flash chromatography (hexanes/ethyl acetate 2/1) gave a yellow oil (670 mg, 52% yield): MS m/e 482 (M)+; $^1$H NMR (400 MHz, DMSO-d$_6$): δ 1.31 (s, 18H), 2.4 (m, 4H), 3.75 (m, 4H), 3.95 (s, 4H), 7.05 (m, 2H), 7.58 (m, 2H); Analysis for: $C_{23}H_{34}N_2O_7S$ Calc'd: C, 57.24; H, 7.10; N, 5.80 Found: C, 57.27; H, 7.22; N, 5.84.

Step b) tert-Butyl 2-{[2-(tert-butoxy)-2-oxoethyl][(4-{4-[((2R)-2-hydroxy-2-{4-hydroxy-3-[(methylsulfonyl)amino] phenyl}ethyl)amino]-1-piperidinyl}phenyl)sulfonyl] amino}acetate Acetic acid (0.95 mL, 1.66 mmol) was added dropwise into a N-{5-[(1R)-2-amino-1-hydroxyethyl]-2-hydroxyphenyl}methanesulfonamide (204 mg, 0.83 mmol), tert-butyl 2-([2-(tert-butoxy)-2-oxoethyl-{[4-(4-oxo-1-piperidinyl) phenyl]sulfonyl}amino)acetate (400 mg, 0.83 mmol), and N,N-dimethylformamide (4 mL). The mixture was stirred for 20 minutes and then, sodium triacetoxyborohydride (211 mg, 0.99 mmol) was added, and the new mixture was stirred at room temperature for 24 hours. The volatiles were removed in vacuo and the residue was purified by flash chromatography (dichloromethane/methyl alcohol 8/1) to produce a white solid (520 mg, 88% yield): mp 164–166° C.; MS m/e 713 (M+H)$^+$; $^1$H NMR (400 MHz, DMSO-d$_6$): δ 1.27 (m, 2H), 1.31 (s, 18H), 1.84 (m, 2H), 1.62–1.75 (m, 3H), 2.85–2.95 (m, 5H), 38. (m, 2H), 3.93 (s, 4H), 4.5 (m, 1H), 6.8 (m, 1H), 6.98–7.01 (m 2H), 7.17 (1H), 7.51 (m, 2H); Analysis for: $C_{32}H_{48}N_4O_{10}S_2\times 1\ CH_3CO_2H$ Calc'd: C, 52.83; H, 6.78; N, 7.25 Found: C, 51.85; H, 6.61; N, 7.07.

EXAMPLE 55

2-((Carboxymethyl)[(4-{4-[((2R)-2-hydroxy-2-{4-hydroxy-3-[(methylsulfonyl)amino]phenyl)ethyl) amino]-1-piperidinyl}phenyl)sulfonyl]amino}acetic Acid A mixture of tert-butyl 2-([2-(tert-butoxy)-2-oxoethyl] [(4-{4-[((2R)-2-hydroxy-2-{4-hydroxy-3-[(methylsulfonyl) amino]phenyl}ethyl)amino]-1-piperidinyl}phenyl)sulfonyl] amino}acetate (400 mg, 0.56 mmol), dichloromethane (10 mL), and trifluoroacetic acid (3 mL) was stirred at room temperature for 15 hours. The mixture was then poured into ethyl ether (50 mL) and the precipitated solid was filtered and dried. The crude solid was dissolved in methyl alcohol (5 mL) and added slowly into ethyl ether (50 mL). The precipitated solid was filtered and dried to yield a white solid (465 mg, 67%): mp 163–166° C.; MS m/e 599 (M–H)$^+$; $^1$H NMR (400 MHz, DMSO-d$_6$): δ 1.5–1.6 (m, 2H), 2.0–2.1 (m, 2H), 2.8–3.2 (m, 8H), 3.8 m, 2H), 4.0 (M, 2H), 4.8 (m, 1H), 6.9 (m, 1H), 7.05 (m, 3H), 7.2 (m, 1H), 7.6 (m, 2H); Analysis for: $C_{24}H_{32}N_4O_{10}S_2\times 0.5\ CF_3CO_2H$ Calc'd: C, 44.97; H, 4.94; N, 8.52 Found: C, 44.74; H, 4.75; N, 8.19.

EXAMPLE 56

Ethyl 2-{[(4-{4-[((2R)-2-Hydroxy-2-{4-hydroxy-3-[(methylsulfonyl)amino]-phenyl}ethyl)amino]-1-piperidinyl}phenyl)sulfonyl]amino}acetate Step a) Ethyl 2-{[(4-Fluorophenyl)sulfonyl]amino}acetate N,N-Diisopropylethylamine (26.8 mL, 154.2 mmol) was added into a mixture of 4-fluorobenzenesulfonyl chloride (15 g, 77.1 mmol), glycine ethyl ester hydrochloride (10.7 g, 77.1 mmol) and tetrahydrofuran (200 mL). The mixture was stirred for 24 hours. The volatiles were then removed in vacuo, and the residue was taken in water and extracted with ethyl acetate. The organic extracts were dried over MgSO$_4$. Evaporation and purification by flash chromatography (hexanes/ethyl acetate 4/1) gave a white solid (19.6 g, 93% yield): mp 90–92° C.; MS m/e 260 (M–H)$^+$; $^1$H NMR (400 MHz, DMSO-d$_6$): δ 1.05 9t, J=7.02 Hz, 3H), 3.7 9d, J=7.25 Hz, 2H), 3.98 (q, J=7.02 Hz, 2H), 7.4 (m, 2H), 7.83 (m, 2H0, 8.23 (t, J=7.25 Hz, 1H); Analysis for: $C_{10}H_{12}FNO_4S$ Calc'd: C, 45.97; H, 4.63; N, 5.36 Found: C, 46.12; H, 4.50; N, 5.37.

Step b) Ethyl 2-({[4-(4-Hydroxy-1-piperidinyl)phenyl] sulfonyl}amino)acetate

A mixture of ethyl 2-[[(4-fluorophenyl)sulfonyl] amino}acetate (25 g, 95.8 mmol), 4-hydroxypiperidine (14.5 g, 143.7 mmol), potassium carbonate (19.8 g, 143.7 mmol), 1,3-dimethyl-3,4,5,6-tetrahydro-2(1H)-pyrimidinone (90 mL), and acetonitrile (60 mL) was stirred at 75° C. for 2 days. The mixture was poured into water and extracted with ethyl acetate. The organic extracts were dried over MgSO$_4$. Evaporation and purification by flash chromatography (hexanes/ethyl acetate 1/1) gave a white solid (5.6 g, 33% yield): mp 99–101° C.; MS m/e 343 (M+H)$^+$; $^1$H NMR (400 MHz, DMSO-d$_6$): δ 1.09 (t, J=7.01, 3H), 1.18–1.22 (m, 2H), 1.78–1.83 (m, 2H), 3.0–3.05 (m, 2H), 3.56 (d, J=7.24 Hz, 2H), 3.68–3.72 (m, 3H), 3.97 (q, J=7.01 Hz, 2H), 4.7 (m, 1H), 6.98 (m, 2H), 7.53 (m, 2H), 7.76 (t, J=7.24 Hz, 1H); Analysis for: $C_{15}H_{22}FN_2O_5S$ Calc'd: C, 52.62; H, 6.48; N, 8.18 Found: C, 52.64; H, 6.48; N, 8.17.

Step c) Ethyl 2-({[4-(4-oxo-1-Piperidinyl)phenyl] sulfonyl}amino)acetate

Trifluoroacetic acid (0.11 mL, 1.45 mmol) was added dropwise into a cold (0° C.) mixture of ethyl 2-({[4-(4-hydroxy-1-piperidinyl)phenyl]sulfonyl}amino)acetate (1.0 g, 2.9 mmol), dimethyl sulfoxide (7 mL), benzene (7 mL), pyridine (0.23 mL, 2.9 mmol), and 1,3-dicyclohexylcarbodiimide (1.79 g, 8.7 mmol). The mixture was allowed to come to room temperature, stirred for 20 hours, and then diluted with ethyl acetate. The precipitated solid was filtered and discarded. The filtrate was washed with water, and dried over MgSO$_4$. Evaporation and purification by flash chromatography (hexanes/ethyl acetate 2/1) gave a white solid (820 mg, 82% yield): mp 90–92° C.; MS m/e 341 (M+H)$^+$; $^1$H NMR (400 MHz, DMSO-d$_6$): δ 1.1 (t, J=7.08 Hz, 3H), 2.41–2.44 (m, 2H), 3.6 (d, J=7.23 Hz, 2H), 3.76 (m, 2H), 4.0 (q, J=7.08 Hz, 2H), 7.05 (m, 2H), 7.58 (m, 2H), 7.8 (t, J=7.23 Hz, 1H); Analysis for: $C_{15}H_{20}FN_2O_5S$ Calc'd: C, 52.93; H, 2.92; N, 8.23 Found: C, 53.07; H, 5.93; N, 8.24.

Step d) Ethyl 2-([(4-{4-[((2R)-2-Hydroxy-2-{4-hydroxy-3-[(methylsulfonyl)-amino]phenyl}ethyl)amino]-1-piperidinyl}phenyl)sulfonyl]amino}acetate Acetic acid (0.61 mL, 10.7 mmol) was added dropwise into a N-{5-[(1R)-2-amino-1-hydroxyethyl]-2-hydroxyphenyl}methanesulfonamide (1.32 g, 5.35 mmol), ethyl 2-({[4-(4-oxo-1-piperidinyl)phenyl]sulfonyl}amino) acetate (1.82, 5.35 mmol), and N,N-dimethylformamide (5 mL). The mixture was stirred for 20 minutes and then, sodium triacetoxyborohydride (1.36 g, 6.42 mmol) was added, and the new mixture was stirred at room temperature for 24 hours. The volatiles were removed in vacuo and the residue was purified by HPLC reverse phase (YMC C18 column, 17% MeOH: H$_2$O/0.1% AcOH) to produce a white solid (2.4 g, 90% yield): mp 105–107° C.; MS m/e 571 (M+H)$^+$; $^1$H NMR (400 MHz, DMSO-d$_6$): δ 1.09 (t, J=7.08, 3H), 1.25–1.35 (m, 2H), 1.8–1.85 (m, 2H), 2.6–2.7 (m, 3H), 2.82–2.91 (m, 5H), 3.56 (s, 3H), 3.8 (m, 2H), 3.97 (q, J=7.08 Hz, 2H), 4.5 (m, 1H), 6.8 (, m, 2H), 7.0 (m, 3H), 7.18 (m, 1H), 7.56 (m, 2); Analysis for: $C_{24}H_{34}N_4O_8S_2\times 1\ CH_3CO_2H$ Calc'd: C, 49.51; H, 6.07; N, 8.88 Found: C, 49.62; H, 6.23; N, 8.77.

EXAMPLE 57

Methyl 2-{[(4-{4-[((2R)-2-Hydroxy-2-{4-hydroxy-3-[(methylsulfonyl)amino]-phenyl}ethyl)amino]-1-piperidinyl}phenyl)sulfonyl]amino}acetate Step a) Methyl 2-({[4-(4-oxo-1-Piperidinyl)phenyl] sulfonyl}amino)acetate A mixture of tert-butyl 2-({[4-(4-oxo-1-piperidinyl) phenyl]sulfonyl}amino)acetate (1.0, 2.72 mmol) and formic acid (95%, 10 mL) was stirred at 60° C. for 3 hours. The volatiles were then removed in vacuo and the residue (847 mg) was taken in tetrahydrofuran (10 mL) and water (0.2 mL). The mixture was cooled to 0° C. and (trimethylsilyl) diazomethane (2 M, 2 mL) was added dropwise. The mixture was allowed to come to room temperature, stirred for 30 minutes, and then poured into water and extracted with ethyl acetate. The organic extracts were dried over MgSO$_4$. Evaporation and purification by flash chromatography (hexanes/ethyl acetate 2/1) gave a white solid (780 mg, 92% yield): mp 118–120° C.; MS m/e 327 (M+H)$^+$; $^1$H NMR (400 MHz, DMSO-d$_6$): δ 2.43 (m, 4H), 3.53 (s, 3H), 3.59 (d, J=6.37 Hz, 2H), 3.76 (m, 2H), 7.05 m, 2H), 7.59 (m, 2H), 7.82 (t, J=6.37 Hz, 1H); Analysis for: C$_{14}$H$_{18}$N$_2$O$_5$S Calc'd: C, 51.52; H, 5.56; N, 8.58 Found: C, 51.52; H, 5.57; N, 8.51

Step b) Methyl 2-{[(4-{4-[((2R)-2-hydroxy-2-{4-hydroxy-3-[(methylsulfonyl)-amino]phenyl}ethyl)amino]-1-piperidinyl}phenyl)sulfonyl]amino}acetate Acetic acid (0.26 mL, 4.12 mmol) was added dropwise into a N-{5-[(1R)-2-amino-1-hydroxyethyl]-2-hydroxyphenyl}methanesulfonamide (566 mg, 2.3 mmol), methyl 2-({[4-(4-oxo-1-piperidinyl)phenyl]sulfonyl}amino) acetate (750 mg, 0.23 mmol), and N,N-dimethylformamide 5 mL). The mixture was stirred for 20 minutes and then, sodium triacetoxyborohydride (585 mg, 2.76 mmol) was added, and the new mixture was stirred at room temperature for 24 hours. The volatiles were removed in vacuo and the residue was purified by flash chromatography (dichloromethane/methyl alcohol 8/1) to produce a white solid (1.15 mg, 90% yield): mp 123–125° C.; MS m/e 571 (M+H)$^+$; $^1$H NMR (400 MHz, DMSO-d$_6$): δ 1.2–1.3 (m, 2H), 1.8–187 (m, 2H), 2.6–2.75 (m, 3H), 2.9–2.97 (m, 5H), 3.51 (, 3H), 3.57 (s, 2H), 4.5 (m, 1H), 6.8 (m, 1H), 7.0 (m, 3H), 7.2 (m, 1H), 7.57 (m, 2H); Analysis for: C$_{24}$H$_{34}$N$_4$O$_8$S$_2$×1 CH$_3$CO$_2$H Calc'd: C, 48.69; H, 5.88; N, 9.08 Found: C, 49.02; H, 5.87; N, 9.29.

EXAMPLE 58

Ethyl 2-{[(4-{4-[((2R)-2-Hydroxy-2-{4-hydroxy-3-((methylsulfonyl)amino]-phenyl}ethyl)amino] piperidin-1-yl}phenyl)sulfonyl]amino}acetylcarbamate Step a) tert-Butyl ({[4-(4-oxopiperidin-1-yl)phenyl] sulfonyl}amino)acetate Trifluoroacetic acid (0.62 ml, 8.09 mmol) was added dropwise into a cold (0° C.) mixture of tert-butyl-({[4-(4-hydroxypiperidin-1-yl)phenyl]sulfonylamino)acetate (6 g, 16.2 mmol), 1,3-dicyclohexylcarbodiimide (10 g, 48.6 mmol), pyridine (1.31 mL, 16.2 mmol), methyl sulfoxide (45 mL) and benzene (45 mL). The new mixture was warmed up to room temperature and stirred for 18 hours, diluted with ethyl acetate (100 mL), and the precipitated solid was filtered and discarded. The organic filtrate was washed with water, and dried over MgSO$_4$. Evaporation and purification by flash chromatography (hexanes/ethyl acetate 6/4) gave a white solid (5.65 g, 90% yield): MS m/e 369 (M+H)$^+$; $^1$H NMR (DMSO-d$_6$ 400 MHz) δ 1.29 (s, 9 H), 2.42 (t, 4H), 3.46 (d, 2H), 3.72 (t, 4H), 7.07 (d, 2H), 7.56 (d, 2H), 7.58 (t, 1H).

Step b) 2-({[4-(4-oxo-1-Piperidinyl)phenyl] sulfonyl}amino)acetic Acid

A mixture of tert-butyl-({[4-(4-oxopiperidin-1-yl)phenyl]sulfonylamino)acetate (1.75 g, 4.75 mmol) and formic acid (96%, 7 mL) was stirred at 60° C. for 4 hours. The volatiles were removed in vacuo to give a yellow solid (1.1 g, 74% yield): MS m/e 311 (M–H)$^+$; $^1$H NMR (DMSO-d$_6$ 400 MHz) δ 2.45 (t, 4H), 3.58 (d, 2H), 3.80 (t, 4H), 7.17 (d, 2H), 7.64 (d, 2H), 7.72 (t, 1H), 12.7 (s, 1H).

Step c) Ethyl 2-({[4-(4-Oxopiperidin-1-yl)phenyl] sulfonyl}amino)acetylcarbamate A mixture of ({[4-(4-oxopiperidin-1-yl)phenyl] sulfonyl}amino)acetic acid (0.312 g, 1.0 mmol), ethyl (tert-butylimino)methylenecarbamate (0.6 mL), and tetrahydrofuran (3 mL) was reflux for 3 hours. The volatiles were removed in vacuo and the residue was purified by flash chromatography (hexanes/ethyl acetate 6/4) to give a white solid (0.17 g, 45% yield): MS m/e 382; (M–H)$^+$; $^1$H NMR (DMSO-d$_{6\ 300}$ MHz) δ 1.25(t, 3H), 2.50 (m, 4H), 3.4 (s, 2H), 3.81 (m, 4H), 4.18 (q, 2H), 7.15 (d, 2H), 7.65 (d, 2H), 10.65 (s, 1H).

Step d) Ethyl 2-{[(4-{4-[((2R)-2-hydroxy-2-{4-hydroxy-3-[(methylsulfonyl)-amino]phenyl}ethyl)amino]piperidin-1-yl}phenyl)sulfonyl]amino}-acetylcarbamate A mixture of ethyl 2-({[4-(4-oxopiperidin-1-yl)phenyl] sulfonyl}amino)acetylcarbamate (0.17 g, 0453 mmol) and N-{5-[(1R)-2-amino-1-hydroxyethyl]-2-hydroxyphenyl}methansulfonamide (0.115 g, 0.4674 mmol), sodium triacetoxyborohydride (0.19 g, 0.90 mmol), acetic acid (0.1 mL) in N,N-dimethylformamide (2.2 mL) was stirred at room temperature for 18 hours. The solvent was removed in vacuo and the residue was purified by flash chromatography (methylene chloride/methanol/ammonium hydroxide 8/2/0.001) to give a white solid (0.17 g, 61% yield): mp 98–105° C., MS m/e 614 (M+H)$^+$; $^1$H NMR (DMSO-d$_6$ 400 MHz) δ 1.17 (t, 3H), 1.29 (m, 2H), 1,88 (m, 2H), 2.67 (m, 3H), 2.90 (m, 5H), 3.80 (m, 4H), 4.07 (q, 2H), 4.48 (m, 1H), 6.82 (d, 1H), 6.99 (m, 3H), 7.16 (s, 1H), 7.51 (d, 2H); Analysis for C$_{25}$H$_{35}$N$_5$O$_9$S$_2$×1.0 CH$_3$COOH×0.63 H$_2$O Calc'd: C, 47.40; H, 5.78; N, 10.21 Found: C, 47.35; H, 6.02; N, 10.00.

EXAMPLE 59 tert-Butyl [[(4-{4-[((2R)-2-Hydroxy-2-{4-hydroxy-3-[(methylsulfonyl)amino]-phenyl}ethyl)amino] piperidin-1-yl}phenyl)sulfonyl](methoxycarbonyl)-amino]acetate Step a) tert-Butyl ((Methoxycarbonyl){[4-(4-oxopiperidin-1-yl)phenyl]-sulfonyl}amino)acetate Sodium hydride (60% in mineral oil, 0.18 g, 4.6 mmol) was added portionwise to a cold (0° C.) mixture of tert-butyl-({[4-(4-oxopiperidin-1-yl)phenyl]sulfonyl}amino) acetate (1.5 g, 4.07 mmol) and N,N-dimethylformamide (8 mL). The mixture was stirred for 1 hour and then methyl chloroformate (0.36 mL, 4.6 mmol) in N,N-dimethylformamide (0.5 mL) was added dropwise. The new mixture was warmed up to room temperature and stirred for 5 hours, poured into water, neutralized to pH 7 with saturated aqueous bicarbonate solution, and extracted with ethyl acetate. The organic extracts were washed with brine, and dried over MgSO$_4$. Evaporation and purification by flash chromatography (hexanes/ethyl acetate 6/4) gave a white solid (0.64 g, 37 %): $^1$H NMR (DMSO-d$_6$ 300 MHz) δ 1.41 (s, 9H), 2.52 (m, 4H), 3.63 (s, 3H), 3.81 (m, 4H), 4.41(s, 2H), 7.12 (d, 2H), 7.79 (d, 2H).

Step b) tert-Butyl [[(4-{4-[((2R)-2-Hydroxy-2-{4-hydroxy-3[(methylsulfonyl)-amino]phenyl}ethyl)amino]piperidin-1-yl}phenyl)sulfonyl]-(methoxycarbonyl) amino]acetate This compound was prepared from tert-butyl ((methoxycarbonyl){[4-(4-oxopiperidin-1-yl)phenyl] sulfonyl}amino)acetate and N-{5-[(1R)-2-amino-1-hydroxyethyl]-2-hydroxyphenyl}methanesulfonamide in substantially the same manner as described in Example 50, and was obtained as a white solid (0.3 g, 62%): mp 110–115° ° C.; MS m/e 657 (M+H)$^+$; $^1$H NMR (DMSO-d$_6$ 400 MHz) δ 1.24 (m, 2H), 1.38 (s, 9 H), 1.89 (m, 2H), 2.66 (m, 3H), 2.91 (s, 3H), 2.99 (m, 2H), 3.6 (s, 3H), 3.88 (m, 2H), 4.47 (s, 2H), 4.49 (m, 1H), 6.82 s, 1H), 6.99 (m, 3H), 7.17 s, 1H), 7.67 (d, 2H); Analysis for C$_{28}$H$_{40}$N$_4$O$_{10}$S$_2$×0.8 CH$_3$COOH× 0.41 H$_2$O Calc'd: C, 50.34; H, 6.05; N, 7.83 Found: C, 50.06; H, 6.40; N, 7.52.

EXAMPLE 60

[[(4-{4-[((2R)-2-Hydroxy-2-{4-hydroxy-3-[(methylsulfonyl)amino]phenyl}-ethyl)amino]piperidin-1-yl}phenyl)sulfonyl](methoxycarbonyl)amino]acetic Acid This compound was prepared from tert-butyl [[(4-{4-[((2R)-2-hydroxy-2-{4-hydroxy-3[(methylsulfonyl)amino]phenyl}ethyl)amino]piperidin-1-yl}phenyl)sulfonyl](methoxycarbonyl)amino]acetate in substantially the same manner as described in Example 53, with one change; the mixture was stirred at room temperature for 20 hours. The volatiles were removed and the product was purified by reverse phase chromatography to give a white solid (0.08 g, 45% yield): mp 60° C., MS m/e 601 (M+H)$^+$; $^1$H NMR (DMSO-$d_6$ 400 MHz) δ 1.60 (m, 2H), 2.08 (m, 2H), 2.86 (m, 2H), 2.93 (s, 3H), 2.94 (m, 2H), 3.08 (m, 1H), 3.59 (s, 3H), 4.06 (m, 2H), 4.42 (s, 3H), 4.76 (m, 1H), 6.89 (d, 1H), 7.04 (m, 3H), 7.23 s, 1H), 7.70 (d, 2H); Analysis for $C_{24}H_{32}N_4O_{10}S_2 \times 2.0$ $CF_3COOH \times 0.63$ $H_2O$ Calc'd: C, 40.00; H, 3.96; N, 6.66 Found: C, 37.84; H, 3.77; N, 5.87.

EXAMPLE 61

Ethyl {(2,5-Difluorobenzyl)[(4-{4-[((2R)-2-hydroxy-2-{4-hydroxy-3-[(methyl-sulfonyl)amino]phenyl}ethyl)amino]piperidin-1-yl}phenyl)sulfonyl]amino}acetate Step a) N-(2,5-Difluorobenzyl)-4-fluorobenzenesulfonamide A solution of 2,4-difluorobenzyl amine (9.5 g, 66.37 mmol) in methylene chloride (15 mL) was added dropwise into a cold (–10° C.) mixture of 4-fluorobenzenesulfonyl chloride (15.6 g, 80 mmol), diisopropylethyl amine (18.1 mL, 104 mmol) and methylene chloride (80 mL). The new mixture was warmed up to room temperature, stirred for 4 hours, poured into water, acidified with aqueous hydrochloric acid (2 N), and extracted with methylene chloride. The organic extracts were washed with brine, and dried over MgSO$_4$. Evaporation and purification by flash chromatography (hexanes/ethyl acetate 8/2) gave an off white solid (12.5 g, 63% yield): MS m/e 300 (M–H)$^+$; $^1$H NMR (DMSO-$d_6$ 400 MHz) δ 4.13 (d, 2H), 7.19 (m, 3H), 7.41 (d, 2H), 7.84(d, 2H), 8.36 (t, 1H).

Step b) N-(2,5-Difluorobenzyl)-4-(1,4-dioxa-8-azaspiro[4.5]dec-8-yl)-benzenesulfonamide A mixture of N-(2,5-difluorobenzyl)-4-fluorobenzenesulfonamide (12.1 g, 40.16 mmol) and 1,4-dioxa-8-azaspiro[4.5]decane (9.9 ml) was heated at 65° C. for 6 days. The product was purified by flash chromatography (hexanes/ethyl acetate 7/3) to give a white solid 10.4 g, 62% yield), mp 135° C.; MS m/e 425 (M+H)$^+$; $^1$H NMR (DMSO-$d_6$ 400 MHz) δ 1.6 (m,4H), 3.42 (m, 4H), 3.91 (s, 4H), 3.98(d, 2H), 6.99 (d, 2H), 7.04 (m, 3H), 7.50 (d, 2H), 7.89(t, 1H).

Step c) N-(2,5-Difluorobenzyl)-4-(4-oxopiperidin-1-yl)benzenesulfonamide

N-(2,5-difluorobenzyl)-4-fluorobenzenesulfonamide (4.5 g, 10.60 mmol) was treated at –10° C. with concentrated hydrochloric acid (50 mL). The mixture was warmed up to room temperature, stirred for 24 hours, neutralized with ammonium hydroxide at 0° C. and extracted with methylene chloride. The organic extracts were washed with brine, and dried over MgSO$_4$. The solvent was removed in vacuo to give an off white solid (4.1 g, 94% yield): mp 119° C.; MS m/e 379 (M–H)$^+$; $^1$H NMR (DMSO-$d_6$ 400 MHz) δ 2.47 (m,4H), 3.70 (m, 4H), 4.15 (d, 2H), 7.10 (d, 2H), 7.19 (m, 3H), 7.62 (d, 2H), 8.01 (t, 1).

Step d) Ethyl ((2,5-Difluorobenzyl){[4-(4-oxopiperidin-1-yl)phenyl]-sulfonyl}amino)acetate A mixture of N-(2,5-difluorobenzyl)-4-(4-oxopiperidin-1-yl)benzenesulfonamide (2 g, 5.25 mmol), potassium carbonate (0.8 g, 5.78 mmol), ethyl bromoacetate (0.64 mL, 5.78 mmol) and acetonitrile (20 mL) was reflux for 18 hours. After cooling to room temperature the mixture was poured into aqueous ammonium chloride and extracted with ethyl acetate. The organic extracts were washed with brine, and dried over MgSO$_4$. Evaporation and purification by flash chromatography (hexanes/ethyl acetate 6/4) gave a light yellow oil (1.49 g, 60% yield): MS m/e 465 (M–H)$^+$; $^1$H NMR (DMSO-$d_6$ 400 MHz) δ 1.08 (t,3H), 2.48 (m, 4H), 3.75 (m, 4H), 3.94 (q, 2H), 3.97 (s, 2H), 4.38 (s, 2H), 7.08 (d, 2H),7.19 (m, 3H), 7.64 (d, 2H).

Step e) Ethyl {(2,5-Difluorobenzyl)[(4-{4-[((2R)-2-hydroxy-2-{4-hydroxy-3-[(methylsulfonyl)amino]phenyl}ethyl)amino]piperidin-1-yl}phenyl)sulfonyl]amino}acetate This compound was prepared from ethyl ((2,5-difluorobenzyl){[4-(4-oxopiperidin-1-yl)phenyl]sulfonyl}amino)acetate, and N-{5-[(1R)-2-amino-1-hydroxyethyl]-2-hydroxyphenyl}methansulfonamide in substantially the same manner as described in example 7, step d, with one change; the product was purified by reverse phase chromatography and was obtained as a white solid (1.25 g, 49% yield): mp 85–90° C.; MS m/e 697 (M+H)$^+$; $^1$H NMR (DMSO-$d_6$ 400 MHz) δ 1.07, (t, 3H), 1.31 (m, 2H), 1.89 (m 2H), 2.67 (m, 2H), 2.70 (m, 1), 2.91 (s, 3H), 2.94, (m, 2H), 3.91 (m, 1H), 3.94 (q, 2H), 3.95 (s, 2H), 4.36, (s, 2H), 4.51 (m, 1H), 6.83 (d, 1H), 6.99 (m, 3H), 7.19 (m, 4H), 7.55 (d, 2H); Analysis for $C_{31}H_{38}F_2N_4O_8S_2 \times 2.0$ $CH_3COOH$ Cald'd: C, 45.45, H, 4.36; N, 6.28 Found: C, 46.23; H, 4.38; N, 6.28.

EXAMPLE 62

1-[4-({[(Butylamino)carbonyl]amino}sulfonyl)phenyl]-4-[((2)-2-hydroxy-2-{4-hydroxy-3-[(methylsulfonyl)amino]phenyl}ethyl)amino]piperidine Step a) 1-(3-Bromoisoxazol-5-yl)ethanone A solution of 4-fluorobenzenesulfonyl chloride (76 g, 0.39 mol) in tetrahydrofuran (200 mL) was added slowly into a cold (-40° C.) saturated tetrahydrofuran/ammonia solution (200 mL). The resulting suspension was allowed to come to room temperature and stirred for 20 hours.The suspension was filtered and the solid washed with ethyl acetate. The organic filtrate was concentrated in vacuo and the product was crystallized from ethyl acetate/hexanes to give a white solid (63 g, 92% yield): MS m/e 174 (M–H)$^+$; $^1$H NMR (DMSO-$d_6$ 300 MHz) δ 7.42, (m, 4H), 7.85 (m, 2H).

Step b) 4-(1,4-Dioxa-8-azaspiro[4.5]dec-8-yl)benzenesulfonamide

A mixture of 1-(3-bromoisoxazol-5-yl)ethanone (5.3 g, 30.28 mmol) and 1,4-dioxa-8-azaspiro[4.5]decane (7.4 mL) was warmed at 65° C. for 4 days. After cooling to room temperature, the mixture was triturated with methylene chloride to give a white solid (3.0 g, 33 % yield): MS m/e 297 (M–H); $^1$H NMR (DMSO-$d_6$ 300 MHz) δ 1.69 (m, 4H),3.22 (m, 4H), 3.80 (s, 4H), 7.04 (d, 2H), 7.60 (d, 2H).

Step c) 1-[4-({[(Butylamino)carbonyl]amino}sulfonyl)phenyl]-4-oxopiperidine

Sodium hydride (60% in mineral oil, 0.1 9, 2.5 mmol) was added at room temperature into a mixture of 4-(1,4-dioxa-8-azaspiro[4.5]dec-8-yl)benzenesulfonamide (0.5 g, 1.67 mmol) and tetrahydro furan (10 mL). After stirring for 18 hours, n-butyl isocyanate (0.28 mL, 2.5 mmol) was added, and stirring was continued overnight. The mixture was cooled to 0° C. and acidified with concentrated hydrochloric acid (7 mL). The new mixture was allowed to come to room temperature, stirred for another 18 hours, neutralized with ammonium hydroxide at ) ° C., and extracted with ethyl acetate. The organic extracts were washed with brine, and dried over $MgSO_4$. Evaporation and purification by flash chromatography (hexanes/methylene chloride/isopropyl alcohol 5/4/1) gave a white solid (0.34 g, 57% yield): MS m/e 352 (M–H)$^+$; $^1$H NMR (DMSO-$d_6$ 300 MHz) δ 0.96, (t, 3H), 1.23 (m, 2H), 1.38, (m, 2H), 2.46 (m, 2H), 2.98, (m, 4H), 3.84 (m, 4H), 6.40, (t, 1H), 7.15 (d, 2H), 7.78 (d, 2H), 10.21 (s, 1H).

Step d) 1-[4-({[(Butylamino)carbonyl]amino}sulfonyl) phenyl]-4-[((2R)-2-hydroxy-2-{4-hydroxy-3-[(methylsulfonyl)amino]phenyl}ethyl)amino]piperidine This compound was prepared from 1-[4-({[(butylamino) carbonyl]amino}sulfonyl)phenyl]-4-oxopiperidine, and N-{5-[(1R)-2-amino-1-hydroxyethyl]-2-hydroxyphenyl}methansulfonamide in substantially the same manner, as described in Example 50, with one change; the product was purified by reverse phase chromatography and was obtained as a white solid (0.16 g, 23% yield): mp 100–102° C., MS m/e 584 (M+H)$^+$; $^1$H NMR (DMSO-$d_6$ 400 MHz) δ 0.75, (t, 3H), 1.13 (m, 2H), 1.23 (m 2H),1.44 (m, 2H), 1.93 (m, 2H), 2.79 (m, 2H), 2.85 (m, 2H), 2.87 (m, 2H), 2.90 (s, 3H), 3.04 (m, 1H),3.86 (m, 4H), 4.66 (m, 1H), 6.85 (d, 1H), 6.93 (d, 2H), 7.04 (m, 1H), 7.18 (d, 1H), 7.56, (d, 2H); Analysis for $C_{25}H_{37}N_5O_7S_2 \times 2.0$ $CH_3COOH \times 067$ $H_2O$ Cald'd: C, 48.67; H, 6.48; N, 9.79 Found: C, 46.16; H, 6.62; N, 9.81.

EXAMPLE 63

2-{(2,5-Difluorobenzyl)[(4-{4-[((2R)-2-hydroxy-2-{4-hydroxy-3-[(methylsulfonyl)-amino] phenyl}ethyl)amino]-1-piperidinyl}phenyl)sulfonyl] amino}acetic acid Step a) tert-Butyl 2-((2,5-Difluorobenzyl){[4-(4-oxo-1-piperidinyl)phenyl]-sulfonyl}amino)acetate Sodium hydride (60% in mineral oil, 0.49 9, 12.27 mmol) was added portionwise to a cold (0° C.) mixture of tert-butyl(([4-(4-oxopiperidin-1-yl)phenyl]sulfonyl}amino) acetate (4.0 g, 10.85 mmol) and N,N-dimethylformamide (60 mL). The mixture was stirred for 2 hours, and then 2,5-difluorobenzyl bromide (1.4 mL, 10.85 mmol) in N,N-dimethylformamide (5 mL) was added dropwise. The new mixture was stirred at 0° C. for 2 hours, poured into aqueous ammonium chloride, and extracted with ethyl acetate. The organic extracts were washed with brine, and dried over $MgSO_4$. Evaporation and purification by flash chromatography (hexanes/ethyl acetate 6/4) gave a white solid (3.2 g, 60% yield): MS m/e 495 (M+H)$^+$; $^1$H NMR (DMSO-$d_6$ 300 MHz) δ 1.38 (s, 9 H), 2.45 (m, 4H), 3.78 (m, 4H), 3.85 (s, 2H), 4.2 (s, 2H), 7.15 (d, 2H), 7.20 (m, 3H), 7.74 (d, 2H).

Step b) tert-Butyl 2-{(2,5-difluorobenzyl)[(4-{4-[((2R)-2-hydroxy-2-{4-hydroxy-3-[(methylsulfonyl)amino] phenyl}ethyl)amino]-1-piperidinyl}phenyl)-sulfonyl] amino}acetate This compound was prepared from tert-butyl 2-((2,5-difluorobenzyl){[4-(4-oxo-1-piperidinyl)phenyl] sulfonyl}amino)acetate and N-{5-[(1R)-2-amino-1-hydroxyethyl]-2-hydroxyphenyl}methanesulfonamide in substantially the same manner, as described in Example 50, and was obtained as a white solid (2.9 g, 63% yield): MS m/e 725 (M+H)$^+$; $^1$H NMR (DMSO-$d_6$ 400 MHz) δ 1.27, (s, 9 H), 1.29 (m, 2H), 1.88 (m 2H), 2.68 (m, 2H), 2.72 (m, 1H), 2.88 (m, 2H), 2.91 (s, 3H), 3.83 (m, 4H), 4.35 (s, 2H), 4.50 (m, 1H), 6.83 (d, 1H), 7.01 (m, 3H), 7.18 (m, 4H), 7.56 (d, 2H).

Step c) 2-{(2,5-Difluorobenzyl)[(4-{4-[((2R)-2-hydroxy-2-{4-hydroxy-3-[(methylsulfonyl)amino]phenyl}ethyl) amino]-1-piperidinyl}phenyl)sulfonyl]amino}acetic Acid This compound was prepared from tert-butyl 2-{(2,5-difluorobenzyl)[(4-{4-[((2R)-2-hydroxy-2-{4-hydroxy-3-[(methylsulfonyl)amino]phenyl}ethyl)amino]-1-piperidinyl}phenyl)sulfonyl]amino}acetate in substantially the same manner, as described in Example 53, with one change; the mixture was stirred at room temperature for 20 hours. The volatiles were removed and the product was purified by reverse phase chromatography to give a white solid (1.44 9, 42% yield): mp 80–82° C.; MS m/e 669 (M+H)$^+$; $^1$H NMR (DMSO-$d_6$ 400 MHz) 81.62 (m, 2H), 2.11 (m, 2H), 2.85 (m, 2H), 2.94 (s, 3H), 2.96 (m, 1H), 3.11 (m, 1H), 3.34 (m, 1H), 3.88 (s, 2H), 3.99 (m, 2H), 4.37 (s, 2H), 4.79 (m, 1H), 6.01 (br, 1H), 6.90 (d, 1H), 7.05 (m, 3H), 7.18 (m, 3H), 7.21 (s, 1H), 7.59 (d, 2H), 8.58 (brs, 1H), 8.66 (brs, 1H), 8.74 (brs, 1H), 10.01 (brs, 1H); Analysis for $C_{29}H_{34}F_2N_4O_8S_2 \times 2.0$ $CF_3COOH \times 0.73$ $H_2O$ Calc'd: C, 43.52; H, 4.11 ; N, 6.15 Found: C, 42.95; H, 3.93; N, 6.08.

EXAMPLE 64

Ethyl {4-((4-{4-[((2R)-2-Hydroxy-2-{4-hydroxy-3-[(methylsulfonyl)amino]-phenyl}ethyl)amino] piperidin-1-yl}phenyl)sulfonyl]piperazin-1-yl}acetate Step a) Ethyl 2-{4-[(4-fluorophenyl)sulfonyl]-1-piperazinyl}acetate 4-Fluorobenzenesulfonyl chloride (10 g, 50.4 mmol) was added into a cold (0° C.) solution of 1-(ethoxycarbonylmethyl-piperazine) (5.64 mL, 50.4 mmol) and N,N-diisopropylethylamine (9.13 mL, 55.4 mmol) in tetrahydrofuran (100 mL) over a period of 20 minutes. The mixture was then stirred at room temperature overnight. The mixture was concentrated and water was added. The aqueous mixture was extracted with ethyl acetate. The extracts were washed with water, dried with magnesium sulfate. The extracts were concentrated to give an oil (16.38 9, 97% yield): $^1$H NMR (300 MHz, DMSO-$d_6$): δ 1.13–1.18 (t, 3H), 2.55–2.60 (m, 4H), 2.86–2.90 (m, 4H), 3.22 (s, 2H), 4.01–4.06 (q, 2H), 7.46–7.51 (m, 2H), 7.79–7.83 (m, 2H); MS m/z 331 (M+H)$^+$; Analysis for $C_{14}H_{19}FN_2O_4S$ Calc'd: C, 50.90; H, 5.80; N, 8.48; Found: C, 50.97; H, 5.87; N, 8.56.

Step b) Ethyl 2-(4-{[4-(4-oxo-1-Piperidinyl)phenyl] sulfonyl}-1-piperazinyl)acetate A mixture of ethyl 2-{4-[(4-fluorophenyl)sulfonyl]-1-piperazinyl}acetate (8 9, 24.2 mmol), 4-piperidone hydrochloride monohydate (5.58 g, 36.3 mmol) and potassium carbonate (10.0 g, 72.66 mmol) in 1, 3-dimethyl-3,4,5,6-tetrahydro-2(1H)-pyrimidine (25 ML) and acetonitrile was stirred at 75° C. for 3 days. The mixture was diluted with water and extracted with ethyl acetate. The extract were washed with water and dried with $MgSO_4$. Evaporation and purification by flash column chromatography (dichloromethane/ethyl acetate 1/1) gave a white solid (0.55 g, 6% yield): mp: 81–83° C.; $^1$H NMR (400 MHz, DMSO-$d_6$): δ 1.13–1.17 (t, 3H), 2.45–2.47 (m, 4H), 2.48–2.50 (m, 4H), 2.82–2.85 (m, 4H), 3.21 (s, 2H), 3.74–3.77 (m, 4H), 4.01–4.07 (q, 2H), 7.09–7.12 (d, 2H), 7.50–7.54 (d, 2H); MS m/z 409 M$^+$.

Step c) Ethyl {4-[(4-(4-[((2R)-2-Hydroxy-2-{4-hydroxy-3-[(methylsulfonyl)-amino]phenyl}ethyl)amino]piperidin-1-yl}phenyl)sulfonyl]piperazin-1-yl}acetate The title compound was prepared from N-{5-[(1R)-2-amino-1-hydroxyethyl]-2-hydroxyphenyl}methanesulfonamide and ethyl 2-(4-{[4-(4-oxo-1-piperidinyl)phenyl]sulfonyl}-1-piperazinyl)acetate in substantially the same manner, as described in Example 50. The product was obtained as a light yellow solid; mp: 91–92° C.; $^1$H NMR (400 MHz, DMSO-$d_6$): δ 1.08–1.17 (t, 3H), 1.49–1.56 (m, 2H), 2.02–2.07 (m, 2H), 2.45–2.50 (m, 4H), 2.52–56 (m, 2H), 2.74–80 (m, 2H), 2.86–3.01 (m, 5H), 3.20 (s, 2H), 3.24–3.36 (m, 4H), 3.96–3.99 (d, 2H), 4.01–4.07 (q, 2H), 4.69–4.71 (m, 1H), 6.86–6.88 (d, 2H), 7.05–7.09 (m, 3H), 7.23–7.24 (m, 1), 7.47–7.50 (d, 2H), 8.20 (brs, 4H); MS m/z 640 (M+H)$^+$; Analysis for $C_{28}H_{41}N_5O_8S_2$×1.0 $F_3CCO_2H$×0.18 $CH_2Cl_2$ Calc'd: C, 47.13; H, 5.55; N, 9.11; Found: C, 47.02; H, 5.75; N, 8.67.

EXAMPLE 65

{(4-[(4-{4-[((2R)-2-Hydroxy-2-{4-hydroxy-3-[(methylsulfonyl)amino]phenyl}-ethyl)amino]piperidin-1-yl}phenyl)sulfonyl]piperazin-1-yl}acetic Acid, Sodium Salt A solution of ethyl {4-[(4-{4-[((2R)-2-hydroxy-3-[(methylsulfonyl)amino]phenyl}ethyl)amino]piperidin-1-yl}phenyl)sulfonyl]-piperazin-1-yl}acetate (1.0 g, 1.02 mmol) and 1N aqueous sodium hydroxy (4.1 mL, 4.1 mmol) in methyl alcohol-tetrahydrofuran (1/1) was stirred at room temperature overnight. The solvent was removed in vacuo and chased with benzene. Methyl alcohol (60 mL) was added and the solid was isolated by filtration. The filtrate was then concentrated to give a brown solid; mp 131° C. (decomposed): $^1$H NMR (400 MHz, DMSO-$d_6$): δ 1.22–1.27 (m, 2H), 1.80–1.87 (m, 2H), 2.46–2.48 (m, 4H), 2.57–2.67 (m, 6H), 2.80–2.89 (m, 4H), 2.90–2.98 (m, 2H), 3.16 (s, 3H), 3.78–3.82 (m, 2H), 4.34–4.37 (m, 1H), 6.45–6.51 (m, 2H), 7.01–7.04 (d, 2H), 7.44–7.46 (d, 2H); MS m/z 612 (M+H)$^+$; Analysis for $C_{26}H_{35}N_5O_8S_2Na_2$×3.0 $F_3CCO_2Na$×0.47 $H_2O$×1.0 $CH_3OH$ Calc'd: C, 37.94; H, 4.04; N, 6.71; Found: C, 37.40; H, 3.98; N, 6.69.

EXAMPLE 66

N-(2-Hydroxy-5-{(1R)-1-hydroxy-2-[(1-{4-[(4-methylpiperazin-1-yl)sulfonyl]phenyl}piperidin-4-yl)amino]ethyl}phenyl)methanesulfonamide Step a) 1-[(4-Fluorophenyl)sulfonyl]-4-methylpiperazine The title compound was prepared from 4-fluorobenzenesulfonyl chloride, 1-methylpiperazine in substantially the same manner, as described in example 9, step a. The product was obtained as an oil; $^1$H NMR (300 MHz, DMSO-$d_6$): δ 2.12 (s, 3H), 2.31–2.37 (m, 4H), 2.85–2.92 (m, 4H), 7.46–7.52 (m, 2H), 7.76–7.82 (m, 2H); MS m/z 259 (M+H)$^+$; Analysis for $C_{11}H_{15}FN_2O_2S$ Calc'd: C, 51.15; H, 5.85; N, 10.84; Found: C, 51.18; H, 5.81; N, 10.90.

Step b) 1-{4-[(4-Methyl-1-piperazinyl)sulfonyl]phenyl)-4-piperidinone

The title compound was prepared from 1-[(4-fluorophenyl)sulfonyl]-4-methylpiperazine and 4-piperidone hydrochloride monohydate in substantially the same manner, as described in Example 64. The product was obtained as a semi-solid: $^1$H NMR (300 MHz, DMSO-$d_6$): δ 2.12 (s, 3H), 2.33–2.35 (m, 4H), 2.45–2.50 (m, 4H), 2.74–2.82 (m, 4H), 3.73–3.76 (m, 4H), 7.08–7.12 (d, 2H), 7.50–7.53 (m, 2H); MS m/z 338 (M+H)$^+$; Analysis for $C_{16}H_{23}N_3O_3S$ Calc'd: C, 56.95; H, 6.87; N, 12.45; Found: C, 57.03; H, 6.89; N, 12.38.

Step c) N-(2-Hydroxy-5-{(1R)-1-hydroxy-2-[(1-{4-[(4-methylpiperazin-1-yl)sulfonyl]phenyl}piperidin-4-yl)amino]ethyl}phenyl)methanesulfonamide The title compound was prepared from N-{5-[(1R)-2-amino-1-hydroxyethyl]-2-hydroxyphenyl}methanesulfonamide, and 1-{4-[(4-methyl-1-piperazinyl)sulfonyl]phenyl}-4-piperidinone in substantially the same manner, as described in Example 50. The product was obtained as a brown solid; mp: 89–91° C.; $^1$H NMR (400 MHz, DMSO-$d_6$): δ 1.53–1.65 (m, 2H), 2.06–2.16 (m, 2H), 2.82–2.89 (m, 2H), 2.94 (s, 3H), 3.09–3.13 (m, 2H), 3.70 (brs, 2H), 4.01–4.05 (m, 2H), 4.76–4.79 (d, 2H), 6.11 (brs, 1H), 6.88–6.90 (d, 2H), 7.06–7.13 (m, 4H), 7.25 (s, 1H), 7.52–7.55 (d, 2H), 8.60 (brs, 1H); 8.58 (brs, 1H); 8.75 (s, 1H), 9.64 (brs, 1H), 10.00 (s, 1H); MS m/z 568 (M+H)$^+$; Analysis for $C_{25}H_{37}N_5O_6S_2$×0.4 hexane×0.52 $H_2O$ Calc'd: C, 42.07; H, 4.93; N, 7.34; Found: C, 42.27; H, 4.60; N, 6.70.

EXAMPLE 67 tert-Butyl {(2,5-difluorobenzyl)[(4-{4-[((2R)-2-hydroxy-2-{4-hydroxy-3-[(methylsulfonyl)amino]phenyl}ethyl)amino]piperidin-1-yl}phenyl)sulfonyl]-amino}acetate Step a) tert-Butyl 2-((2,5-Difluorobenzyl){[4-(4-oxo-1-piperidinyl)-phenyl]sulfonyl}amino)acetate Sodium hydride (60% in mineral oil, 0.12 g, 8.13 mmol) was added portionwise to a cold (0° C.) solution of tert-butyl 2-({[4-(4-oxo-1-piperidinyl)phenyl]sulfonyl}amino)acetate (1.0 g, 2.71 mmol) in N,N-dimethylformamide (15 mL) under a nitrogen atmosphere. After stirring for 1 hour a-bromo-2,5-difluorotoluene (0.36 mL, 2.71 mmol) was added dropwise over a period of 10 minutes. The mixture was then stirred at 0° C. for 2 hours. The reaction was quenched with aqueous ammonium chloride to pH 5 and extracted with ethyl acetate. The extracts were washed with water and dried with magnesium sulfate. The extracts were concentrated to give a solid (1.3 g, 97% yield): $^1$H NMR (400 MHz, DMSO-$d_6$): δ 1.28 (s, 9 H), 2.42–2.45 (m, 4H), 3.73–3.77 (m, 4H), 3.86 (s, 2H), 4.37 (s, 2H), 7.07–7.09 (d, 2H), 7.16–7.21 (jm, 3H), 7.62–7.65 (d, 2H); MS m/z 495 (M+H)$^+$; Analysis for $C_{24}H_{28}F_2N_2O_5S$×Calc'd: C, 58.29; H, 5.71; N, 5.66; Found: C, 58.55; H, 6.03; N, 5.44.

Step b) tert-Butyl {(2,5-Difluorobenzyl)[(4-{4-[((2R)-2-hydroxy-2-{4-hydroxy-3-[(methylsulfonyl)amino]phenyl}ethyl)amino]piperidin-1-yl}phenyl)sulfonyl]-amino}acetate The title compound was prepared from N-{5-[(1R)-2-amino-1-hydroxyethyl]-2-hydroxyphenyl}methanesulfonamide and ethyl 2-((2,5-difluorobenzyl){[4-(4-oxo-1-piperidinyl)phenyl]sulfonyl}amino)acetate in substantially the same manner, as described in Example 50. The product was obtained as a white solid: $^1$H NMR (400 MHz, DMSO-$d_6$): δ 1.28 (s, 9H), 1.30–1.40 (m, 2H), 1.89–1.96 (m, 2H), 4.48–4.50 (m, 4H), 2.69–2.92 (m, 4H), 2.72 (s, 3H), 3.84–3.89 (m, 3H), 4.36 (s, 2H), 4.56–4.59 (m, 1H), 6.83–6.85 (m, 1H), 7.00–70.04 (m. 3H), 7.14–7.23 (m, 4H), 7.57–7.60 (d, 2H), 8.21 (s, 1H); MS m/z 725 (M+H)$^+$; Analysis for $C_{33}H_{42}F_2N_4O_8S_2$×1.0 $HCO_2H$ Calc'd: C, 52.98; H, 5.75; N, 7.27; Found: C, 51.24; H, 5.77; N, 7.14.

What is claimed is:

1. A compound of formula I having the structure

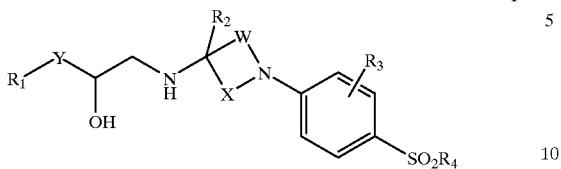

wherein:

W is $(CH_2)_m$;

X is $(CH_2)_n$;

Y is $OCH_2$, $SCH_2$, or a bond;

$R_1$ is phenyl substituted with $R_5$ and $R_6$, or Het substituted with $R_5$ and $R_6$;

$R_2$ is hydrogen, trifluoromethyl, alkyl of 1–6 carbon atoms, alkenyl of 2–7 carbon atoms, or alkynyl of 2–7 carbon atoms;

$R_4$ is alkyl of 1–6 carbon atoms, alkenyl of 2–7 carbon atoms, alkynyl of 2–7 carbon atoms, cycloalkyl of 3–8 carbon atoms, hydroxy, aryl substituted with $R_5$ and $R_6$, Het substituted with $R_5$ and $R_6$, aryloxy, —NHCOR$_7$, —NR$_8$R$_8$, —CR$_3$R$_5$R$_6$, arylamino, Het-amino, arylalkylamino having 1–6 carbon atoms in the alkyl chain, Het-alkylamino having 1–6 carbon atoms in the alkyl chain, alkoxycarbonylalkyl of 3–13 carbon atoms, carboxyalkyl of 2–7 carbon atoms, alkylcarbonylalkyl of 3–13 carbon atoms, arylcarbonylalkyl having 1–6 carbon atoms in the alkyl chain, Het-carbonylalkyl having 1–6 carbon atoms in the alkyl chain, aminocarbonylalkyl of 2–7 carbon atoms, alkylaminocarbonylalkyl of 3–13 carbon atoms, arylaminocarbonylalkyl having 1–6 carbon atoms in the alkyl chain, Het-aminocarbonylalkyl having 1–6 carbon atoms in the alkyl chain, aminosulfonylalkyl of 1–6 carbon atoms, alkylsulfonylalkyl of 2–12 carbon atoms, arylsulfonylalkyl having 1–6 carbon atoms in the alkyl chain, alkylaminosulfonylalkyl of 2–12 carbon atoms, arylaminosulfonylalkyl having 1–6 carbon atoms in the alkyl chain, Het-aminosulfonylalkyl having 1–6 carbon atoms in the alkyl chain, phosphonylalkyl of 1–6 carbon atoms, or phosphorylalkyl of 1–6 carbon atoms;

$R_3$, $R_5$, and $R_6$, are each, independently, hydrogen, trifluoromethyl, alkyl of 1–6 carbon atoms, alkenyl of 2–7 carbon atoms, alkynyl of 2–7 carbon atoms, cycloalkyl of 3–8 carbon atoms, aryl, Het, arylalkyl having 1–6 carbon atoms in the alkyl chain, Het-alkyl having 1–6 carbon atoms in the alkyl chain, halogen, cyano, nitro, hydroxy, alkoxy of 1–6 carbon atoms, aryloxy, arylalkyloxy having 1–6 carbon atoms in the alkyl chain, alkylthio 1–6 carbon atoms, arylthio, arylamino, Het-amino, arylalkylamino of 1–6 carbons in the alkyl chain, Het-alkylamino having 1–6 carbon atoms in the alkyl chain, hydroxyamino, —NHCOR$_7$, —NHSO$_2$R$_7$, —NHP(O)(R$_7$)$_2$, —COR$_8$, —SO$_2$R$_8$, —NR$_8$R$_8$, carboxy, alkylcarbonyl of 2–7 carbon atoms, formylalkyl of 2–7 carbon atoms, phosphoryl, alkoxycarbonylalkyl of 3–13 carbon atoms, carboxyalkyl of 2–7 carbon atoms, alkylcarbonylalkyl of 2–13 carbon atoms, arylcarbonylalkyl having 1–6 carbon atoms in the alkyl chain, Het-carbonylalkyl having 1–6 carbon atoms in the alkyl chain, aminocarbonylalkyl of 2–7 carbon atoms, alkylaminocarbonylalkyl of 3–13 carbon atoms, arylaminocarbonylalkyl having 1–6 carbon atoms in the alkyl chain, Het-aminocarbonylalkyl having 1–6 carbon atoms in the alkyl chain, aminosulfonylalkyl of 1–6 carbon atoms, alkylsulfonylalkyl of 2–12 carbon atoms, arylsulfonylalkyl having 1–6 carbon atoms in the alkyl chain, alkylaminosulfonylalkyl of 2–12 carbon atoms, arylaminosulfonylalkyl of 1–6 carbon atoms, Het-aminosulfonylalkyl of 1–6 carbon atoms, phosphonylalkyl of 1–6 carbon atoms, or phosphorylalkyl of 1–6 carbon atoms; or $R_5$ and $R_6$ may be alkylene groups that are taken together to form a 3–8 membered cycloalkyl ring when $R_5$ and $R_6$ are attached to a common carbon atom;

$R_7$ is hydrogen, trifluoromethyl, alkyl of 1–6 carbon atoms, cycloalkyl of 3–8 carbon atoms, alkenyl of 2–7 carbon atoms, alkynyl of 2–7 carbon atoms, aryl, alkoxy of 1–6 carbon atoms, —NR$_8$R$_9$, or —NR$_9$(CH$_2$)$_p$—R$_8$ $R_8$ is hydrogen, alkoxy of 1–6 carbon atoms, alkyl of 1–6 carbon atoms, hydroxy, aryl substituted with $R_5$ and $R_6$, arylalkoxy having 1–6 carbon atoms in the alkyl chain, —CR$_3$R$_5$R$_6$, —(CH$_2$)$_p$—COR$_9$, or —(CH$_2$)$_p$—R$_9$;

$R_9$ is hydrogen, hydroxy, alkyl of 1–6 carbon atoms, cycloalkyl of 3–8 carbon atoms, alkoxy of 1–6 carbon atoms, aryl substituted with $R_5$ and $R_6$, Het substituted with $R_5$ and $R_6$, arylalkoxy having 1–6 carbon atoms in the alkyl chain, or —NR$_{10}$R$_{10}$;

$R_{10}$ is hydrogen, alkyl of 1–6 carbon atoms, alkoxycarbonyl of 2–7 carbon atoms, hydroxy, aryl substituted with $R_5$ and $R_6$, or Het substituted with $R_5$ and $R_6$;

Het is a monocyclic or bicyclic heterocycle of 5–10 ring atoms, having 1–4 heteroatoms selected from oxygen, nitrogen, and sulfur; wherein the heterocycle may be saturated, unsaturated, or partially unsaturated; and may be optionally fused to a phenyl ring;

m is 1–3;

n is 1–3;

and m+n=4;

p is 0–6;

or a pharmaceutically acceptable salt thereof.

2. The compound according to claim 1, wherein $R_2$ is hydrogen;

$R_4$ is alkyl of 1–6 carbon atoms, alkenyl of 2–7 carbon atoms, alkynyl of 2–7 carbon atoms, cycloalkyl of 3–8 carbon atoms, aryl substituted with $R_4$ and $R_5$, Het substituted with $R_5$ and $R_6$, —NR$_8$R$_8$, or —CR$_3$R$_5$R$_6$;

$R_3$, $R_5$, and $R_6$ are each, independently, hydrogen, alkyl of 1–6 carbon atoms, alkenyl for 2–7 carbon atoms, alkynyl of 2–7 carbon atoms, halogen, hydroxy, alkoxy of 1–6 carbon atoms, arylalkoxy having 1–6 carbon atoms in the alkyl chain, hydroxy, arylalkyl having 1–6 carbon atoms in the alkyl chain, Het-alkyl having 1–6 carbon atoms in the alkyl chain, —NHCOR$_7$, —NHSO$_2$R$_7$, —NR$_8$R$_8$, —COR$_8$, formylalkyl of 2–7 carbon atoms, or alkoxycarbonylalkyl of 3–13 carbon atoms, or $R_5$ and $R_6$ may be alkylene groups that are taken together to form a 3–8 membered cycloalkyl ring when $R_5$ and $R_6$ are attached to a common carbon atom;

Het is (a) a 6-membered saturated, partially unsaturated, or unsaturated heterocycle containing 1–2 nitrogens, optionally fused to a phenyl ring; (b) a 5-membered saturated, partially saturated, or unsaturated heterocycle containing 1–3 nitrogen, oxygen, or sulfur atoms, optionally fused to a phenyl ring; (c) a saturated, partially unsaturated, or unsaturated bicyclic heterocycle containing 1–4 nitrogen, oxygen, or sulfur atoms; (d) carbazole, dibenzofuran, and dibenzothiophene; wherein one or more of the ring carbon atoms of Het as described in (a), (b), or (c) may be a carbonyl moiety, where the ring does not contain a double bond in the position corresponding to that carbon atom;
or a pharmaceutically acceptable salt thereof.

3. The compound of claim 2, wherein

Y is $OCH_2$ or a bond;

$R_2$ is hydrogen;

$R_4$ is aryl substituted with $R_4$ and $R_5$, Het substituted with $R_5$ and $R_6$, $-NR_8R_8$, or $-CR_3R_5R_6$;

$R_3$, $R_5$, and $R_6$ are each, independently, hydrogen, alkyl of 1–6 carbon atoms, alkenyl of 2–7 carbon atoms, alkynyl of 2–7 carbon atoms, halogen, hydroxy, alkoxy of 1–6 carbon atoms, arylalkoxy having 1–6 carbon atoms in the alkyl chain, hydroxy, $-NHSO_2R_7$, $-NR_8R_8$, $-COR_8$, formylalkyl of 2–7 carbon atoms, or alkoxycarbonylalkyl of 3–13 carbon atoms, or $R_5$ and $R_6$ may be alkylene groups that are taken together to form a 3–8 membered cycloalkyl ring when $R_5$ and $R_6$ are attached to a common carbon atom;

Het is pyridine, pyrimidine, furan, imidazolyl, thiazole, oxazole, isoxazole, pyrazole, triazole, tetrazole, carbazole, pyrrole, thiophene, imidazole, imidazol-2-one, imidazole-2-thione, imidazolidine-2,4-dione, pyrazoline, triazole, tetrazole, oxazolone, oxadiazole, imidazolone, thiazole, thiazolone, thiadiazole, thiadiazolone, thiazoladine-2,4-dione, pyridine, pyrimidine, piperazine, pyrazine, pyrrolidine, piperidine, morpholine, benzofuran, dibenzofuran, dibenzothiophene, isobenzofuran, indole, isoindole, benzothiophene, 1,3,-dihydrobenzoimidazol-2-one, benzo[1,2,5]thiadoazole, 2-oxo-2,3-dihydro-1H-benzoimidazole, quinoline, or isoquinoline;
or a pharmaceutically acceptable salt thereof.

4. The compound of claim 1, which is a) N-Benzyl-N-(3,4-dimethoxy-phenyl)-4-{4-[2-hydroxy-3-(2-oxo-2,3-dihydro-1H-benzoimidazol-4-yloxy)-propylamino]-piperidin-1-yl}-benzenesulfonamide;

b) N-Benzyl-N-butyl-4-{4-[(2S)-2-hydroxy-3-(2-oxo-2,3-dihydro-1H-benzoimidazol-4-yloxy)-propylamino]-piperidin-1-yl}-benzenesulfonamide;

c) N-Benzyl-N-butyl-4-{4-[2-hydroxy-2-(4-hydroxy-3-methanesulfonylamino-phenyl)-ethylamino]-piperidin-1-yl)-benzenesulfonamide;

d) N-Benzyl-4-{4-[2-hydroxy-3-(2-oxo-2,3-dihydro-1H-benzoimidazol-4-yloxy)-propylamino]-piperidin-1-yl}-benzenesulfonamide;

e) N-Benzyl-4-{4-[2-hydroxy-2-(4-hydroxy-3-methanesulfonylamino-phenyl)-ethylamino]-piperidin-1-yl}-benzenesulfonamide;

f) N-Benzyl-4-{4-[(2S)-2-hydroxy-3-(4-hydroxyphenoxy)-propylamino]-piperidin-1-yl}-benzenesulfonamide;

g) N-(3,4-Dimethoxy-phenyl)-4-{4-[(2S)-2-hydroxy-3-(2-oxo-2,3-dihydro-1H-benzoimidazol-4-yloxy)-propylamino]-piperidin-1-yl}-benzenesulfonamide;

h) N-(3,4-Dimethoxy-phenyl)-4-{4-[2-hydroxy-2-(4-hydroxy-3-methanesulfonylamino-phenyl)-ethylamino]-piperidin-1-yl}-benzenesulfonamide;

i) 4-{4-[(2S)-3-(4-Benzyloxy-phenoxy)-2-hydroxy-propylamino]-piperidin-1-yl}-N-(3,4-dimethoxyphenyl)-benzenesulfonamide;

j) 4-{4-[(2S)-3-(9H-Carbazol-4-yloxy)-2-hydroxy-propylamino]-piperidin-1-yl)-N-(3,4-dimethoxyphenyl)-benzenesulfonamide;

k) N-(3,4-Dimethoxy-phenyl)-4-{4-[(2S)-2-hydroxy-3-(4-hydroxy-phenoxy)-propylamino]-piperidin-1-yl}-benzenesulfonamide;

l) N-Butyl-4-{4-[(2S)-2-hydroxy-3-(2-oxo-2,3-dihydro-1H-benzoimidazol-4-yloxy)-propylamino]-piperidin-1-yl}-benzenesulfonamide;

m) N-Butyl-4-{4-[(2S)-3-(9H-carbazol-4-yloxy)-2-hydroxy-propylamino]piperidin-1-yl}-benzenesulfonamide;

n) N-Butyl-4-{4-[(2R)-2-hydroxy-2-(4-hydroxy-3-methanesulfonylaminophenyl)-ethylamino]-piperidin-1-yl}-benzenesulfonamide;

o) 1-(4-{4-[2-Hydroxy-2-(4-hydroxy-3-methanesulfonylamino-phenyl)ethylamino]-piperidin-1-yl}-benzenesulfonyl)-pyrrolidine-2-carboxylic acid isopropyl ester;

p) 1-(4-{4-[2-Hydroxy-3-(2-oxo-2,3-dihydro-1H-benzoimidazol-4-yloxy)propylamino]-piperidin-1-yl}-benzenesulfonyl)-pyrrolidine-2-carboxylic acid isopropyl ester;

q) 1-(4-{4-[(2S)-2-Hydroxy-3-(2-oxo-2,3-dihydro-1H-benzoimidazol-4-yloxy)propylamino]-piperidin-1-yl}-benzenesulfonyl)-pyrrolidine-2-carboxylic acid methylamide;

r) 1-(4-{4-[2-Hydroxy-2-(4-hydroxy-3-methanesulfonylamino-phenyl)ethylamino]-piperidin-1-yl}-benzenesulfonyl)-pyrrolidine-2-carboxylic acid;

s) [Butyl-(4-{4-[(2R)-2-hydroxy-2-(4-hydroxy-3-methanesulfonylaminophenyl)-ethylamino]piperidin-1-yl}-benzenesulfonyl)-amino]-acetic acid benzyl ester;

t) [Butyl-(4-{4-[(2R)-2-hydroxy-2-(4-hydroxy-3-methanesulfonylaminophenyl)-ethylamino]-piperidin-1-yl}-benzenesulfonyl)-amino]-acetic acid;

u) (2R)-1-(4-{4-[(2R)-2-Hydroxy-2-(4-hydroxy-3-methanesulfonylamino-phenyl)ethylamino]-piperidin-1-yl}-benzenesulfonyl)-pyrrolidine-2-carboxylic acid benzyl ester;

v) (2S)-1-(4-{4-[(2R)-2-Hydroxy-2-(4-hydroxy-3-methanesulfonylamino-phenyl)ethylamino]-piperidin-1-yl}-benzenesulfonyl)-pyrrolidine-2-carboxylic acid benzyl ester;

w) [Butyl-(4-{4-[(2R)-2-hydroxy-2-(4-hydroxy-3-methanesulfonylamino-phenyl)-ethylamino]-piperidin-1-yl}-benzenesulfonyl)-amino]-acetic acid ethyl ester-1-yl}-phenyl)-amino]-acetic acid;

x) N-(2-Hydroxyethyl)-4-{4-[(2R)-2-hydroxy-2-(4-hydroxy-3-methanesulfonylamino-phenyl)-ethylamino]-piperidin-1-yl}-benzenesulfonamide;

y) [(4-{4-[(2R)-2-Hydroxy-2-(4-hydroxy-3-methanesulfonylamino-phenyl)-ethylamino]-piperidin-1-yl}-benzenesulfonyl)-methyl-amino]-acetic acid ethyl ester;

z) N-Cyclopropylmethyl-4-{4-[(2R)-2-hydroxy-2-(4-hydroxy-3-methanesulfonylamino-phenyl)-ethylamino)-piperidin-1-yl}-benzenesulfonamide;

aa) 4-{4-[(2R)-2-Hydroxy-2-(4-hydroxy-3-methanesulfonylamino-phenyl)-ethylamino]-piperidin-1-yl}-N-isobutyl-benzenesulfonamide;

bb) [Cyclopropylmethyl-(4-{4-[(2R)-2-hydroxy-2-(4-hydroxy-3-methanesulfonylamino-phenyl)- ethylamino]-piperidin-1-yl}-benzenesulfonyl)-amino]-acetic acid ethyl ester;

cc) 4-{4-[(2R)-2-Hydroxy-2-(4-hydroxy-3-methanesulfonylamino-phenyl)-ethylamino]-piperidin-1-yl}-N-isopropyl-benzenesulfonamide;

dd) 1-(4-{4-[(2R)-2-Hydroxy-2-(4-hydroxy-3-methanesulfonylamino-phenyl)-ethylamino]-piperidin-1-yl}-benzenesulfonyl)-pyrrolidine-(2R)-2-carboxylic acid ethyl ester;

ee) [Cyclopropylmethyl-(4-{4-[(2R)-2-hydroxy-2-(4-hydroxy-3-methanesulfonylamino-phenyl)-ethylamino]-piperidin-1-yl}-benzenesulfonyl)-amino]-acetic acid;

ff) [(4-{4-[(2R)-2-Hydroxy-2-(4-hydroxy-3-methanesulfonylamino-phenyl)-ethylamino]-piperidin-1-yl}-benzenesulfonyl)-isobutyl-amino]-acetic acid ethyl ester;

gg) [(4-[4-[(2R)-2-Hydroxy-2-(4-hydroxy-3-methanesulfonylamino-phenyl)-ethylamino]-piperidin-1-yl}-benzenesulfonyl)-methyl-amino]-acetic acid;

hh) [(4-{4-[(2R)-2-Hydroxy-2-(4-hydroxy-3-methanesulfonylamino-phenyl)-ethylamino]-piperidin-1-yl}-benzenesulfonyl)-isobutyl-amino]-acetic acid;

ii) 1-(4-{4-[(2R)-2-Hydroxy-2-(4-hydroxy-3-methanesulfonylamino-phenyl)-ethylamino]-piperidin-1-yl}-benzenesulfonyl)-pyrrolidine-(2R)-2-carboxylic acid;

jj) ethyl (2S)-1-[(4-{4-[((2R)-2-hydroxy-2-{4-hydroxy-3-[(methylsulfonyl)amino]phenyl}ethyl)amino]-1-piperidinyl}phenyl)sulfonyl]-2-pyrrolidinecarboxylate;

kk) ethyl (2S)-2-{[(4-{4-[((2R)-2-hydroxy-2-{4-hydroxy-3-[(methylsulfonyl)amino]phenyl}ethyl)amino]-1-piperidinyl}phenyl)sulfonyl]amino}-4-methylpentanoate;

ll) ethyl (2S)-2-{([(4-(4-[((2R)-2-hydroxy-2-(4-hydroxy-3-[(methylsulfonyl)amino]phenyl}ethyl)amino]-1-piperidinyl}phenyl)sulfonyl]amino}-3-methylbutanoate;

mm) (2S)-1-[(4-{4-[((2R)-2-hydroxy-2-{4-hydroxy-3-[(methylsulfonyl)amino]phenyl}ethyl)amino]-1-piperidinyl}phenyl)sulfonyl]-2-pyrrolidinecarboxylic acid;

nn) 1-(4-[4-[2-Hydroxy-2-(4-hydroxy-3-methanesulfonylmethyl-phenyl)-ethylamino]-piperidin-1-yl]-benzenesulfonylamino)-cyclopentanecarboxylic acid ethyl ester;

oo) N-{2-hydroxy-5-[(1R)-1-hydroxy-2-({1-[4-(1-pyrrolidinylsulfonyl)phenyl]-4-lidinylsulfonyl)phenyl]-4-piperidinyl}amino)ethyl]phenyl}methanesulfonamide;

pp) N-{2-hydroxy-5-[(1R)-1-hydroxy-2-({1-[4-(1-piperidinylsulfonyl)phenyl]-4-idinylsulfonyl)phenyl]-4-piperidinyl}amino)ethyl]phenyl}methanesulfonamide;

qq) 1-(4-{4-[2-Hydroxy-2-(4-hydroxy-3-methanesulfonyl methyl-phenyl)-ethylamino]-piperidin-1-yl}-benzenesulfonylamino)-cyclohexane carboxylic acid ethyl ester;

rr) 1-(4-{4-[2-Hydroxy-2-(4-hydroxy-3-methanesulfonyl methyl-phenyl)-ethylamino]-piperidin-1-yl}-benzenesulfonyl)-isopropyl-amino]acetic acid ethyl ester;

ss) N-[2-Hydroxy-5-(1-hydroxy-2-{1-[4-(toluene-4-sulfonyl)-phenyl]-piperidin-4-ylamino}-ethyl)-phenyl]-methanesulfonamide;

tt) 4-((2S)-2-Hydroxy-3-{1-[4-(toluene-4-sulfonyl)-phenyl]-piperidin-4-ylamino}-propoxy)-1,3-dihydro-benzoimidazol-2-one;

uu) 2-(2-butynyl)-2-[(4-{4-[((2R)-2-hydroxy-2-{4-hydroxy-3-[(methylsulfonyl)amino]-phenyl}ethyl)amino]-1-piperidinyl}phenyl)sulfonyl]-4-hexynoicacid tert-butyl ester;

vv) 2-(2-butynyl)-2-[(4-{4-[((2R)-2-hydroxy-2-{4-hydroxy-3-[(methylsulfonyl)amino}-phenyl}ethyl)amino]-1-piperidinyl}phenyl)sulfonyl]-4-hexynoic acid;

ww) 1-(4-{4-[(2S)-2-Hydroxy-3-(2-oxo-2,3-dihydro-1H-benzoimidazol-4-yloxy)propylamino]-piperidin-1-yl}-benzenesulfonyl)-imidazolidine-2,4-dione;

xx) N-[5-((1R)-2-{1-[4-(2,4-Dioxo-imidazolidine-1-sulfonyl)-phenyl]piperidin-4-ylamino}-1hydroxy-ethyl)-2-hydroxy-phenyl]-methanesulfonamide;

yy) 1-(4-{4-[((2S)-2-Hydroxy-2-(2-trifluoromethyl-thiazol-4-yl)-ethylamino]-piperidin-1-yl}-benzenesulfonyl)-imidazolidine-2,4-dione;

zz) tert-Butyl 2-{[(4-{4-[((2R)-2-hydroxy-2-{4-hydroxy-3-[(methylsulfonyl)amino]phenyl}ethyl)amino]-1-piperidinyl}phenyl)sulfonyl]amino}acetate;

aaa) 2-{[(4-{4-[((2R)-2-hydroxy-2-{4-hydroxy-3-[(methylsulfonyl)amino]phenyl}ethyl)amino]-1-piperidinyl}phenyl)sulfonyl]amino}acetic acid;

bbb) tert-Butyl 2-{[2-(tert-butoxy)-2-oxoethyl][(4-{4-[((2R)-2-hydroxy-2-{4-hydroxy-3-[(methylsulfonyl)amino]phenyl}ethyl)amino]-1-piperidinyl}phenyl)sulfonyl]amino}acetate;

ccc) 2-((Carboxymethyl)[(4-{4-[((2R)-2-hydroxy-2-{4-hydroxy-3-[(methylsulfonyl)amino]phenyl}ethyl)amino]-1-piperidinyl}phenyl)sulfonyl]amino}acetic acid;

ddd) Ethyl 2-{[(4-{4-[((2R)-2-hydroxy-2-{4-hydroxy-3-[(methylsulfonyl)amino]phenyl}ethyl)amino]-1-piperidinyl}phenyl)sulfonyl]amino}acetate;

eee) Methyl 2-{[(4-{4-[((2R)-2-hydroxy-2-{4-hydroxy-3-[(methylsulfonyl)amino]phenyl}ethyl)amino]-1-piperidinyl}phenyl)sulfonyl]amino}acetate;

fff) Ethyl 2-{[(4-{4-[((2R)-2-hydroxy-2-{4-hydroxy-3-[(methylsulfonyl)amino]phenyl}ethyl)amino]piperidin-1-yl}phenyl)sulfonyl]amino}acetylcarbamate;

ggg) tert-Butyl [[(4-{4-[((2R)-2-hydroxy-2-{4-hydroxy-3-[(methylsulfonyl)amino]phenyl}ethyl)amino]piperidin-1-yl}phenyl)sulfonyl](methoxycarbonyl)amino]acetate;

hhh) [[(4-{4-[((2R)-2-Hydroxy-2-{4-hydroxy-3-[(methylsulfonyl)amino]phenyl}ethyl)amino]piperidin-1-yl}phenyl)sulfonyl](methoxycarbonyl)amino]acetic acid;

iii) Ethyl {(2,5-difluorobenzyl)[(4-{4-[((2R)-2-hydroxy-2-{4-hydroxy-3-[(methylsulfonyl)amino]phenyl}ethyl)amino]piperidin-1-yl}phenyl)sulfonyl]amino}acetate;

jjj) 1-[4-({[(Butylamino)carbonyl]amino}sulfonyl)phenyl]-4-[((2R)-2-hydroxy-2-{4-hydroxy-3-[(methylsulfonyl)amino]phenyl}ethyl)amino]piperidine;

kkk) 2-{(2,5-Difluorobenzyl)[(4-{4-[((2R)-2-hydroxy-2-{4-hydroxy-3-[(methylsulfonyl)amino]phenyl}ethyl)amino]-1-piperidinyl}phenyl)sulfonyl]amino}acetic acid;

lll) Ethyl {4-[(4-{4-[((2R)-2-hydroxy-2-{4-hydroxy-3-[(methylsulfonyl)amino]phenyl}ethyl)amino]piperidin-1-yl}phenyl)sulfonyl]piperazin-1-yl}acetate;

mmm) {4-[(4-{4-[((2R)-2-hydroxy-2-{4-hydroxy-3-[(methylsulfonyl)amino]-phenyl}ethyl)amino]piperidin-1-yl}phenyl)sulfonyl]piperazin-1-yl}acetic acid;

nnn) N-(2-Hydroxy-5-{(1R)-1-hydroxy-2-[(1-{4-[(4-methylpiperazin-1-yl)sulfonyl]phenyl}piperidin-4-yl)amino]ethyl}phenyl)methanesulfonamide; or ooo) tert-Butyl {(2,5-difluorobenzyl)[(4-{4-[((2R)-2-hydroxy-2-{4-hydroxy-3-[(methylsulfonyl)amino]phenyl}ethyl)amino]piperidin-1-yl}phenyl)sulfonyl]amino}acetate;

or a pharmaceutically acceptable salt thereof; or

{4-[(4-{4-[((2R)-2-hydroxy-2-{4-hydroxy-3-[(methylsulfonyl)amino]-phenyl}ethyl)amino]piperidin-1-yl}phenyl)sulfonyl]piperazin-1-yl}acetic acid, sodium salt.

5. A method of treating metabolic disorders mediated by insulin resistance or hyperglycemia resulting from insulin resistance in a mammal in need thereof which comprises providing to said mammal, an effective amount of a compound of formula I having the structure

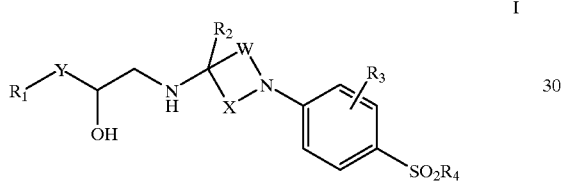

I wherein:

W is $(CH_2)_m$;

X is $(CH_2)_n$;

Y is $OCH_2$, $SCH_2$, or a bond;

$R_1$ is phenyl substituted with $R_5$ and $R_6$, or Het substituted with $R_5$ and $R_6$;

$R_2$ is hydrogen, trifluoromethyl, alkyl of 1–6 carbon atoms, alkenyl of 2–7 carbon atoms, or alkynyl of 2–7 carbon atoms;

$R_4$ is alkyl of 1–6 carbon atoms, alkenyl of 2–7 carbon atoms, alkynyl of 2–7 carbon atoms, cycloalkyl of 3–8 carbon atoms, hydroxy, aryl substituted with $R_5$ and $R_6$, Het substituted with $R_5$ and $R_6$, aryloxy, —$NHCOR_7$, —$NR_8R_8$, —$CR_3R_5R_6$, arylamino, Het-amino, arylalkylamino having 1–6 carbon atoms in the alkyl chain, Het-alkylamino having 1–6 carbon atoms in the alkyl chain, alkoxycarbonylalkyl of 3–13 carbon atoms, carboxyalkyl of 2–7 carbon atoms, alkylcarbonylalkyl of 3–13 carbon atoms, arylcarbonylalkyl having 1–6 carbon atoms in the alkyl chain, Het-carbonylalkyl having 1–6 carbon atoms in the alkyl chain, aminocarbonylalkyl of 2–7 carbon atoms, alkylaminocarbonylalkyl of 3–13 carbon atoms, arylaminocarbonylalkyl having 1–6 carbon atoms in the alkyl chain, Het-aminocarbonylalkyl having 1–6 carbon atoms in the alkyl chain, aminosulfonylalkyl of 1–6 carbon atoms, alkylsulfonylalkyl of 2–12 carbon atoms, arylsulfonylalkyl having 1–6 carbon atoms in the alkyl chain, alkylaminosulfonylalkyl of 2–12 carbon atoms, arylaminosulfonylalkyl having 1–6 carbon atoms in the alkyl chain, Het-aminosulfonylalkyl having 1–6 carbon atoms in the alkyl chain, phosphonylalkyl of 1–6 carbon atoms, or phosphorylalkyl of 1–6 carbon atoms;

$R_3$, $R_5$, and $R_6$, are each, independently, hydrogen, trifluoromethyl, alkyl of 1–6 carbon atoms, alkenyl of 2–7 carbon atoms, alkynyl of 2–7 carbon atoms, cycloalkyl of 3–8 carbon atoms, aryl, Het, arylalkyl having 1–6 carbon atoms in the alkyl chain, Het-alkyl having 1–6 carbon atoms in the alkyl chain, halogen, cyano, nitro, hydroxy, alkoxy of 1–6 carbon atoms, aryloxy, arylalkyloxy having 1–6 carbon atoms in the alkyl chain, alkylthio 1–6 carbon atoms, arylthio, arylamino, Het-amino, arylalkylamino of 1–6 carbons in the alkyl chain, Het-alkylamino having 1–6 carbon atoms in the alkyl chain, hydroxyamino, —$NHCOR_7$, —$NHSO_2R_7$, —$NHP(O)(R_7)_2$, —$COR_8$, —$SO_2R_8$, —$NR_8R_8$, carboxy, alkylcarbonyl of 2–7 carbon atoms, formylalkyl of 2–7 carbon atoms, phosphoryl, alkoxycarbonylalkyl of 3–13 carbon atoms, carboxyalkyl of 2–7 carbon atoms, alkylcarbonylalkyl of 2–13 carbon atoms, arylcarbonylalkyl having 1–6 carbon atoms in the alkyl chain, Het-carbonylalkyl having 1–6 carbon atoms in the alkyl chain, aminocarbonylalkyl of 2–7 carbon atoms, alkylaminocarbonylalkyl of 3–13 carbon atoms, arylaminocarbonylalkyl having 1–6 carbon atoms in the alkyl chain, Het-aminocarbonylalkyl having 1–6 carbon atoms in the alkyl chain, aminosulfonylalkyl of 1–6 carbon atoms, alkylsulfonylalkyl of 2–12 carbon atoms, arylsulfonylalkyl having 1–6 carbon atoms in the alkyl chain, alkylaminosulfonylalkyl of 2–12 carbon atoms, arylaminosulfonylalkyl of 1–6 carbon atoms, Het-aminosulfonylalkyl of 1–6 carbon atoms, phosphonylalkyl of 1–6 carbon atoms, or phosphorylalkyl of 1–6 carbon atoms; or $R_5$ and $R_6$ may be alkylene groups that are taken together to form a 3–8 membered cycloalkyl ring when $R_5$ and $R_6$ are attached to a common carbon atom;

$R_7$ is hydrogen, trifluoromethyl, alkyl of 1–6 carbon atoms, cycloalkyl of 3–8 carbon atoms, alkenyl of 2–7 carbon atoms, alkynyl of 2–7 carbon atoms, aryl, alkoxy of 1–6 carbon atoms, —$NR_8R_9$, or —$NR_9(CH_2)_p$—$R_8$ $R_8$ is hydrogen, alkoxy of 1–6 carbon atoms, alkyl of 1–6 carbon atoms, hydroxy, aryl substituted with $R_5$ and $R_6$, arylalkoxy having 1–6 carbon atoms in the alkyl chain, —$CR_3R_5R_6$, —$(CH_2)_p$—$COR_9$, or —$(CH_2)_p$—$R_9$;

$R_9$ is hydrogen, hydroxy, alkyl of 1–6 carbon atoms, cycloalkyl of 3–8 carbon atoms, alkoxy of 1–6 carbon atoms, aryl substituted with $R_5$ and $R_6$, Het substituted with $R_5$ and $R_6$, arylalkoxy having 1–6 carbon atoms in the alkyl chain, or —$NR_{10}R_{10}$;

$R_{10}$ is hydrogen, alkyl of 1–6 carbon atoms, alkoxycarbonyl of 2–7 carbon atoms, hydroxy, aryl substituted with $R_5$ and $R_6$, or Het substituted with $R_5$ and $R_6$; Het is a monocyclic or bicyclic heterocycle of 5–10 ring atoms, having 1–4 heteroatoms selected from oxygen, nitrogen, and sulfur; wherein the heterocycle may be saturated, unsaturated, or partially unsaturated; and may be optionally fused to a phenyl ring;

m is 1–3;

n is 1–3;

and m+n=4;

p is 0–6;

or a pharmaceutically acceptable salt thereof.

6. A method of treating or inhibiting type II diabetes in a mammal in need thereof which comprises providing to said mammal, an effective amount of a compound of Formula I having the structure

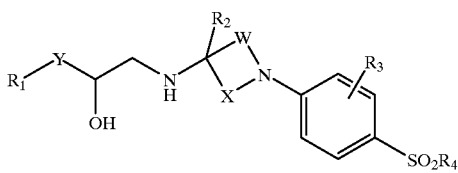

wherein:
W is $(CH_2)_m$;
X is $(CH_2)_n$;
Y is $OCH_2$, $SCH_2$, or a bond;
$R_1$ is phenyl substituted with $R_5$ and $R_6$, or Het substituted with $R_5$ and $R_6$;
$R_2$ is hydrogen, trifluoromethyl, alkyl of 1–6 carbon atoms, alkenyl of 2–7 carbon atoms, or alkynyl of 2–7 carbon atoms;
$R_4$ is alkyl of 1–6 carbon atoms, alkenyl of 2–7 carbon atoms, alkynyl of 2–7 carbon atoms, cycloalkyl of 3–8 carbon atoms, hydroxy, aryl substituted with $R_5$ and $R_6$, Het substituted with $R_5$ and $R_6$, aryloxy, —NHCOR$_7$, —NR$_8$R$_8$, —CR$_3$R$_5$R$_6$, arylamino, Het-amino, arylalkylamino having 1–6 carbon atoms in the alkyl chain, Het-alkylamino having 1–6 carbon atoms in the alkyl chain, alkoxycarbonylalkyl of 3–13 carbon atoms, carboxyalkyl of 2–7 carbon atoms, alkylcarbonylalkyl of 3–13 carbon atoms, arylcarbonylalkyl having 1–6 carbon atoms in the alkyl chain, Het-carbonylalkyl having 1–6 carbon atoms in the alkyl chain, aminocarbonylalkyl of 2–7 carbon atoms, alkylaminocarbonylalkyl of 3–13 carbon atoms, arylaminocarbonylalkyl having 1–6 carbon atoms in the alkyl chain, Het-aminocarbonylalkyl having 1–6 carbon atoms in the alkyl chain, aminosulfonylalkyl of 1–6 carbon atoms, alkylsulfonylalkyl of 2–12 carbon atoms, arylsulfonylalkyl having 1–6 carbon atoms in the alkyl chain, alkylaminosulfonylalkyl of 2–12 carbon atoms, arylaminosulfonylalkyl having 1–6 carbon atoms in the alkyl chain, Het-aminosulfonylalkyl having 1–6 carbon atoms in the alkyl chain, phosphonylalkyl of 1–6 carbon atoms, or phosphorylalkyl of 1–6 carbon atoms;
$R_3$, $R_5$, and $R_6$, are each, independently, hydrogen, trifluoromethyl, alkyl of 1–6 carbon atoms, alkenyl of 2–7 carbon atoms, alkynyl of 2–7 carbon atoms, cycloalkyl of 3–8 carbon atoms, aryl, Het, arylalkyl having 1–6 carbon atoms in the alkyl chain, Het-alkyl having 1–6 carbon atoms in the alkyl chain, halogen, cyano, nitro, hydroxy, alkoxy of 1–6 carbon atoms, aryloxy, arylalkyloxy having 1–6 carbon atoms in the alkyl chain, alkylthio 1–6 carbon atoms, arylthio, arylamino, Het-amino, arylalkylamino of 1–6 carbons in the alkyl chain, Het-alkylamino having 1–6 carbon atoms in the alkyl chain, hydroxyamino, —NHCOR$_7$, —NHSO$_2$R$_7$, —NHP(O)(R$_7$)$_2$, —COR$_8$, —SO$_2$R$_8$, —NR$_8$R$_8$, carboxy, alkylcarbonyl of 2–7 carbon atoms, formylalkyl of 2–7 carbon atoms, phosphoryl, alkoxycarbonylalkyl of 3–13 carbon atoms, carboxyalkyl of 2–7 carbon atoms, alkylcarbonylalkyl of 2–13 carbon atoms, arylcarbonylalkyl having 1–6 carbon atoms in the alkyl chain, Het-carbonylalkyl having 1–6 carbon atoms in the alkyl chain, aminocarbonylalkyl of 2–7 carbon atoms, alkylaminocarbonylalkyl of 3–13 carbon atoms, arylaminocarbonylalkyl having 1–6 carbon atoms in the alkyl chain, Het-aminocarbonylalkyl having 1–6 carbon atoms in the alkyl chain, aminosulfonylalkyl of 1–6 carbon atoms, alkylsulfonylalkyl of 2–12 carbon atoms, arylsulfonylalkyl having 1–6 carbon atoms in the alkyl chain, alkylaminosulfonylalkyl of 2–12 carbon atoms, arylaminosulfonylalkyl of 1–6 carbon atoms, Het-aminosulfonylalkyl of 1–6 carbon atoms, phosphonylalkyl of 1–6 carbon atoms, or phosphorylalkyl of 1–6 carbon atoms; or $R_5$ and $R_6$ may be alkylene groups that are taken together to form a 3–8 membered cycloalkyl ring when $R_5$ and $R_6$ are attached to a common carbon atom;
$R_7$ is hydrogen, trifluoromethyl, alkyl of 1–6 carbon atoms, cycloalkyl of 3–8 carbon atoms, alkenyl of 2–7 carbon atoms, alkynyl of 2–7 carbon atoms, aryl, alkoxy of 1–6 carbon atoms, —NR$_8$R$_9$, or —NR$_9$(CH$_2$)$_p$—R$_8$
$R_8$ is hydrogen, alkoxy of 1–6 carbon atoms, alkyl of 1–6 carbon atoms, hydroxy, aryl substituted with $R_5$ and $R_6$, arylalkoxy having 1–6 carbon atoms in the alkyl chain, —CR$_3$R$_5$R$_6$, —(CH$_2$)$_p$—COR$_9$, or —(CH$_2$)$_p$—R$_9$;
$R_9$ is hydrogen, hydroxy, alkyl of 1–6 carbon atoms, cycloalkyl of 3–8 carbon atoms, alkoxy of 1–6 carbon atoms, aryl substituted with $R_5$ and $R_6$, Het substituted with $R_5$ and $R_6$, arylalkoxy having 1–6 carbon atoms in the alkyl chain, or —NR$_{10}$R$_{10}$;
$R_{10}$ is hydrogen, alkyl of 1–6 carbon atoms, alkoxycarbonyl of 2–7 carbon atoms, hydroxy, aryl substituted with $R_5$ and $R_6$, or Het substituted with $R_5$ and $R_6$; Het is a monocyclic or bicyclic heterocycle of 5–10 ring atoms, having 1–4 heteroatoms selected from oxygen, nitrogen, and sulfur; wherein the heterocycle may be saturated, unsaturated, or partially unsaturated; and may be optionally fused to a phenyl ring;
m is 1–3;
n is 1–3;
and m+n=4;
p is 0–6;
or a pharmaceutically acceptable salt thereof.

7. A method of modulating glucose levels in a mammal in need thereof which comprises providing to said mammal, an effective amount of a compound of formula I having the structure

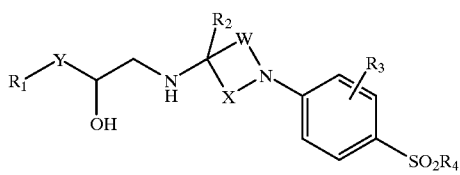

wherein:
W is $(CH_2)_m$;
X is $(CH_2)_n$;
Y is $OCH_2$, $SCH_2$, or a bond;
$R_1$ is phenyl substituted with $R_5$ and $R_6$, or Het substituted with $R_5$ and $R_6$;
$R_2$ is hydrogen, trifluoromethyl, alkyl of 1–6 carbon atoms, alkenyl of 2–7 carbon atoms, or alkynyl of 2–7 carbon atoms;
$R_4$ is alkyl of 1–6 carbon atoms, alkenyl of 2–7 carbon atoms, alkynyl of 2–7 carbon atoms, cycloalkyl of 3–8 carbon atoms, hydroxy, aryl substituted with $R_5$ and $R_6$, Het substituted with $R_5$ and $R_6$, aryloxy, —NHCOR$_7$, —NR$_8$R$_8$, —CR$_3$R$_5$R$_6$, arylamino, Het-amino, arylalkylamino having 1–6 carbon atoms in the alkyl chain, Het-alkylamino having 1–6 carbon atoms in the alkyl chain, alkoxycarbonylalkyl of 3–13 carbon atoms, carboxyalkyl of 2–7 carbon atoms, alkylcarbonylalkyl of 3–13 carbon atoms, arylcarbonylalkyl having 1–6 carbon atoms in the alkyl chain, Het-carbonylalkyl having 1–6 carbon atoms in the alkyl chain, aminocarbonylalkyl of 2–7 carbon atoms, alkylaminocarbonylalkyl of 3–13 carbon atoms, arylaminocarbonylalkyl having 1–6 carbon atoms in the alkyl chain, Het-aminocarbonylalkyl having 1–6 carbon atoms in the alkyl chain, aminosulfonylalkyl of 1–6 carbon atoms, alkylsulfonylalkyl of 2–12 carbon atoms, arylsulfonylalkyl having 1–6 carbon atoms in the alkyl chain, alkylaminosulfonylalkyl of 2–12 carbon atoms, arylaminosulfonylalkyl having 1–6 carbon atoms in the alkyl chain, Het-aminosulfonylalkyl having 1–6 carbon atoms in the alkyl chain, phosphonylalkyl of 1–6 carbon atoms, or phosphorylalkyl of 1–6 carbon atoms;

$R_3$, $R_5$, and $R_6$, are each, independently, hydrogen, trifluoromethyl, alkyl of 1–6 carbon atoms, alkenyl of 2–7 carbon atoms, alkynyl of 2–7 carbon atoms, cycloalkyl of 3–8 carbon atoms, aryl, Het, arylalkyl having 1–6 carbon atoms in the alkyl chain, Het-alkyl having 1–6 carbon atoms in the alkyl chain, halogen, cyano, nitro, hydroxy, alkoxy of 1–6 carbon atoms, aryloxy, arylalkyloxy having 1–6 carbon atoms in the alkyl chain, alkylthio 1–6 carbon atoms, arylthio, arylamino, Het-amino, arylalkylamino of 1–6 carbons in the alkyl chain, Het-alkylamino having 1–6 carbon atoms in the alkyl chain, hydroxyamino, —NHCOR$_7$, —NHSO$_2$R$_7$, —NH P(O)(R$_7$)$_2$, —COR$_8$, —SO$_2$R$_8$, —NR$_8$R$_8$, carboxy, alkylcarbonyl of 2–7 carbon atoms, formylalkyl of 2–7 carbon atoms, phosphoryl, alkoxycarbonylalkyl of 3–13 carbon atoms, carboxyalkyl of 2–7 carbon atoms, alkylcarbonylalkyl of 2–13 carbon atoms, arylcarbonylalkyl having 1–6 carbon atoms in the alkyl chain, Het-carbonylalkyl having 1–6 carbon atoms in the alkyl chain, aminocarbonylalkyl of 2–7 carbon atoms, alkylaminocarbonylalkyl of 3–13 carbon atoms, arylaminocarbonylalkyl having 1–6 carbon atoms in the alkyl chain, Het-aminocarbonylalkyl having 1–6 carbon atoms in the alkyl chain, aminosulfonylalkyl of 1–6 carbon atoms, alkylsulfonylalkyl of 2–12 carbon atoms, arylsulfonylalkyl having 1–6 carbon atoms in the alkyl chain, alkylaminosulfonylalkyl of 2–12 carbon atoms, arylaminosulfonylalkyl of 1–6 carbon atoms, Het-aminosulfonylalkyl of 1–6 carbon atoms, phosphonylalkyl of 1–6 carbon atoms, or phosphorylalkyl of 1–6 carbon atoms; or $R_5$ and $R_6$ may be alkylene groups that are taken together to form a 3–8 membered cycloalkyl ring when $R_5$ and $R_6$ are attached to a common carbon atom;

$R_7$ is hydrogen, trifluoromethyl, alkyl of 1–6 carbon atoms, cycloalkyl of 3–8 carbon atoms, alkenyl of 2–7 carbon atoms, alkynyl of 2–7 carbon atoms, aryl, alkoxy of 1–6 carbon atoms, —NR$_8$R$_9$, or —NR$_9$(CH$_2$)$_p$—R$_8$ $R_8$ is hydrogen, alkoxy of 1–6 carbon atoms, alkyl of 1–6 carbon atoms, hydroxy, aryl substituted with $R_5$ and $R_6$, arylalkoxy having 1–6 carbon atoms in the alkyl chain, —CR$_3$R$_5$R$_6$, —(CH$_2$)$_p$—COR$_9$, or —(CH$_2$)$_p$—R$_9$;

$R_9$ is hydrogen, hydroxy, alkyl of 1–6 carbon atoms, cycloalkyl of 3–8 carbon atoms, alkoxy of 1–6 carbon atoms, aryl substituted with $R_5$ and $R_6$, Het substituted with $R_5$ and $R_6$, arylalkoxy having 1–6 carbon atoms in the alkyl chain, or —NR$_{10}$R$_{10}$;

$R_{10}$ is hydrogen, alkyl of 1–6 carbon atoms, alkoxycarbonyl of 2–7 carbon atoms, hydroxy, aryl substituted with $R_5$ and $R_6$, or Het substituted with $R_5$ and $R_6$; Het is a monocyclic or bicyclic heterocycle of 5–10 ring atoms, having 1–4 heteroatoms selected from oxygen, nitrogen, and sulfur; wherein the heterocycle may be saturated, unsaturated, or partially unsaturated; and may be optionally fused to a phenyl ring;

m is 1–3;

n is 1–3;

and m+n=4;

p is 0–6;

or a pharmaceutically acceptable salt thereof.

8. A method of treating or inhibiting urinary incontinence in a mammal in need thereof which comprises providing to said mammal an effective amount of a compound of formula I having the structure

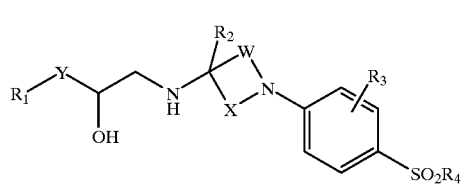

wherein:

W is (CH$_2$)$_m$;

X is (CH$_2$)$_n$;

Y is OCH$_2$, SCH$_2$, or a bond;

$R_1$ is phenyl substituted with $R_5$ and $R_6$, or Het substituted with $R_5$ and $R_6$;

$R_2$ is hydrogen, trifluoromethyl, alkyl of 1–6 carbon atoms, alkenyl of 2–7 carbon atoms, or alkynyl of 2–7 carbon atoms;

$R_4$ is alkyl of 1–6 carbon atoms, alkenyl of 2–7 carbon atoms, alkynyl of 2–7 carbon atoms, cycloalkyl of 3–8 carbon atoms, hydroxy, aryl substituted with $R_5$ and $R_6$, Het substituted with $R_5$ and $R_6$, aryloxy, —NHCOR$_7$, —NR$_8$R$_8$, —CR$_3$R$_5$R$_6$, arylamino, Het-amino, arylalkylamino having 1–6 carbon atoms in the alkyl chain, Het-alkylamino having 1–6 carbon atoms in the alkyl chain, alkoxycarbonylalkyl of 3–13 carbon atoms, carboxyalkyl of 2–7 carbon atoms, alkylcarbonylalkyl of 3–13 carbon atoms, arylcarbonylalkyl having 1–6 carbon atoms in the alkyl chain, Het-carbonylalkyl having 1–6 carbon atoms in the alkyl chain, aminocarbonylalkyl of 2–7 carbon atoms, alkylaminocarbonylalkyl of 3–13 carbon atoms, arylaminocarbonylalkyl having 1–6 carbon atoms in the alkyl chain, Het-aminocarbonylalkyl having 1–6 carbon atoms in the alkyl chain, aminosulfonylalkyl of 1–6 carbon atoms, alkylsulfonylalkyl of 2–12 carbon atoms, arylsulfonylalkyl having 1–6 carbon atoms in the alkyl chain, alkylaminosulfonylalkyl of 2–12 carbon atoms, arylaminosulfonylalkyl having 1–6 carbon atoms in the alkyl chain, Het-aminosulfonylalkyl having 1–6 carbon atoms in the alkyl chain, phosphonylalkyl of 1–6 carbon atoms, or phosphorylalkyl of 1–6 carbon atoms;

$R_3$, $R_5$, and $R_6$, are each, independently, hydrogen, trifluoromethyl, alkyl of 1–6 carbon atoms, alkenyl of 2–7 carbon atoms, alkynyl of 2–7 carbon atoms, cycloalkyl of 3–8 carbon atoms, aryl, Het, arylalkyl having 1–6 carbon atoms in the alkyl chain, Het-alkyl having 1–6 carbon atoms in the alkyl chain, halogen, cyano, nitro, hydroxy, alkoxy of 1–6 carbon atoms, aryloxy, arylalkyloxy having 1–6 carbon atoms in the alkyl chain, alkylthio 1–6 carbon atoms, arylthio, arylamino, Het-amino, arylalkylamino of 1–6 carbons in the alkyl chain, Het-alkylamino having 1–6 carbon atoms in the alkyl chain, hydroxyamino, —NHCOR$_7$, —NHSO$_2$R$_7$, —NHP(O)(R$_7$)$_2$, —COR$_8$, —SO$_2$R$_8$, —NR$_8$R$_8$, carboxy, alkylcarbonyl of 2–7 carbon atoms, formylalkyl of 2–7 carbon atoms, phosphoryl, alkoxycarbonylalkyl of 3–13 carbon atoms, carboxyalkyl of 2–7 carbon atoms, alkylcarbonylalkyl of 2–13 carbon atoms, arylcarbonylalkyl having 1–6 carbon atoms in the alkyl chain, Het-carbonylalkyl having 1–6 carbon atoms in the alkyl chain, aminocarbonylalkyl of 2–7 carbon atoms, alkylaminocarbonylalkyl of 3–13 carbon atoms, arylaminocarbonylalkyl having 1–6 carbon atoms in the alkyl chain, Het-aminocarbonylalkyl having 1–6 carbon atoms in the alkyl chain, aminosulfonylalkyl of 1–6 carbon atoms, alkylsulfonylalkyl of 2–12 carbon atoms, arylsulfonylalkyl having 1–6 carbon atoms in the alkyl chain, alkylaminosulfonylalkyl of 2–12 carbon atoms, arylaminosulfonylalkyl of 1–6 carbon atoms, Het-aminosulfonylalkyl of 1–6 carbon atoms, phosphonylalkyl of 1–6 carbon atoms, or phosphorylalkyl of 1–6 carbon atoms; or R$_5$ and R$_6$ may be alkylene groups that are taken together to form a 3–8 membered cycloalkyl ring when R$_5$ and R$_6$ are attached to a common carbon atom;

R$_7$ is hydrogen, trifluoromethyl, alkyl of 1–6 carbon atoms, cycloalkyl of 3–8 carbon atoms, alkenyl of 2–7 carbon atoms, alkynyl of 2–7 carbon atoms, aryl, alkoxy of 1–6 carbon atoms, —NR$_8$R$_9$, or —NH$_9$(CH$_2$)$_p$—R$_8$ R$_8$ is hydrogen, alkoxy of 1–6 carbon atoms, alkyl of 1–6 carbon atoms, hydroxy, aryl substituted with R$_5$ and R$_6$, arylalkoxy having 1–6 carbon atoms in the alkyl chain, —CR$_3$R$_5$R$_6$, —(CH$_2$)$_p$—COR$_9$, or —(CH$_2$)$_p$—R$_9$;

R$_9$ is hydrogen, hydroxy, alkyl of 1–6 carbon atoms, cycloalkyl of 3–8 carbon atoms, alkoxy of 1–6 carbon atoms, aryl substituted with R$_5$ and R$_6$, Het substituted with R$_5$ and R$_6$, arylalkoxy having 1–6 carbon atoms in the alkyl chain, or —NR$_{10}$R$_{10}$;

R$_{10}$ is hydrogen, alkyl of 1–6 carbon atoms, alkoxycarbonyl of 2–7 carbon atoms, hydroxy, aryl substituted with R$_5$ and R$_6$, or Het substituted with R$_5$ and R$_6$;

Het is a monocyclic or bicyclic heterocycle of 5–10 ring atoms, having 1–4 heteroatoms selected from oxygen, nitrogen, and sulfur; wherein the heterocycle may be saturated, unsaturated, or partially unsaturated; and may be optionally fused to a phenyl ring;

m is 1–3;

n is 1–3;

and m+n=4;

p is 0–6;

or a pharmaceutically acceptable salt thereof.

9. A method of treating or inhibiting atherosclerosis, gastrointestinal disorders, neurogenic inflammation, glaucoma, or ocular hypertension in a mammal in need thereof, which comprises providing to said mammal an effective amount of a compound of formula I having the structure

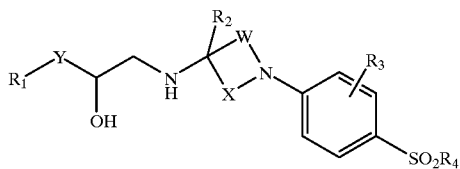

wherein:

W is (CH$_2$)$_m$;

X is (CH$_2$)$_n$;

Y is OCH$_2$, SCH$_2$, or a bond;

R$_1$ is phenyl substituted with R$_5$ and R$_6$, or Het substituted with R$_5$ and R$_6$; R$_2$ is hydrogen, trifluoromethyl, alkyl of 1–6 carbon atoms, alkenyl of 2–7 carbon atoms, or alkynyl of 2–7 carbon atoms;

R$_4$ is alkyl of 1–6 carbon atoms, alkenyl of 2–7 carbon atoms, alkynyl of 2–7 carbon atoms, cycloalkyl of 3–8 carbon atoms, hydroxy, aryl substituted with R$_5$ and R$_6$, Het substituted with R$_5$ and R$_6$, aryloxy, —NHCOR$_7$, —NR$_8$R$_8$, —CR$_3$R$_5$R$_6$, arylamino, Het-amino, arylalkylamino having 1–6 carbon atoms in the alkyl chain, Het-alkylamino having 1–6 carbon atoms in the alkyl chain, alkoxycarbonylalkyl of 3–13 carbon atoms, carboxyalkyl of 2–7 carbon atoms, alkylcarbonylalkyl of 3–13 carbon atoms, arylcarbonylalkyl having 1–6 carbon atoms in the alkyl chain, Het-carbonylalkyl having 1–6 carbon atoms in the alkyl chain, aminocarbonylalkyl of 2–7 carbon atoms, alkylaminocarbonylalkyl of 3–13 carbon atoms, arylaminocarbonylalkyl having 1–6 carbon atoms in the alkyl chain, Het-aminocarbonylalkyl having 1–6 carbon atoms in the alkyl chain, aminosulfonylalkyl of 1–6 carbon atoms, alkylsulfonylalkyl of 2–12 carbon atoms, arylsulfonylalkyl having 1–6 carbon atoms in the alkyl chain, alkylaminosulfonylalkyl of 2–12 carbon atoms, arylaminosulfonylalkyl having 1–6 carbon atoms in the alkyl chain, Het-aminosulfonylalkyl having 1–6 carbon atoms in the alkyl chain, phosphonylalkyl of 1–6 carbon atoms, or phosphorylalkyl of 1–6 carbon atoms;

R$_3$, R$_5$, and R$_6$, are each, independently, hydrogen, trifluoromethyl, alkyl of 1–6 carbon atoms, alkenyl of 2–7 carbon atoms, alkynyl of 2–7 carbon atoms, cycloalkyl of 3–8 carbon atoms, aryl, Het, arylalkyl having 1–6 carbon atoms in the alkyl chain, Het-alkyl having 1–6 carbon atoms in the alkyl chain, halogen, cyano, nitro, hydroxy, alkoxy of 1–6 carbon atoms, aryloxy, arylalkyloxy having 1–6 carbon atoms in the alkyl chain, alkylthio 1–6 carbon atoms, arylthio, arylamino, Het-amino, arylalkylamino of 1–6 carbons in the alkyl chain, Het-alkylamino having 1–6 carbon atoms in the alkyl chain, hydroxyamino, —NHCOR$_7$, —NHSO$_2$R$_7$, —NHP(O)(R$_7$)$_2$, —COR$_8$, —SO2 R$_8$, —NR$_8$R$_8$, carboxy, alkylcarbonyl of 2–7 carbon atoms, formylalkyl of 2–7 carbon atoms, phosphoryl, alkoxycarbonylalkyl of 3–13 carbon atoms, carboxyalkyl of 2–7 carbon atoms, alkylcarbonylalkyl of 2–13 carbon atoms, arylcarbonylalkyl having 1–6 carbon atoms in the alkyl chain, Het-carbonylalkyl having 1–6 carbon atoms in the alkyl chain, aminocarbonylalkyl of 2–7 carbon atoms, alkylaminocarbonylalkyl of 3–13 carbon atoms, arylaminocarbonylalkyl having 1–6 carbon atoms in the alkyl chain, Het-aminocarbonylalkyl having 1–6 carbon atoms in the alkyl chain, aminosulfonylalkyl of 1–6 carbon atoms, alkylsulfonylalkyl of 2–12 carbon atoms, arylsulfonylalkyl having 1–6 carbon atoms in the alkyl chain, alkylaminosulfonylalkyl of 2–12 carbon atoms, arylaminosulfonylalkyl of 1–6 carbon atoms, Het-aminosulfonylalkyl of 1–6 carbon atoms, phosphonylalkyl of 1–6 carbon atoms, or phosphorylalkyl of 1–6 carbon atoms; or $R_5$ and $R_6$ may be alkylene groups that are taken together to form a 3–8 membered cycloalkyl ring when $R_5$ and $R_6$ are attached to a common carbon atom;

$R_7$ is hydrogen, trifluoromethyl, alkyl of 1–6 carbon atoms, cycloalkyl of 3–8 carbon atoms, alkenyl of 2–7 carbon atoms, alkynyl of 2–7 carbon atoms, aryl, alkoxy of 1–6 carbon atoms, $-NR_8R_9$, or $-NR_9(CH_2)_p-R_8$ $R_8$ is hydrogen, alkoxy of 1–6 carbon atoms, alkyl of 1–6 carbon atoms, hydroxy, aryl substituted with $R_5$ and $R_6$, arylalkoxy having 1–6 carbon atoms in the alkyl chain, $-CR_3R_5R_6$, $-(CH_2)_p-COR_9$, or $-(CH_2)_p-R_9$;

$R_9$ is hydrogen, hydroxy, alkyl of 1–6 carbon atoms, cycloalkyl of 3–8 carbon atoms, alkoxy of 1–6 carbon atoms, aryl substituted with $R_5$ and $R_6$, Het substituted with $R_5$ and $R_6$, arylalkoxy having 1–6 carbon atoms in the alkyl chain, or $-NR_{10}R_{10}$;

$R_{10}$ is hydrogen, alkyl of 1–6 carbon atoms, alkoxycarbonyl of 2–7 carbon atoms, hydroxy, aryl substituted with $R_5$ and $R_6$, or Het substituted with $R_5$ and $R_6$;

Het is a monocyclic or bicyclic heterocycle of 5–10 ring atoms, having 1–4 heteroatoms selected from oxygen, nitrogen, and sulfur; wherein the heterocycle may be saturated, unsaturated, or partially unsaturated; and may be optionally fused to a phenyl ring;

m is 1–3;

n is 1–3;

and m+n=4;

p is 0–6;

or a pharmaceutically acceptable salt thereof.

10. A pharmaceutical composition which comprises a compound of formula I having the structure

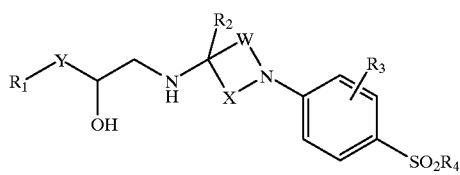

wherein:

W is $(CH_2)_m$;

X is $(CH_2)_n$;

Y is $OCH_2$, $SCH_2$, or a bond;

$R_1$ is phenyl substituted with $R_5$ and $R_6$, or Het substituted with $R_5$ and $R_6$; $R_2$ is hydrogen, trifluoromethyl, alkyl of 1–6 carbon atoms, alkenyl of 2–7 carbon atoms, or alkynyl of 2–7 carbon atoms;

$R_4$ is alkyl of 1–6 carbon atoms, alkenyl of 2–7 carbon atoms, alkynyl of 2–7 carbon atoms, cycloalkyl of 3–8 carbon atoms, hydroxy, aryl substituted with $R_5$ and $R_6$, Het substituted with $R_5$ and $R_6$, aryloxy, $-NHCOR_7$, $-NR_8R_8$, $-CR_3R_5R_6$, arylamino, Het-amino, arylalkylamino having 1–6 carbon atoms in the alkyl chain, Het-alkylamino having 1–6 carbon atoms in the alkyl chain, alkoxycarbonylalkyl of 3–13 carbon atoms, carboxyalkyl of 2–7 carbon atoms, alkylcarbonylalkyl of 3–13 carbon atoms, arylcarbonylalkyl having 1–6 carbon atoms in the alkyl chain, Het-carbonylalkyl having 1–6 carbon atoms in the alkyl chain, aminocarbonylalkyl of 2–7 carbon atoms, alkylaminocarbonylalkyl of 3–13 carbon atoms, arylaminocarbonylalkyl having 1–6 carbon atoms in the alkyl chain, Het-aminocarbonylalkyl having 1–6 carbon atoms in the alkyl chain, aminosulfonylalkyl of 1–6 carbon atoms, alkylsulfonylalkyl of 2–12 carbon atoms, arylsulfonylalkyl having 1–6 carbon atoms in the alkyl chain, alkylaminosulfonylalkyl of 2–12 carbon atoms, arylaminosulfonylalkyl having 1–6 carbon atoms in the alkyl chain, Het-aminosulfonylalkyl having 1–6 carbon atoms in the alkyl chain, phosphonylalkyl of 1–6 carbon atoms, or phosphorylalkyl of 1–6 carbon atoms;

$R_3$, $R_5$, and $R_6$, are each, independently, hydrogen, trifluoromethyl, alkyl of 1–6 carbon atoms, alkenyl of 2–7 carbon atoms, alkynyl of 2–7 carbon atoms, cycloalkyl of 3–8 carbon atoms, aryl, Het, arylalkyl having 1–6 carbon atoms in the alkyl chain, Het-alkyl having 1–6 carbon atoms in the alkyl chain, halogen, cyano, nitro, hydroxy, alkoxy of 1–6 carbon atoms, aryloxy, arylalkyloxy having 1–6 carbon atoms in the alkyl chain, alkylthio 1–6 carbon atoms, arylthio, arylamino, Het-amino, arylalkylamino of 1–6 carbons in the alkyl chain, Het-alkylamino having 1–6 carbon atoms in the alkyl chain, hydroxyamino, $-NHCOR_7$, $-NHSO_2R_7$, $-NHP(O)(R_7)_2$, $-COR_8$, $-SO_2R_8$, $-NR_8R_8$, carboxy, alkylcarbonyl of 2–7 carbon atoms, formylalkyl of 2–7 carbon atoms, phosphoryl, alkoxycarbonylalkyl of 3–13 carbon atoms, carboxyalkyl of 2–7 carbon atoms, alkylcarbonylalkyl of 2–13 carbon atoms, arylcarbonylalkyl having 1–6 carbon atoms in the alkyl chain, Het-carbonylalkyl having 1–6 carbon atoms in the alkyl chain, aminocarbonylalkyl of 2–7 carbon atoms, alkylaminocarbonylalkyl of 3–13 carbon atoms, arylaminocarbonylalkyl having 1–6 carbon atoms in the alkyl chain, Het-aminocarbonylalkyl having 1–6 carbon atoms in the alkyl chain, aminosulfonylalkyl of 1–6 carbon atoms, alkylsulfonylalkyl of 2–12 carbon atoms, arylsulfonylalkyl having 1–6 carbon atoms in the alkyl chain, alkylaminosulfonylalkyl of 2–12 carbon atoms, arylaminosulfonylalkyl of 1–6 carbon atoms, Het-aminosulfonylalkyl of 1–6 carbon atoms, phosphonylalkyl of 1–6 carbon atoms, or phosphorylalkyl of 1–6 carbon atoms; or $R_5$ and $R_6$ may be alkylene groups that are taken together to form a 3–8 membered cycloalkyl ring when $R_5$ and $R_6$ are attached to a common carbon atom;

$R_7$ is hydrogen, trifluoromethyl, alkyl of 1–6 carbon atoms, cycloalkyl of 3–8 carbon atoms, alkenyl of 2–7 carbon atoms, alkynyl of 2–7 carbon atoms, aryl, alkoxy of 1–6 carbon atoms, $-NR_8R_9$, or $-NH_9(CH_2)_p-R_8$ $R_8$ is hydrogen, alkoxy of 1–6 carbon atoms, alkyl of 1–6 carbon atoms, hydroxy, aryl substituted with $R_5$ and $R_6$, arylalkoxy having 1–6 carbon atoms in the alkyl chain, $-CR_3R_5R_6$, $-(CH_2)_p-COR_9$, or $-(CH_2)_p-R_9$;

$R_9$ is hydrogen, hydroxy, alkyl of 1–6 carbon atoms, cycloalkyl of 3–8 carbon atoms, alkoxy of 1–6 carbon atoms, aryl substituted with $R_5$ and $R_6$, Het substituted with $R_5$ and $R_6$, arylalkoxy having 1–6 carbon atoms in the alkyl chain, or $-NR_{10}R_{10}$;

$R_{10}$ is hydrogen, alkyl of 1–6 carbon atoms, alkoxycarbonyl of 2–7 carbon atoms, hydroxy, aryl substituted with $R_5$ and $R_6$, or Het substituted with $R_5$ and $R_6$; Het is a monocyclic or bicyclic heterocycle of 5–10 ring atoms, having 1–4 heteroatoms selected from oxygen, nitrogen, and sulfur; wherein the heterocycle may be saturated, unsaturated, or partially unsaturated; and may be optionally fused to a phenyl ring;

m is 1–3;

n is 1–3;

and m+n=4;

p is 0–6;

or a pharmaceutically acceptable salt thereof, and a pharmaceutical carrier.

\* \* \* \* \*